US012630623B2

(12) United States Patent (10) Patent No.: US 12,630,623 B2
Hertz et al. (45) Date of Patent: May 19, 2026

(54) ANTIBODIES WITH REDUCED IMMUNOGENICITY

(71) Applicant: NATIONAL INSTITUTE FOR BIOTECHNOLOGY IN THE NEGEV LTD., Beer-Sheva (IL)

(72) Inventors: Tomer Hertz, Omer (IL); Anat Burkovitz, Ganei Tikva (IL); Amir Aharoni, Kibutz Beit Kama (IL); Inga Soreanu, Beer Sheba (IL)

(73) Assignee: NATIONAL INSTITUTE FOR BIOTECHNOLOGY IN THE NEGEV LTD., Beer-Sheva (IL)

( * ) Notice: Subject to any disclaimer, the term of this patent is extended or adjusted under 35 U.S.C. 154(b) by 1167 days.

(21) Appl. No.: 17/571,905

(22) Filed: Jan. 10, 2022

(65) Prior Publication Data

US 2022/0127349 A1 Apr. 28, 2022

Related U.S. Application Data

(63) Continuation of application No. PCT/IL2020/050772, filed on Jul. 9, 2020.

(60) Provisional application No. 62/871,856, filed on Jul. 9, 2019.

(51) Int. Cl.
| | |
|---|---|
| *C07K 16/28* | (2006.01) |
| *C07K 16/24* | (2006.01) |
| *C12N 15/00* | (2006.01) |
| *C12N 15/13* | (2006.01) |
| *G01N 33/53* | (2006.01) |

(52) U.S. Cl.
CPC ........ *C07K 16/241* (2013.01); *C07K 16/2818* (2013.01); *C07K 2317/30* (2013.01)

(58) Field of Classification Search
None
See application file for complete search history.

(56) References Cited

U.S. PATENT DOCUMENTS

| | | | |
|---|---|---|---|
| 6,258,562 B1 | 7/2001 | Salfeld | |
| 2015/0203579 A1 | 7/2015 | Papadopoulos | |
| 2015/0344571 A1* | 12/2015 | Hong ...................... | A61P 35/00 |
| | | | 435/254.11 |

FOREIGN PATENT DOCUMENTS

| | | |
|---|---|---|
| CN | 104704000 A | 6/2015 |
| CN | 106459192 A | 2/2017 |
| EP | 3178847 A1 | 6/2017 |
| WO | 2006/076594 A2 | 7/2006 |
| WO | 2010121140 A1 | 10/2010 |
| WO | 2012006490 A2 | 1/2012 |
| WO | 2014047222 A2 | 3/2014 |
| WO | 2016000813 A1 | 1/2016 |
| WO | 2018067331 A1 | 4/2018 |
| WO | 2018075792 A1 | 4/2018 |
| WO | 2019091384 A1 | 5/2019 |

OTHER PUBLICATIONS

Lim, H., Lee, S., Lee, H., Lee, J., Son, J., Shin, W., & Heo, Y. S. (2018). Structural Biology of the TNFα Antagonists Used in the Treatment of Rheumatoid Arthritis. International Journal of Molecular Sciences, 19(3), 768. doi:10.3390/ijms19030768.

Sekiguchi, N. et al. (2018). MHC-associated peptide proteomics enabling highly sensitive detection of immunogenic sequences for the development of therapeutic antibodies with low immunogenicity. mAbs. doi:10.1080/19420862.2018.1518888.

Van Schouwenburg, P. A. et al. (2014). Functional Analysis of the Anti-adalimumab Response Using Patient-derived Monoclonal Antibodies. Journal of Biological Chemistry, 289(50), 34482-34488. doi: 10.1074/jbc.m114.615500.

PCT International Search Report for International Application No. PCT/IL2020/050772, mailed Oct. 15, 2020, 14pp.

PCT Written Opinion for International Application No. PCT/IL2020/050772, mailed Oct. 15, 2020, 6pp.

PCT International Preliminary Report on Patentability for International Application No. PCT/IL2020/050772, issued Jan. 11, 2022, 7pp.

Harding FA, Stickler MM, Razo J, DuBridge RB. The immunogenicity of humanized and fully human antibodies: residual immunogenicity resides in the CDR regions. MAbs. May-Jun. 2010;2(3):256-65. doi: 10.4161/mabs.2.3.11641. Epub May 1, 2010. PMID: 20400861; PMCID: PMC2881252.

Kverneland AH, Enevold C, Donia M, Bastholt L, Svane IM, Nielsen CH. Development of anti-drug antibodies is associated with shortened survival in patients with metastatic melanoma treated with ipilimumab. Oncoimmunology. Feb. 1, 2018;7(5):e1424674. doi: 10.1080/2162402X.2018.1424674. PMID: 29721387; PMCID: PMC5927482.

Chao G, Lau WL, Hackel BJ, Sazinsky SL, Lippow SM, Wittrup KD. Isolating and engineering human antibodies using yeast surface display. Nat Protoc. 2006; 1(2):755-68. doi: 10.1038/nprot.2006.94. PMID: 17406305.

Uchanski T, Zogg T, Yin J, Yuan D, Wohlkonig A, Fischer B, Rosenbaum DM, Kobilka BK, Pardon E, Steyaert J. An improved yeast surface display platform for the screening of nanobody immune libraries. Sci Rep. Jan. 23, 2019;9 (1):382. doi: 10.1038/s41598-018-37212-3. PMID: 30674983; PMCID: PMC6344588.

Karle A, Spindeldreher S, Kolbinger F. Secukinumab, a novel anti-IL-17A antibody, shows low immunogenicity potential in human in vitro assays comparable to other marketed biotherapeutics with low clinical immunogenicity. MAbs. 2016;8(3):536-50. doi: 10.1080/19420862.2015.1136761. Epub Jan. 28, 2016. PMID: 26817498; PMCID: PMC4966846.

(Continued)

*Primary Examiner* — Ilia I Ouspenski

(74) *Attorney, Agent, or Firm* — The Roy Gross Law Firm, LLC; Roy D. Gross

(57) ABSTRACT

Methods of reducing immunogenicity of an antibody are provided, as are methods of producing a second antibody from a first. Polypeptide and antibody sequences are also provided.

8 Claims, 16 Drawing Sheets

Specification includes a Sequence Listing.

(56) References Cited

OTHER PUBLICATIONS

Van Schouwenburg, P. A., Kruithof, S., Votsmeier, C., van Schie, K., Hart, M.H., de Jong, R.N., van Buren, E.E., van Ham, M., Aarden, L., Wolbink, G., Wouters, D. & Rispens, T. (2014). Functional Analysis of the Anti-adalimumab Response Using Patient-derived Monoclonal Antibodies. Journal of Biological Chemistry, 289(50), 34482-34488. doi:10.1074/jbc.m114.615500.

* cited by examiner

Predicted immunogenicity-Library 1

SEQ ID NO: 4

SEQ ID NO: 8

SEQ ID NO: 3

SEQ ID NO: 9

Figure 6A

Lib2_c2

| | WT | SEQ ID NO: 97 | SEQ ID NO: 98 | SEQ ID NO: 99 | SEQ ID NO: 100 |
|---|---|---|---|---|---|
| HLA-DRB1*01:01 | 12 | 1925 | | 1088 | 1170 |
| HLA-DRB1*04:04 | 0.7 | 27 | | 2007 | 242 |
| HLA-DRB1*04:05 | 48 | 597 | 1049 | 3025 | |
| HLA-DRB3*02:02 | 5960 | 1360 | 1859 | 11208 | 17588 |
| HLA-DRB1*10:01 | 0.5 | | 18 | | 4.5 |

Lib2_c3

| | WT | SEQ ID NO: 97 | SEQ ID NO: 98 | SEQ ID NO: 99 | SEQ ID NO: 100 |
|---|---|---|---|---|---|
| HLA-DRB1*01:01 | | 1980 | | 4741 | 32 |
| HLA-DRB1*04:04 | 6.4 | | | 7688 | |
| HLA-DRB1*04:05 | 10 | | | 15920 | 16 |
| HLA-DRB3*02:02 | | | | | |
| HLA-DRB1*10:01 | 1.2 | | 0.2 | | 0.2 |

Predicted immunogenicity-Library 1

Figure 7C anti CTLA HC_79_88 ctla_fold_decreasing Fold IC50 decreasing

SEQ ID NO: 5

SEQUENCE LISTING

<160> NUMBER OF SEQ ID NOS: 134

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Leu Tyr Leu Gln Met Asn Ser Leu Arg Ala

```
1               5                    10
```

```
<210> SEQ ID NO 2
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X1
<222> LOCATION: (2)..(2)
<223> OTHER INFORMATION: X1 is selected from D, H, N, S, Y, A, F, and T
<220> FEATURE:
<221> NAME/KEY: X2
<222> LOCATION: (4)..(4)
<223> OTHER INFORMATION: X2 is selected from E, and Q
<220> FEATURE:
<221> NAME/KEY: X3
<222> LOCATION: (7)..(7)
<223> OTHER INFORMATION: X3 is selected from D, G, and S
<220> FEATURE:
<221> NAME/KEY: X4
<222> LOCATION: (9)..(9)
<223> OTHER INFORMATION: X4 is selected from A, G, R, S, and T
<220> FEATURE:
<221> NAME/KEY: X5
<222> LOCATION: (10)..(10)
<223> OTHER INFORMATION: X5 is selected from A, D, E, N, P, T and K

<400> SEQUENCE: 2

Leu Xaa Leu Xaa Met Asn Xaa Leu Xaa Xaa
1               5                    10

<210> SEQ ID NO 3
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X6
<222> LOCATION: (2)..(2)
<223> OTHER INFORMATION: X6 is selected from N, S, Y, A, and H
<220> FEATURE:
<221> NAME/KEY: X2
<222> LOCATION: (4)..(4)
<223> OTHER INFORMATION: X2 is selected from E, and Q
<220> FEATURE:
<221> NAME/KEY: X3
<222> LOCATION: (7)..(7)
<223> OTHER INFORMATION: X3 is selected from D, G, and S
<220> FEATURE:
<221> NAME/KEY: X4
<222> LOCATION: (9)..(9)
<223> OTHER INFORMATION: X4 is selected from A, G, R, S, and T
<220> FEATURE:
<221> NAME/KEY: X7
<222> LOCATION: (10)..(10)
<223> OTHER INFORMATION: X7 is selected from E, P, T, and A

<400> SEQUENCE: 3

Leu Xaa Leu Xaa Met Asn Xaa Leu Xaa Xaa
1               5                    10

<210> SEQ ID NO 4
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X8
<222> LOCATION: (2)..(2)
<223> OTHER INFORMATION: X8 is selected from N, S, Y, D, and H
```

-continued

```
<220> FEATURE:
<221> NAME/KEY: X2
<222> LOCATION: (4)..(4)
<223> OTHER INFORMATION: X2 is selected from E, and Q
<220> FEATURE:
<221> NAME/KEY: X3
<222> LOCATION: (7)..(7)
<223> OTHER INFORMATION: X3 is selected from D, G, and S
<220> FEATURE:
<221> NAME/KEY: X4
<222> LOCATION: (9)..(9)
<223> OTHER INFORMATION: X4 is selected from A, G, R, S, and T
<220> FEATURE:
<221> NAME/KEY: X9
<222> LOCATION: (10)..(10)
<223> OTHER INFORMATION: X9 is selected from D, E, P, N, and A

<400> SEQUENCE: 4

Leu Xaa Leu Xaa Met Asn Xaa Leu Xaa Xaa
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic
<220> FEATURE:
<221> NAME/KEY: X10
<222> LOCATION: (2)..(2)
<223> OTHER INFORMATION: X10 is selected from T, D, and Y
<220> FEATURE:
<221> NAME/KEY: X2
<222> LOCATION: (4)..(4)
<223> OTHER INFORMATION: X2 is selected from E, and Q
<220> FEATURE:
<221> NAME/KEY: X3
<222> LOCATION: (7)..(7)
<223> OTHER INFORMATION: X3 is selected from D, G, and S
<220> FEATURE:
<221> NAME/KEY: X4
<222> LOCATION: (9)..(9)
<223> OTHER INFORMATION: X4 is selected from A, G, R, S, and T
<220> FEATURE:
<221> NAME/KEY: X11
<222> LOCATION: (10)..(10)
<223> OTHER INFORMATION: X11 is selected from E, P, and D

<400> SEQUENCE: 5

Leu Xaa Leu Xaa Met Asn Xaa Leu Xaa Xaa
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic

<400> SEQUENCE: 6

Val Ser Tyr Leu Ser Thr Ala Ser Ser Leu Asp
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
```

```
<220> FEATURE:
<221> NAME/KEY: X13
<222> LOCATION: (3)..(3)
<223> OTHER INFORMATION: X13 is selected from D, E, G, N, Q, T, V, W, F,
      L, and Y
<220> FEATURE:
<221> NAME/KEY: X14
<222> LOCATION: (4)..(4)
<223> OTHER INFORMATION: X14 is selected from A, E, H, L, N, P, Q, S, T,
      V, and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X17
<222> LOCATION: (7)..(7)
<223> OTHER INFORMATION: X17 is selected from A, S, and G
<220> FEATURE:
<221> NAME/KEY: X18
<222> LOCATION: (8)..(8)
<223> OTHER INFORMATION: X18 is selected from E, S, G, and D
<220> FEATURE:
<221> NAME/KEY: X19
<222> LOCATION: (9)..(9)
<223> OTHER INFORMATION: X19 is selected from D, N, G, and S

<400> SEQUENCE: 7

Xaa Ser Xaa Xaa Xaa Xaa Xaa Xaa Xaa Leu Asp
1               5                   10

<210> SEQ ID NO 8
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
<220> FEATURE:
<221> NAME/KEY: X20
<222> LOCATION: (3)..(3)
<223> OTHER INFORMATION: X20 is selected from D, E, G, N, Q, T, V, W,
      and Y
<220> FEATURE:
<221> NAME/KEY: X21
<222> LOCATION: (4)..(4)
<223> OTHER INFORMATION: X21 is selected from A, E, H, L, N, P, Q, S, T,
      and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X22
<222> LOCATION: (7)..(7)
<223> OTHER INFORMATION: X22 is selected from A, and G
<220> FEATURE:
<221> NAME/KEY: X23
<222> LOCATION: (8)..(8)
<223> OTHER INFORMATION: X23 is selected from E, S, and D
<220> FEATURE:
<221> NAME/KEY: X24
<222> LOCATION: (9)..(9)
<223> OTHER INFORMATION: X24 is selected from D, and S

<400> SEQUENCE: 8
```

```
Xaa Ser Xaa Xaa Xaa Xaa Xaa Xaa Xaa Leu Asp
1               5               10

<210> SEQ ID NO 9
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: X25
<222> LOCATION: (3)..(3)
<223> OTHER INFORMATION: X25 is selected from W, Y, G, Q, F, L, and V
<220> FEATURE:
<221> NAME/KEY: X26
<222> LOCATION: (4)..(4)
<223> OTHER INFORMATION: X26 is selected L, V, H, and P
<220> FEATURE:
<221> NAME/KEY: X27
<222> LOCATION: (7)..(7)
<223> OTHER INFORMATION: X27 is selected from A, and S
<220> FEATURE:
<221> NAME/KEY: X28
<222> LOCATION: (8)..(8)
<223> OTHER INFORMATION: X28 is selected from E, S, and G
<220> FEATURE:
<221> NAME/KEY: X29
<222> LOCATION: (9)..(9)
<223> OTHER INFORMATION: X29 is selected from N, S, D, and G

<400> SEQUENCE: 9

Val Ser Xaa Xaa Ser Thr Xaa Xaa Xaa Leu Asp
1               5               10

<210> SEQ ID NO 10
<211> LENGTH: 10
<212> TYPE: PRT
<213> ORGANISM: Artificial
<220> FEATURE:
<223> OTHER INFORMATION: Synthetic

<400> SEQUENCE: 10

Leu Asn Leu Glu Met Asn Asp Leu Thr Pro
1               5               10

<210> SEQ ID NO 11
<211> LENGTH: 10
<212> TYPE: PRT
<213> ORGANISM: Artificial
<220> FEATURE:
<223> OTHER INFORMATION: Synthetic

<400> SEQUENCE: 11

Leu Asn Leu Gln Met Asn Asp Leu Thr Pro
1               5               10

<210> SEQ ID NO 12
<211> LENGTH: 10
<212> TYPE: PRT
<213> ORGANISM: Artificial
<220> FEATURE:
<223> OTHER INFORMATION: Synthetic

<400> SEQUENCE: 12

Leu Tyr Leu Gln Met Asn Ser Leu Arg Pro
1               5               10

<210> SEQ ID NO 13
<211> LENGTH: 10
```

```
<212> TYPE: PRT
<213> ORGANISM: Artificial
<220> FEATURE:
<223> OTHER INFORMATION: Synthetic

<400> SEQUENCE: 13

Leu Tyr Leu Glu Met Asn Gly Leu Ser Pro
1               5                   10

<210> SEQ ID NO 14
<211> LENGTH: 10
<212> TYPE: PRT
<213> ORGANISM: Artificial
<220> FEATURE:
<223> OTHER INFORMATION: Synthetic

<400> SEQUENCE: 14

Leu Ser Leu Gln Met Asn Asp Leu Thr Thr
1               5                   10

<210> SEQ ID NO 15
<211> LENGTH: 10
<212> TYPE: PRT
<213> ORGANISM: Artificial
<220> FEATURE:
<223> OTHER INFORMATION: Synthetic

<400> SEQUENCE: 15

Leu His Leu Glu Met Asn Gly Leu Thr Glu
1               5                   10

<210> SEQ ID NO 16
<211> LENGTH: 10
<212> TYPE: PRT
<213> ORGANISM: Artificial
<220> FEATURE:
<223> OTHER INFORMATION: Synthetic

<400> SEQUENCE: 16

Leu Tyr Leu Glu Met Asn Asp Leu Gly Thr
1               5                   10

<210> SEQ ID NO 17
<211> LENGTH: 10
<212> TYPE: PRT
<213> ORGANISM: Artificial
<220> FEATURE:
<223> OTHER INFORMATION: Synthetic

<400> SEQUENCE: 17

Leu Tyr Leu Glu Met Asn Gly Leu Ala Pro
1               5                   10

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Leu Ala Leu Glu Met Asn Ser Leu Thr Pro
1               5                   10

<210> SEQ ID NO 19
<211> LENGTH: 10
<212> TYPE: PRT
```

```
<213> ORGANISM: Artificial
<220> FEATURE:
<223> OTHER INFORMATION: Synthetic

<400> SEQUENCE: 19

Leu Ser Leu Glu Met Asn Asp Leu Gly Ala
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic

<400> SEQUENCE: 20

Leu Thr Leu Glu Met Asn Ser Leu Thr Pro
1               5                   10

<210> SEQ ID NO 21
<211> LENGTH: 10
<212> TYPE: PRT
<213> ORGANISM: Artificial
<220> FEATURE:
<223> OTHER INFORMATION: Synthetic

<400> SEQUENCE: 21

Leu Thr Leu Glu Met Asn Ser Leu Thr Glu
1               5                   10

<210> SEQ ID NO 22
<211> LENGTH: 10
<212> TYPE: PRT
<213> ORGANISM: Artificial
<220> FEATURE:
<223> OTHER INFORMATION: Synthetic

<400> SEQUENCE: 22

Leu Thr Leu Glu Met Asn Gly Leu Gly Pro
1               5                   10

<210> SEQ ID NO 23
<211> LENGTH: 10
<212> TYPE: PRT
<213> ORGANISM: Artificial
<220> FEATURE:
<223> OTHER INFORMATION: Synthetic

<400> SEQUENCE: 23

Leu Thr Leu Glu Met Asn Gly Leu Ala Pro
1               5                   10

<210> SEQ ID NO 24
<211> LENGTH: 10
<212> TYPE: PRT
<213> ORGANISM: Artificial
<220> FEATURE:
<223> OTHER INFORMATION: Synthetic

<400> SEQUENCE: 24

Leu Tyr Leu Glu Met Asn Asp Leu Ser Asp
1               5                   10

<210> SEQ ID NO 25
<211> LENGTH: 10
<212> TYPE: PRT
<213> ORGANISM: Artificial
```

```
<220> FEATURE:
<223> OTHER INFORMATION: Synthetic

<400> SEQUENCE: 25

Leu Thr Leu Glu Met Asn Gly Leu Ser Pro
1               5                   10

<210> SEQ ID NO 26
<211> LENGTH: 10
<212> TYPE: PRT
<213> ORGANISM: Artificial
<220> FEATURE:
<223> OTHER INFORMATION: Synthetic

<400> SEQUENCE: 26

Leu Thr Leu Glu Met Asn Gly Leu Arg Pro
1               5                   10

<210> SEQ ID NO 27
<211> LENGTH: 121
<212> TYPE: PRT
<213> ORGANISM: Artificial
<220> FEATURE:
<223> OTHER INFORMATION: Synthetic

<400> SEQUENCE: 27

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Asn
65                  70                  75                  80

Leu Glu Met Asn Asp Leu Thr Pro Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 28
<211> LENGTH: 121
<212> TYPE: PRT
<213> ORGANISM: Artificial
<220> FEATURE:
<223> OTHER INFORMATION: Synthetic

<400> SEQUENCE: 28

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Asn
65                  70                  75                  80
```

-continued

```
Leu Gln Met Asn Asp Leu Thr Pro Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 29
<211> LENGTH: 121
<212> TYPE: PRT
<213> ORGANISM: Artificial
<220> FEATURE:
<223> OTHER INFORMATION: Synthetic

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Pro Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 30
<211> LENGTH: 121
<212> TYPE: PRT
<213> ORGANISM: Artificial
<220> FEATURE:
<223> OTHER INFORMATION: Synthetic

<400> SEQUENCE: 30

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Glu Met Asn Gly Leu Ser Pro Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120
```

-continued

```
<210> SEQ ID NO 31
<211> LENGTH: 121
<212> TYPE: PRT
<213> ORGANISM: Artificial
<220> FEATURE:
<223> OTHER INFORMATION: Synthetic

<400> SEQUENCE: 31

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Ser
65                  70                  75                  80

Leu Gln Met Asn Asp Leu Thr Thr Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 32
<211> LENGTH: 121
<212> TYPE: PRT
<213> ORGANISM: Artificial
<220> FEATURE:
<223> OTHER INFORMATION: Synthetic

<400> SEQUENCE: 32

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu His
65                  70                  75                  80

Leu Glu Met Asn Gly Leu Thr Glu Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 33
<211> LENGTH: 121
<212> TYPE: PRT
<213> ORGANISM: Artificial
<220> FEATURE:
<223> OTHER INFORMATION: Synthetic

<400> SEQUENCE: 33

Glu Val Gln Leu Val Glu Ser Gly Gly Gly Leu Val Gln Pro Gly Arg
1               5                   10                  15
```

Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Glu Met Asn Asp Leu Gly Thr Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 34
<211> LENGTH: 121
<212> TYPE: PRT
<213> ORGANISM: Artificial
<220> FEATURE:
<223> OTHER INFORMATION: Synthetic

<400> SEQUENCE: 34

Glu Val Gln Leu Val Glu Ser Gly Gly Gly Leu Val Gln Pro Gly Arg
1                   5                   10                  15

Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Glu Met Asn Gly Leu Ala Pro Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 35
<211> LENGTH: 121
<212> TYPE: PRT
<213> ORGANISM: Artificial
<220> FEATURE:
<223> OTHER INFORMATION: Synthetic

<400> SEQUENCE: 35

Glu Val Gln Leu Val Glu Ser Gly Gly Gly Leu Val Gln Pro Gly Arg
1                   5                   10                  15

Ser Leu Arg Leu Ser Cys Ala Ala Ser Gly Phe Thr Phe Asp Asp Tyr
        20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Ala

```
65                    70                    75                    80

Leu Glu Met Asn Ser Leu Thr Pro Glu Asp Thr Ala Val Tyr Tyr Cys
                85                    90                    95

Ala Lys Val Ser Tyr Leu Ser Thr Ala Ser Ser Leu Asp Tyr Trp Gly
                100                    105                    110

Gln Gly Thr Leu Val Thr Val Ser Ser
        115                    120

<210> SEQ ID NO 36
<211> LENGTH: 121
<212> TYPE: PRT
<213> ORGANISM: Artificial
<220> FEATURE:
<223> OTHER INFORMATION: Synthetic

<400> SEQUENCE: 36

Glu Val Gln Leu Val Glu Ser Gly Gly Gly Leu Val Gln Pro Gly Arg
1                    5                    10                    15

Ser Leu Arg Leu Ser Cys Ala Ala Ser Gly Phe Thr Phe Asp Asp Tyr
                20                    25                    30

Ala Met His Trp Val Arg Gln Ala Pro Gly Lys Gly Leu Glu Trp Val
        35                    40                    45

Ser Ala Ile Thr Trp Asn Ser Gly His Ile Asp Tyr Ala Asp Ser Val
        50                    55                    60

Glu Gly Arg Phe Thr Ile Ser Arg Asp Asn Ala Lys Asn Ser Leu Ser
65                    70                    75                    80

Leu Glu Met Asn Asp Leu Gly Ala Glu Asp Thr Ala Val Tyr Tyr Cys
                85                    90                    95

Ala Lys Val Ser Tyr Leu Ser Thr Ala Ser Ser Leu Asp Tyr Trp Gly
                100                    105                    110

Gln Gly Thr Leu Val Thr Val Ser Ser
        115                    120

<210> SEQ ID NO 37
<211> LENGTH: 10
<212> TYPE: PRT
<213> ORGANISM: Artificial
<220> FEATURE:
<223> OTHER INFORMATION: Synthetic

<400> SEQUENCE: 37

Leu Tyr Leu Glu Met Asn Asp Leu Gly Pro
1                    5                    10

<210> SEQ ID NO 38
<211> LENGTH: 10
<212> TYPE: PRT
<213> ORGANISM: Artificial
<220> FEATURE:
<223> OTHER INFORMATION: Synthetic

<400> SEQUENCE: 38

Leu Tyr Leu Gln Met Asn Ser Leu Thr Pro
1                    5                    10

<210> SEQ ID NO 39
<211> LENGTH: 10
<212> TYPE: PRT
<213> ORGANISM: Artificial
<220> FEATURE:
<223> OTHER INFORMATION: Synthetic
```

-continued

```
<400> SEQUENCE: 39

Leu Tyr Leu Glu Met Asn Gly Leu Arg Glu
1               5                   10

<210> SEQ ID NO 40
<211> LENGTH: 10
<212> TYPE: PRT
<213> ORGANISM: Artificial
<220> FEATURE:
<223> OTHER INFORMATION: Synthetic

<400> SEQUENCE: 40

Leu Tyr Leu Glu Met Asn Ser Leu Gly Pro
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic

<400> SEQUENCE: 41

Leu Tyr Leu Gln Met Asn Asp Leu Ala Ala
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic

<400> SEQUENCE: 42

Leu Tyr Leu Glu Met Asn Ser Leu Thr Pro
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic

<400> SEQUENCE: 43

Leu Tyr Leu Glu Met Asn Asp Leu Arg Pro
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic

<400> SEQUENCE: 44

Leu His Leu Glu Met Asn Asp Leu Ala Pro
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic

<400> SEQUENCE: 45
```

```
Leu His Leu Glu Met Asn Asp Leu Ser Pro
1               5                   10

<210> SEQ ID NO 46
<211> LENGTH: 10
<212> TYPE: PRT
<213> ORGANISM: Artificial
<220> FEATURE:
<223> OTHER INFORMATION: Synthetic

<400> SEQUENCE: 46

Leu Tyr Leu Glu Met Asn Asp Leu Ser Pro
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic

<400> SEQUENCE: 47

Leu Tyr Leu Glu Met Asn Ser Leu Ala Pro
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic

<400> SEQUENCE: 48

Leu Ala Leu Gln Met Asn Asp Leu Arg Pro
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic

<400> SEQUENCE: 49

Leu Tyr Leu Gln Met Asn Asp Leu Thr Pro
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic

<400> SEQUENCE: 50

Leu Tyr Leu Gln Met Asn Asp Leu Gly Pro
1               5                   10

<210> SEQ ID NO 51
<211> LENGTH: 10
<212> TYPE: PRT
<213> ORGANISM: Artificial
<220> FEATURE:
<223> OTHER INFORMATION: Synthetic

<400> SEQUENCE: 51
```

```
Leu His Leu Gln Met Asn Asp Leu Arg Pro
1               5               10

<210> SEQ ID NO 52
<211> LENGTH: 10
<212> TYPE: PRT
<213> ORGANISM: Artificial
<220> FEATURE:
<223> OTHER INFORMATION: Synthetic

<400> SEQUENCE: 52

Leu Tyr Leu Glu Met Asn Asp Leu Ala Pro
1               5               10

<210> SEQ ID NO 53
<211> LENGTH: 10
<212> TYPE: PRT
<213> ORGANISM: Artificial
<220> FEATURE:
<223> OTHER INFORMATION: Synthetic

<400> SEQUENCE: 53

Leu Asp Leu Glu Met Asn Asp Leu Arg Thr
1               5               10

<210> SEQ ID NO 54
<211> LENGTH: 10
<212> TYPE: PRT
<213> ORGANISM: Artificial
<220> FEATURE:
<223> OTHER INFORMATION: Synthetic

<400> SEQUENCE: 54

Leu Tyr Leu Glu Met Asn Ser Leu Thr Lys
1               5               10

<210> SEQ ID NO 55
<211> LENGTH: 10
<212> TYPE: PRT
<213> ORGANISM: Artificial
<220> FEATURE:
<223> OTHER INFORMATION: Synthetic

<400> SEQUENCE: 55

Leu Asp Leu Gln Met Asn Asp Leu Thr Pro
1               5               10

<210> SEQ ID NO 56
<211> LENGTH: 10
<212> TYPE: PRT
<213> ORGANISM: Artificial
<220> FEATURE:
<223> OTHER INFORMATION: Synthetic

<400> SEQUENCE: 56

Leu Tyr Leu Glu Met Asn Asp Leu Gly Ala
1               5               10

<210> SEQ ID NO 57
<211> LENGTH: 10
<212> TYPE: PRT
<213> ORGANISM: Artificial
<220> FEATURE:
<223> OTHER INFORMATION: Synthetic

<400> SEQUENCE: 57

Leu Ser Leu Glu Met Asn Asp Leu Arg Pro
```

-continued

```
1               5                   10

<210> SEQ ID NO 58
<211> LENGTH: 10
<212> TYPE: PRT
<213> ORGANISM: Artificial
<220> FEATURE:
<223> OTHER INFORMATION: Synthetic

<400> SEQUENCE: 58

Leu Tyr Leu Glu Met Asn Ser Leu Thr Ala
1               5                   10

<210> SEQ ID NO 59
<211> LENGTH: 10
<212> TYPE: PRT
<213> ORGANISM: Artificial
<220> FEATURE:
<223> OTHER INFORMATION: Synthetic

<400> SEQUENCE: 59

Leu His Leu Gln Met Asn Asp Leu Thr Pro
1               5                   10

<210> SEQ ID NO 60
<211> LENGTH: 10
<212> TYPE: PRT
<213> ORGANISM: Artificial
<220> FEATURE:
<223> OTHER INFORMATION: Synthetic

<400> SEQUENCE: 60

Leu Tyr Leu Glu Met Asn Ser Leu Ser Pro
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic

<400> SEQUENCE: 61

Leu Ser Leu Glu Met Asn Asp Leu Ala Pro
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic

<400> SEQUENCE: 62

Leu Ser Leu Glu Met Asn Asp Leu Thr Thr
1               5                   10

<210> SEQ ID NO 63
<211> LENGTH: 10
<212> TYPE: PRT
<213> ORGANISM: Artificial
<220> FEATURE:
<223> OTHER INFORMATION: Synthetic

<400> SEQUENCE: 63

Leu Tyr Leu Glu Met Asn Asp Leu Ala Asp
1               5                   10
```

```
<210> SEQ ID NO 64
<211> LENGTH: 10
<212> TYPE: PRT
<213> ORGANISM: Artificial
<220> FEATURE:
<223> OTHER INFORMATION: Synthetic

<400> SEQUENCE: 64

Leu His Leu Glu Met Asn Ser Leu Thr Pro
1               5                   10

<210> SEQ ID NO 65
<211> LENGTH: 10
<212> TYPE: PRT
<213> ORGANISM: Artificial
<220> FEATURE:
<223> OTHER INFORMATION: Synthetic

<400> SEQUENCE: 65

Leu Phe Leu Glu Met Asn Asp Leu Gly Pro
1               5                   10

<210> SEQ ID NO 66
<211> LENGTH: 10
<212> TYPE: PRT
<213> ORGANISM: Artificial
<220> FEATURE:
<223> OTHER INFORMATION: Synthetic

<400> SEQUENCE: 66

Leu Ala Leu Glu Met Asn Asp Leu Arg Pro
1               5                   10

<210> SEQ ID NO 67
<211> LENGTH: 10
<212> TYPE: PRT
<213> ORGANISM: Artificial
<220> FEATURE:
<223> OTHER INFORMATION: Synthetic

<400> SEQUENCE: 67

Leu Tyr Leu Glu Met Asn Asp Leu Ser Lys
1               5                   10

<210> SEQ ID NO 68
<211> LENGTH: 10
<212> TYPE: PRT
<213> ORGANISM: Artificial
<220> FEATURE:
<223> OTHER INFORMATION: Synthetic

<400> SEQUENCE: 68

Leu Tyr Leu Glu Met Asn Asp Leu Gly Glu
1               5                   10

<210> SEQ ID NO 69
<211> LENGTH: 10
<212> TYPE: PRT
<213> ORGANISM: Artificial
<220> FEATURE:
<223> OTHER INFORMATION: Synthetic

<400> SEQUENCE: 69

Leu Tyr Leu Glu Met Asn Asp Leu Thr Ala
1               5                   10
```

<210> SEQ ID NO 70
<211> LENGTH: 10
<212> TYPE: PRT
<213> ORGANISM: Artificial
<220> FEATURE:
<223> OTHER INFORMATION: Synthetic

<400> SEQUENCE: 70

Leu Tyr Leu Glu Met Asn Asp Leu Thr Pro
1               5                   10

<210> SEQ ID NO 71
<211> LENGTH: 10
<212> TYPE: PRT
<213> ORGANISM: Artificial
<220> FEATURE:
<223> OTHER INFORMATION: Synthetic

<400> SEQUENCE: 71

Leu Tyr Leu Gln Met Asn Asp Leu Arg Ala
1               5                   10

<210> SEQ ID NO 72
<211> LENGTH: 10
<212> TYPE: PRT
<213> ORGANISM: Artificial
<220> FEATURE:
<223> OTHER INFORMATION: Synthetic

<400> SEQUENCE: 72

Leu Ser Leu Glu Met Asn Gly Leu Thr Pro
1               5                   10

<210> SEQ ID NO 73
<211> LENGTH: 10
<212> TYPE: PRT
<213> ORGANISM: Artificial
<220> FEATURE:
<223> OTHER INFORMATION: Synthetic

<400> SEQUENCE: 73

Leu Tyr Leu Glu Met Asn Asp Leu Ala Thr
1               5                   10

<210> SEQ ID NO 74
<211> LENGTH: 10
<212> TYPE: PRT
<213> ORGANISM: Artificial
<220> FEATURE:
<223> OTHER INFORMATION: Synthetic

<400> SEQUENCE: 74

Leu Asn Leu Gln Met Asn Asp Leu Arg Ala
1               5                   10

<210> SEQ ID NO 75
<211> LENGTH: 10
<212> TYPE: PRT
<213> ORGANISM: Artificial
<220> FEATURE:
<223> OTHER INFORMATION: Synthetic

<400> SEQUENCE: 75

Leu Ala Leu Glu Met Asn Asp Leu Ala Glu
1               5                   10

<210> SEQ ID NO 76
<211> LENGTH: 10
<212> TYPE: PRT
<213> ORGANISM: Artificial
<220> FEATURE:
<223> OTHER INFORMATION: Synthetic

<400> SEQUENCE: 76

Leu His Leu Gln Met Asn Ser Leu Thr Pro
1               5                   10

<210> SEQ ID NO 77
<211> LENGTH: 10
<212> TYPE: PRT
<213> ORGANISM: Artificial
<220> FEATURE:
<223> OTHER INFORMATION: Synthetic

<400> SEQUENCE: 77

Leu Ser Leu Glu Met Asn Asp Leu Ser Asp
1               5                   10

<210> SEQ ID NO 78
<211> LENGTH: 10
<212> TYPE: PRT
<213> ORGANISM: Artificial
<220> FEATURE:
<223> OTHER INFORMATION: Synthetic

<400> SEQUENCE: 78

Leu Tyr Leu Glu Met Asn Gly Leu Gly Ala
1               5                   10

<210> SEQ ID NO 79
<211> LENGTH: 10
<212> TYPE: PRT
<213> ORGANISM: Artificial
<220> FEATURE:
<223> OTHER INFORMATION: Synthetic

<400> SEQUENCE: 79

Leu Asp Leu Glu Met Asn Asp Leu Ser Pro
1               5                   10

<210> SEQ ID NO 80
<211> LENGTH: 10
<212> TYPE: PRT
<213> ORGANISM: Artificial
<220> FEATURE:
<223> OTHER INFORMATION: Synthetic

<400> SEQUENCE: 80

Leu Ala Leu Glu Met Asn Ser Leu Thr Asp
1               5                   10

<210> SEQ ID NO 81
<211> LENGTH: 10
<212> TYPE: PRT
<213> ORGANISM: Artificial
<220> FEATURE:
<223> OTHER INFORMATION: Synthetic

<400> SEQUENCE: 81

Leu Thr Leu Glu Met Asn Gly Leu Ala Pro
1               5                   10

<210> SEQ ID NO 82

```
<211> LENGTH: 10
<212> TYPE: PRT
<213> ORGANISM: Artificial
<220> FEATURE:
<223> OTHER INFORMATION: Synthetic

<400> SEQUENCE: 82

Leu Thr Leu Gln Met Asn Asp Leu Ala Pro
1               5                   10

<210> SEQ ID NO 83
<211> LENGTH: 10
<212> TYPE: PRT
<213> ORGANISM: Artificial
<220> FEATURE:
<223> OTHER INFORMATION: Synthetic

<400> SEQUENCE: 83

Leu Asp Leu Gln Met Asn Ser Leu Ala Ala
1               5                   10

<210> SEQ ID NO 84
<211> LENGTH: 10
<212> TYPE: PRT
<213> ORGANISM: Artificial
<220> FEATURE:
<223> OTHER INFORMATION: Synthetic

<400> SEQUENCE: 84

Leu Ala Leu Glu Met Asn Gly Leu Thr Pro
1               5                   10

<210> SEQ ID NO 85
<211> LENGTH: 10
<212> TYPE: PRT
<213> ORGANISM: Artificial
<220> FEATURE:
<223> OTHER INFORMATION: Synthetic

<400> SEQUENCE: 85

Leu Asn Leu Glu Met Asn Ser Leu Gly Pro
1               5                   10

<210> SEQ ID NO 86
<211> LENGTH: 10
<212> TYPE: PRT
<213> ORGANISM: Artificial
<220> FEATURE:
<223> OTHER INFORMATION: Synthetic

<400> SEQUENCE: 86

Leu Asp Leu Gln Met Asn Ser Leu Ala Glu
1               5                   10

<210> SEQ ID NO 87
<211> LENGTH: 10
<212> TYPE: PRT
<213> ORGANISM: Artificial
<220> FEATURE:
<223> OTHER INFORMATION: Synthetic

<400> SEQUENCE: 87

Leu Asp Leu Gln Met Asn Ser Leu Ser Ala
1               5                   10

<210> SEQ ID NO 88
<211> LENGTH: 10
```

```
<212> TYPE: PRT
<213> ORGANISM: Artificial
<220> FEATURE:
<223> OTHER INFORMATION: Synthetic

<400> SEQUENCE: 88

Leu Tyr Leu Gln Met Asn Asp Leu Ala Thr
1               5                   10

<210> SEQ ID NO 89
<211> LENGTH: 10
<212> TYPE: PRT
<213> ORGANISM: Artificial
<220> FEATURE:
<223> OTHER INFORMATION: Synthetic

<400> SEQUENCE: 89

Leu Tyr Leu Gln Met Asn Gly Leu Thr Ala
1               5                   10

<210> SEQ ID NO 90
<211> LENGTH: 10
<212> TYPE: PRT
<213> ORGANISM: Artificial
<220> FEATURE:
<223> OTHER INFORMATION: Synthetic

<400> SEQUENCE: 90

Leu Asp Leu Gln Met Asn Asp Leu Ser Pro
1               5                   10

<210> SEQ ID NO 91
<211> LENGTH: 10
<212> TYPE: PRT
<213> ORGANISM: Artificial
<220> FEATURE:
<223> OTHER INFORMATION: Synthetic

<400> SEQUENCE: 91

Leu Ser Leu Glu Met Asn Gly Leu Thr Asp
1               5                   10

<210> SEQ ID NO 92
<211> LENGTH: 10
<212> TYPE: PRT
<213> ORGANISM: Artificial
<220> FEATURE:
<223> OTHER INFORMATION: Synthetic

<400> SEQUENCE: 92

Leu Asp Leu Gln Met Asn Asp Leu Gly Pro
1               5                   10

<210> SEQ ID NO 93
<211> LENGTH: 10
<212> TYPE: PRT
<213> ORGANISM: Artificial
<220> FEATURE:
<223> OTHER INFORMATION: Synthetic

<400> SEQUENCE: 93

Leu Asp Leu Glu Met Asn Asp Leu Gly Pro
1               5                   10

<210> SEQ ID NO 94
<211> LENGTH: 10
<212> TYPE: PRT
```

-continued

```
<213> ORGANISM: Artificial
<220> FEATURE:
<223> OTHER INFORMATION: Synthetic

<400> SEQUENCE: 94

Leu Tyr Leu Glu Met Asn Ser Leu Thr Thr
1               5                   10

<210> SEQ ID NO 95
<211> LENGTH: 10
<212> TYPE: PRT
<213> ORGANISM: Artificial
<220> FEATURE:
<223> OTHER INFORMATION: Synthetic

<400> SEQUENCE: 95

Leu Tyr Leu Glu Met Asn Asp Leu Thr Thr
1               5                   10

<210> SEQ ID NO 96
<211> LENGTH: 10
<212> TYPE: PRT
<213> ORGANISM: Artificial
<220> FEATURE:
<223> OTHER INFORMATION: Synthetic

<400> SEQUENCE: 96

Leu His Leu Glu Met Asn Asp Leu Arg Pro
1               5                   10

<210> SEQ ID NO 97
<211> LENGTH: 11
<212> TYPE: PRT
<213> ORGANISM: Artificial
<220> FEATURE:
<223> OTHER INFORMATION: Synthetic

<400> SEQUENCE: 97

Val Ser Trp Val Ser Thr Ser Ser Ser Leu Asp
1               5                   10

<210> SEQ ID NO 98
<211> LENGTH: 11
<212> TYPE: PRT
<213> ORGANISM: Artificial
<220> FEATURE:
<223> OTHER INFORMATION: Synthetic

<400> SEQUENCE: 98

Val Ser Trp Leu Ser Thr Ser Gly Ser Leu Asp
1               5                   10

<210> SEQ ID NO 99
<211> LENGTH: 11
<212> TYPE: PRT
<213> ORGANISM: Artificial
<220> FEATURE:
<223> OTHER INFORMATION: Synthetic

<400> SEQUENCE: 99

Val Ser Gly Pro Ser Thr Ser Gly Asn Leu Asp
1               5                   10

<210> SEQ ID NO 100
<211> LENGTH: 11
<212> TYPE: PRT
<213> ORGANISM: Artificial
```

-continued

<220> FEATURE:
<223> OTHER INFORMATION: Synthetic

<400> SEQUENCE: 100

Val Ser Trp Leu Ser Thr Ser Gly Asn Leu Asp
1               5               10

<210> SEQ ID NO 101
<211> LENGTH: 11
<212> TYPE: PRT
<213> ORGANISM: Artificial
<220> FEATURE:
<223> OTHER INFORMATION: Synthetic

<400> SEQUENCE: 101

Val Ser Phe His Ser Thr Ser Glu Gly Leu Asp
1               5               10

<210> SEQ ID NO 102
<211> LENGTH: 11
<212> TYPE: PRT
<213> ORGANISM: Artificial
<220> FEATURE:
<223> OTHER INFORMATION: Synthetic

<400> SEQUENCE: 102

Val Ser Trp Leu Ser Thr Ser Ser Ser Leu Asp
1               5               10

<210> SEQ ID NO 103
<211> LENGTH: 11
<212> TYPE: PRT
<213> ORGANISM: Artificial
<220> FEATURE:
<223> OTHER INFORMATION: Synthetic

<400> SEQUENCE: 103

Val Ser Tyr Leu Ser Thr Ser Gly Asn Leu Asp
1               5               10

<210> SEQ ID NO 104
<211> LENGTH: 11
<212> TYPE: PRT
<213> ORGANISM: Artificial
<220> FEATURE:
<223> OTHER INFORMATION: Synthetic

<400> SEQUENCE: 104

Val Ser Tyr Leu Ser Thr Ser Gly Ser Leu Asp
1               5               10

<210> SEQ ID NO 105
<211> LENGTH: 11
<212> TYPE: PRT
<213> ORGANISM: Artificial
<220> FEATURE:
<223> OTHER INFORMATION: Synthetic

<400> SEQUENCE: 105

Val Ser Gln Leu Ser Thr Ser Gly Asp Leu Asp
1               5               10

<210> SEQ ID NO 106
<211> LENGTH: 11
<212> TYPE: PRT
<213> ORGANISM: Artificial
<220> FEATURE:

```
<223> OTHER INFORMATION: Synthetic

<400> SEQUENCE: 106

Val Ser Gln Leu Ser Thr Ser Gly Ser Leu Asp
1               5                   10

<210> SEQ ID NO 107
<211> LENGTH: 11
<212> TYPE: PRT
<213> ORGANISM: Artificial
<220> FEATURE:
<223> OTHER INFORMATION: Synthetic

<400> SEQUENCE: 107

Val Ser Trp Leu Ser Thr Ser Gly Ser Leu Asp
1               5                   10

<210> SEQ ID NO 108
<211> LENGTH: 11
<212> TYPE: PRT
<213> ORGANISM: Artificial
<220> FEATURE:
<223> OTHER INFORMATION: Synthetic

<400> SEQUENCE: 108

Val Ser Gln Leu Ser Thr Ser Gly Asp Leu Asp
1               5                   10

<210> SEQ ID NO 109
<211> LENGTH: 11
<212> TYPE: PRT
<213> ORGANISM: Artificial
<220> FEATURE:
<223> OTHER INFORMATION: Synthetic

<400> SEQUENCE: 109

Val Ser Val Leu Ser Thr Ser Gly Ser Leu Asp
1               5                   10

<210> SEQ ID NO 110
<211> LENGTH: 11
<212> TYPE: PRT
<213> ORGANISM: Artificial
<220> FEATURE:
<223> OTHER INFORMATION: Synthetic

<400> SEQUENCE: 110

Val Ser Leu Leu Ser Thr Ser Gly Ser Leu Asp
1               5                   10

<210> SEQ ID NO 111
<211> LENGTH: 11
<212> TYPE: PRT
<213> ORGANISM: Artificial
<220> FEATURE:
<223> OTHER INFORMATION: Synthetic

<400> SEQUENCE: 111

Val Ser Val Leu Ser Thr Ser Gly Asp Leu Asp
1               5                   10

<210> SEQ ID NO 112
<211> LENGTH: 11
<212> TYPE: PRT
<213> ORGANISM: Artificial
<220> FEATURE:
<223> OTHER INFORMATION: Synthetic
```

```
<400> SEQUENCE: 112

Val Ser Gly Val Ser Thr Ser Gly Ser Leu Asp
1               5                   10

<210> SEQ ID NO 113
<211> LENGTH: 10
<212> TYPE: PRT
<213> ORGANISM: Artificial
<220> FEATURE:
<223> OTHER INFORMATION: Synthetic

<400> SEQUENCE: 113

Leu Asp Leu Gln Met Asn Gly Leu Gly Pro
1               5                   10

<210> SEQ ID NO 114
<211> LENGTH: 5
<212> TYPE: PRT
<213> ORGANISM: Artificial
<220> FEATURE:
<223> OTHER INFORMATION: Synthetic

<400> SEQUENCE: 114

Asp Tyr Ala Met His
1               5

<210> SEQ ID NO 115
<211> LENGTH: 4
<212> TYPE: PRT
<213> ORGANISM: Artificial
<220> FEATURE:
<223> OTHER INFORMATION: Synthetic

<400> SEQUENCE: 115

Ala Ile Thr Trp
1

<210> SEQ ID NO 116
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
<220> FEATURE:
<221> NAME/KEY: X13
<222> LOCATION: (3)..(3)
<223> OTHER INFORMATION: X13 is selected from D, E, G, N, Q, T, V, W, F,
      L, and Y
<220> FEATURE:
<221> NAME/KEY: X14
<222> LOCATION: (4)..(4)
<223> OTHER INFORMATION: X14 is selected from A, E, H, L, N, P, Q, S, T,
      V, and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X17
<222> LOCATION: (7)..(7)
<223> OTHER INFORMATION: X17 is selected from A, S, and G
<220> FEATURE:
```

```
<221> NAME/KEY: X18
<222> LOCATION: (8)..(8)
<223> OTHER INFORMATION: X18 is selected from E, S, G, and D,
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: X30
<222> LOCATION: (12)..(12)
<223> OTHER INFORMATION: X30 is selected from Y and N

<400> SEQUENCE: 116

Xaa Ser Xaa Xaa Xaa Xaa Xaa Xaa Xaa Leu Asp Xaa
1               5                   10

<210> SEQ ID NO 117
<211> LENGTH: 11
<212> TYPE: PRT
<213> ORGANISM: Artificial
<220> FEATURE:
<223> OTHER INFORMATION: Synthetic

<400> SEQUENCE: 117

Arg Ala Ser Gln Gly Ile Arg Asn Tyr Leu Ala
1               5                   10

<210> SEQ ID NO 118
<211> LENGTH: 7
<212> TYPE: PRT
<213> ORGANISM: Artificial
<220> FEATURE:
<223> OTHER INFORMATION: Synthetic

<400> SEQUENCE: 118

Ala Ala Ser Thr Leu Gln Ser
1               5

<210> SEQ ID NO 119
<211> LENGTH: 9
<212> TYPE: PRT
<213> ORGANISM: Artificial
<220> FEATURE:
<223> OTHER INFORMATION: Synthetic
<220> FEATURE:
<221> NAME/KEY: X31
<222> LOCATION: (9)..(9)
<223> OTHER INFORMATION: X31 is selected from T and A

<400> SEQUENCE: 119

Gln Arg Tyr Asn Arg Ala Pro Tyr Xaa
1               5

<210> SEQ ID NO 120
<211> LENGTH: 9
<212> TYPE: PRT
<213> ORGANISM: Artificial
<220> FEATURE:
<223> OTHER INFORMATION: Synthetic

<400> SEQUENCE: 120

Gln Arg Tyr Asn Arg Ala Pro Tyr Thr
1               5

<210> SEQ ID NO 121
<211> LENGTH: 12
<212> TYPE: PRT
<213> ORGANISM: Artificial
<220> FEATURE:
```

```
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
<220> FEATURE:
<221> NAME/KEY: X13
<222> LOCATION: (3)..(3)
<223> OTHER INFORMATION: X13 is selected from D, E, G, N, Q, T, V, W, F,
      L, and Y
<220> FEATURE:
<221> NAME/KEY: X14
<222> LOCATION: (4)..(4)
<223> OTHER INFORMATION: X14 is selected from A, E, H, L, N, P, Q, S, T,
      V, and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X17
<222> LOCATION: (7)..(7)
<223> OTHER INFORMATION: X17 is selected from A, S, and G
<220> FEATURE:
<221> NAME/KEY: X18
<222> LOCATION: (8)..(8)
<223> OTHER INFORMATION: X18 is selected from E, S, G, and D
<220> FEATURE:
<221> NAME/KEY: X19
<222> LOCATION: (9)..(9)
<223> OTHER INFORMATION: X19 is selected from D, N, G, and S

<400> SEQUENCE: 121

Xaa Ser Xaa Xaa Xaa Xaa Xaa Xaa Xaa Leu Asp Tyr
1               5                   10

<210> SEQ ID NO 122
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
<220> FEATURE:
<221> NAME/KEY: X20
<222> LOCATION: (3)..(3)
<223> OTHER INFORMATION: X20 is selected from D, E, G, N, Q, T, V, W,
      and Y
<220> FEATURE:
<221> NAME/KEY: X21
<222> LOCATION: (4)..(4)
<223> OTHER INFORMATION: X21 is selected from A, E, H, L, N, P, Q, S, T,
      and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X22
<222> LOCATION: (7)..(7)
<223> OTHER INFORMATION: X22 is selected from A, and G
<220> FEATURE:
<221> NAME/KEY: X23
<222> LOCATION: (8)..(8)
<223> OTHER INFORMATION: X23 is selected from E, S, and D
<220> FEATURE:
```

-continued

```
<221> NAME/KEY: X24
<222> LOCATION: (9)..(9)
<223> OTHER INFORMATION: X24 is selected from D, and S
<220> FEATURE:
<221> NAME/KEY: X31
<222> LOCATION: (12)..(12)
<223> OTHER INFORMATION: X31 is selected from T and A

<400> SEQUENCE: 122

Xaa Ser Xaa Xaa Xaa Xaa Xaa Xaa Xaa Leu Asp Xaa
1               5                   10

<210> SEQ ID NO 123
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: X25
<222> LOCATION: (3)..(3)
<223> OTHER INFORMATION: X25 is selected from W, Y, G, Q, F, L, and V
<220> FEATURE:
<221> NAME/KEY: X26
<222> LOCATION: (4)..(4)
<223> OTHER INFORMATION: X26 is selected L, V, H, and P
<220> FEATURE:
<221> NAME/KEY: X27
<222> LOCATION: (7)..(7)
<223> OTHER INFORMATION: X27 is selected from A, and S
<220> FEATURE:
<221> NAME/KEY: X28
<222> LOCATION: (8)..(8)
<223> OTHER INFORMATION: X28 is selected from E, S, and G
<220> FEATURE:
<221> NAME/KEY: X29
<222> LOCATION: (9)..(9)
<223> OTHER INFORMATION: X29 is selected from N, S, D, and G
<220> FEATURE:
<221> NAME/KEY: X31
<222> LOCATION: (12)..(12)
<223> OTHER INFORMATION: X31 is selected from T and A

<400> SEQUENCE: 123

Val Ser Xaa Xaa Ser Thr Xaa Xaa Xaa Leu Asp Xaa
1               5                   10

<210> SEQ ID NO 124
<211> LENGTH: 9
<212> TYPE: PRT
<213> ORGANISM: Artificial
<220> FEATURE:
<223> OTHER INFORMATION: Synthetic

<400> SEQUENCE: 124

Gln Arg Tyr Asn Arg Ala Pro Tyr Ala
1               5

<210> SEQ ID NO 125
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (1)..(1)
<223> OTHER INFORMATION: X12 is selected from D, E, and V
<220> FEATURE:
<221> NAME/KEY: X13
<222> LOCATION: (3)..(3)
<223> OTHER INFORMATION: X13 is selected from D, E, G, N, Q, T, V, W, F,
     L, and Y
```

```
<220> FEATURE:
<221> NAME/KEY: X14
<222> LOCATION: (4)..(4)
<223> OTHER INFORMATION: X14 is selected from A, E, H, L, N, P, Q, S, T,
      V, and W
<220> FEATURE:
<221> NAME/KEY: X15
<222> LOCATION: (5)..(5)
<223> OTHER INFORMATION: X15 is selected from E, S, and G
<220> FEATURE:
<221> NAME/KEY: X16
<222> LOCATION: (6)..(6)
<223> OTHER INFORMATION: X16 is selected from E, G, H, K, P, R, and T
<220> FEATURE:
<221> NAME/KEY: X17
<222> LOCATION: (7)..(7)
<223> OTHER INFORMATION: X17 is selected from A, S, and G
<220> FEATURE:
<221> NAME/KEY: X18
<222> LOCATION: (8)..(8)
<223> OTHER INFORMATION: X18 is selected from E, S, G, and D
<220> FEATURE:
<221> NAME/KEY: X19
<222> LOCATION: (9)..(9)
<223> OTHER INFORMATION: X19 is selected from D, N, G, and S

<400> SEQUENCE: 125

Xaa Ser Xaa Xaa Xaa Xaa Xaa Xaa Xaa Leu Asp Asn
1               5                   10

<210> SEQ ID NO 126
<211> LENGTH: 80
<212> TYPE: PRT
<213> ORGANISM: Artificial
<220> FEATURE:
<223> OTHER INFORMATION: Synthetic

<400> SEQUENCE: 126

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
                20                  25                  30

Lys Phe Glu Ser Asn Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

<210> SEQ ID NO 127
<211> LENGTH: 360
<212> TYPE: PRT
<213> ORGANISM: Artificial
<220> FEATURE:
<223> OTHER INFORMATION: Synthetic

<400> SEQUENCE: 127

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
```

```
65               70                75               80

Leu Gln Met Asn Ser Leu Arg Ala Glu Asp Thr Ala Val Tyr Tyr Cys
                85               90               95

Ala Lys Val Ser Tyr Leu Ser Thr Ala Ser Ser Leu Asp Tyr Trp Gly
            100              105              110

Gln Gly Thr Leu Val Thr Val Ser Ser Ala Ser Thr Lys Gly Pro Ser
        115              120              125

Val Phe Pro Leu Ala Pro Ser Ser Lys Ser Thr Ser Gly Gly Thr Ala
    130              135              140

Ala Leu Gly Cys Leu Val Lys Asp Tyr Phe Pro Glu Pro Val Thr Val
145              150              155              160

Ser Trp Asn Ser Gly Ala Leu Thr Ser Gly Val His Thr Phe Pro Ala
                165              170              175

Val Leu Gln Ser Ser Gly Leu Tyr Ser Leu Ser Ser Val Val Thr Val
            180              185              190

Pro Ser Ser Ser Leu Gly Thr Gln Thr Tyr Ile Cys Asn Val Asn His
        195              200              205

Lys Pro Ser Asn Thr Lys Val Asp Lys Lys Val Glu Pro Lys Ser Cys
    210              215              220

Asp Lys Thr His Thr Cys Pro Pro Cys Pro Ala Pro Glu Leu Leu Gly
225              230              235              240

Gly Pro Ser Val Phe Leu Phe Pro Pro Lys Pro Lys Asp Thr Leu Met
                245              250              255

Ile Ser Arg Thr Pro Glu Val Thr Cys Val Val Val Asp Val Ser His
            260              265              270

Glu Asp Pro Glu Val Lys Phe Asn Trp Tyr Val Asp Gly Val Glu Val
        275              280              285

His Asn Ala Lys Thr Lys Pro Arg Glu Glu Gln Tyr Asn Ser Thr Tyr
    290              295              300

Arg Val Val Ser Val Leu Thr Val Leu His Gln Asp Trp Leu Asn Gly
305              310              315              320

Lys Glu Tyr Lys Cys Lys Val Ser Asn Lys Ala Leu Pro Ala Pro Ile
                325              330              335

Glu Lys Thr Ile Ser Lys Ala Lys Gly Gln Pro Arg Glu Pro Gln Val
            340              345              350

Tyr Thr Leu Pro Pro Ser Arg Asp
        355              360

<210> SEQ ID NO 128
<211> LENGTH: 305
<212> TYPE: PRT
<213> ORGANISM: Artificial
<220> FEATURE:
<223> OTHER INFORMATION: Synthetic

<400> SEQUENCE: 128

Asp Ile Gln Met Thr Gln Ser Pro Ser Ser Leu Ser Ala Ser Val Gly
1               5                10               15

Asp Arg Val Thr Ile Thr Cys Arg Ala Ser Gln Gly Ile Arg Asn Tyr
            20               25               30

Leu Ala Trp Tyr Gln Gln Lys Pro Gly Lys Ala Pro Lys Leu Leu Ile
        35               40               45

Tyr Ala Ala Ser Thr Leu Gln Ser Gly Val Pro Ser Arg Phe Ser Gly
    50               55               60

Ser Gly Ser Gly Thr Asp Phe Thr Leu Thr Ile Ser Ser Leu Gln Pro
```

```
65                    70                    75                    80
Glu Asp Val Ala Thr Tyr Tyr Cys Gln Arg Tyr Asn Arg Ala Pro Tyr
                    85                    90                    95

Thr Phe Gly Gln Gly Thr Lys Val Glu Ile Lys Arg Thr Val Ala Ala
                    100                   105                   110

Pro Ser Val Phe Ile Phe Pro Pro Ser Asp Glu Gln Leu Lys Ser Gly
                    115                   120                   125

Thr Ala Ser Val Val Cys Leu Leu Asn Asn Phe Tyr Pro Arg Glu Ala
    130                   135                   140

Lys Val Gln Trp Lys Val Asp Asn Ala Leu Gln Ser Gly Asn Ser Gln
145                   150                   155                   160

Glu Ser Val Thr Glu Gln Asp Ser Lys Asp Ser Thr Tyr Ser Leu Ser
                    165                   170                   175

Ser Thr Leu Thr Leu Ser Lys Ala Asp Tyr Glu Lys His Lys Val Tyr
                    180                   185                   190

Ala Cys Glu Val Thr His Gln Gly Leu Ser Ser Pro Val Thr Lys Ser
                    195                   200                   205

Phe Asn Arg Gly Glu Cys Glu Leu Thr Lys Asn Gln Val Ser Leu Thr
    210                   215                   220

Cys Leu Val Lys Gly Phe Tyr Pro Ser Asp Ile Ala Val Glu Trp Glu
225                   230                   235                   240

Ser Asn Gly Gln Pro Glu Asn Asn Tyr Lys Thr Thr Pro Pro Val Leu
                    245                   250                   255

Asp Ser Asp Gly Ser Phe Phe Leu Tyr Ser Lys Leu Thr Val Asp Lys
                    260                   265                   270

Ser Arg Trp Gln Gln Gly Asn Val Phe Ser Cys Ser Val Met His Glu
                    275                   280                   285

Ala Leu His Asn His Tyr Thr Gln Lys Ser Leu Ser Leu Ser Pro Gly
                    290                   295                   300

Lys
305

<210> SEQ ID NO 129
<211> LENGTH: 448
<212> TYPE: PRT
<213> ORGANISM: Artificial
<220> FEATURE:
<223> OTHER INFORMATION: Synthetic

<400> SEQUENCE: 129

Gln Val Gln Leu Val Glu Ser Gly Gly Gly Val Val Gln Pro Gly Arg
1                   5                     10                    15

Ser Leu Arg Leu Ser Cys Ala Ala Ser Gly Phe Thr Phe Ser Ser Tyr
                    20                    25                    30

Thr Met His Trp Val Arg Gln Ala Pro Gly Lys Gly Leu Glu Trp Val
                    35                    40                    45

Thr Phe Ile Ser Tyr Asp Gly Asn Asn Lys Tyr Tyr Ala Asp Ser Val
                    50                    55                    60

Lys Gly Arg Phe Thr Ile Ser Arg Asp Asn Ser Lys Asn Thr Leu Tyr
65                    70                    75                    80

Leu Gln Met Asn Ser Leu Arg Ala Glu Asp Thr Ala Ile Tyr Tyr Cys
                    85                    90                    95

Ala Arg Thr Gly Trp Leu Gly Pro Phe Asp Tyr Trp Gly Gln Gly Thr
                    100                   105                   110

Leu Val Thr Val Ser Ser Ala Ser Thr Lys Gly Pro Ser Val Phe Pro
```

-continued

```
              115                 120                 125
Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
                275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
                355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
                435                 440                 445
```

<210> SEQ ID NO 130
<211> LENGTH: 215
<212> TYPE: PRT
<213> ORGANISM: Artificial
<220> FEATURE:
<223> OTHER INFORMATION: Synthetic

<400> SEQUENCE: 130

```
Glu Ile Val Leu Thr Gln Ser Pro Gly Thr Leu Ser Leu Ser Pro Gly
1                   5                   10                  15

Glu Arg Ala Thr Leu Ser Cys Arg Ala Ser Gln Ser Val Gly Ser Ser
                20                  25                  30

Tyr Leu Ala Trp Tyr Gln Gln Lys Pro Gly Gln Ala Pro Arg Leu Leu
```

```
            35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
                115                 120                 125

Gly Thr Ala Ser Val Val Cys Leu Leu Asn Asn Phe Tyr Pro Arg Glu
                130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
    210                 215

<210> SEQ ID NO 131
<211> LENGTH: 360
<212> TYPE: PRT
<213> ORGANISM: Artificial
<220> FEATURE:
<223> OTHER INFORMATION: Synthetic
<220> FEATURE:
<221> NAME/KEY: X1
<222> LOCATION: (80)..(80)
<223> OTHER INFORMATION: X1 is selected from D, H, N, S, Y, A, F, and T
<220> FEATURE:
<221> NAME/KEY: X2
<222> LOCATION: (82)..(82)
<223> OTHER INFORMATION: X2 is selected from E, and Q
<220> FEATURE:
<221> NAME/KEY: X3
<222> LOCATION: (85)..(85)
<223> OTHER INFORMATION: X3 is selected from D, G, and S
<220> FEATURE:
<221> NAME/KEY: X4
<222> LOCATION: (87)..(87)
<223> OTHER INFORMATION: X4 is selected from A, G, R, S, and T
<220> FEATURE:
<221> NAME/KEY: X5
<222> LOCATION: (88)..(88)
<223> OTHER INFORMATION: X5 is selected from A, D, E, N, P, T and K

<400> SEQUENCE: 131

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Xaa
65                  70                  75                  80
```

-continued

```
Leu Xaa Met Asn Xaa Leu Xaa Xaa Glu Asp Thr Ala Val Tyr Tyr Cys
            85              90              95

Ala Lys Val Ser Tyr Leu Ser Thr Ala Ser Ser Leu Asp Tyr Trp Gly
            100             105             110

Gln Gly Thr Leu Val Thr Val Ser Ser Ala Ser Thr Lys Gly Pro Ser
            115             120             125

Val Phe Pro Leu Ala Pro Ser Ser Lys Ser Thr Ser Gly Gly Thr Ala
    130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
            165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
            195             200             205

Lys Pro Ser Asn Thr Lys Val Asp Lys Lys Val Glu Pro Lys Ser Cys
    210             215             220

Asp Lys Thr His Thr Cys Pro Pro Cys Pro Ala Pro Glu Leu Leu Gly
225             230             235             240

Gly Pro Ser Val Phe Leu Phe Pro Pro Lys Pro Lys Asp Thr Leu Met
            245             250             255

Ile Ser Arg Thr Pro Glu Val Thr Cys Val Val Val Asp Val Ser His
            260             265             270

Glu Asp Pro Glu Val Lys Phe Asn Trp Tyr Val Asp Gly Val Glu Val
            275             280             285

His Asn Ala Lys Thr Lys Pro Arg Glu Glu Gln Tyr Asn Ser Thr Tyr
    290             295             300

Arg Val Val Ser Val Leu Thr Val Leu His Gln Asp Trp Leu Asn Gly
305             310             315             320

Lys Glu Tyr Lys Cys Lys Val Ser Asn Lys Ala Leu Pro Ala Pro Ile
            325             330             335

Glu Lys Thr Ile Ser Lys Ala Lys Gly Gln Pro Arg Glu Pro Gln Val
            340             345             350

Tyr Thr Leu Pro Pro Ser Arg Asp
            355             360
```

```
<210> SEQ ID NO 132
<211> LENGTH: 360
<212> TYPE: PRT
<213> ORGANISM: Artificial
<220> FEATURE:
<223> OTHER INFORMATION: Synthetic
<220> FEATURE:
<221> NAME/KEY: X12
<222> LOCATION: (99)..(99)
<223> OTHER INFORMATION: X12 is selected from D, E, and V
<220> FEATURE:
<221> NAME/KEY: X13
<222> LOCATION: (101)..(101)
<223> OTHER INFORMATION: X13 is selected from D, E, G, N, Q, T, V, W, F,
      L, and Y
<220> FEATURE:
<221> NAME/KEY: X14
<222> LOCATION: (102)..(102)
<223> OTHER INFORMATION: X14 is selected from A, E, H, L, N, P, Q, S, T,
      V, and W
<220> FEATURE:
<221> NAME/KEY: X15
<222> LOCATION: (103)..(103)
```

-continued

```
<223> OTHER INFORMATION: X15 is selected from E, S, and G
<220> FEATURE:
<221> NAME/KEY: X16
<222> LOCATION: (104)..(104)
<223> OTHER INFORMATION: X16 is selected from E, G, H, K, P, R, and T
<220> FEATURE:
<221> NAME/KEY: X17
<222> LOCATION: (105)..(105)
<223> OTHER INFORMATION: X17 is selected from A, S, and G
<220> FEATURE:
<221> NAME/KEY: X18
<222> LOCATION: (106)..(106)
<223> OTHER INFORMATION: X18 is selected from E, S, G, and D
<220> FEATURE:
<221> NAME/KEY: X19
<222> LOCATION: (107)..(107)
<223> OTHER INFORMATION: X19 is selected from D, N, G, and S

<400> SEQUENCE: 132

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30

Ala Met His Trp Val Arg Gln Ala Pro Gly Lys Gly Leu Glu Trp Val
            35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Xaa Ser Xaa Xaa Xaa Xaa Xaa Xaa Xaa Leu Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320
```

-continued

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp
        355                 360

<210> SEQ ID NO 133
<211> LENGTH: 360
<212> TYPE: PRT
<213> ORGANISM: Artificial
<220> FEATURE:
<223> OTHER INFORMATION: Synthetic
<220> FEATURE:
<221> NAME/KEY: X1
<222> LOCATION: (80)..(80)
<223> OTHER INFORMATION: X1 is selected from D, H, N, S, Y, A, F, and T
<220> FEATURE:
<221> NAME/KEY: X2
<222> LOCATION: (82)..(82)
<223> OTHER INFORMATION: X2 is selected from E, and Q
<220> FEATURE:
<221> NAME/KEY: X3
<222> LOCATION: (85)..(85)
<223> OTHER INFORMATION: X3 is selected from D, G, and S
<220> FEATURE:
<221> NAME/KEY: X4
<222> LOCATION: (87)..(87)
<223> OTHER INFORMATION: X4 is selected from A, G, R, S, and T
<220> FEATURE:
<221> NAME/KEY: X5
<222> LOCATION: (88)..(88)
<223> OTHER INFORMATION: X5 is selected from A, D, E, N, P, T and K
<220> FEATURE:
<221> NAME/KEY: X12
<222> LOCATION: (99)..(99)
<223> OTHER INFORMATION: X12 is selected from D, E, and V
<220> FEATURE:
<221> NAME/KEY: X13
<222> LOCATION: (101)..(101)
<223> OTHER INFORMATION: X13 is selected from D, E, G, N, Q, T, V, W, F,
      L, and Y
<220> FEATURE:
<221> NAME/KEY: X14
<222> LOCATION: (102)..(102)
<223> OTHER INFORMATION: X14 is selected from A, E, H, L, N, P, Q, S, T,
      V, and W
<220> FEATURE:
<221> NAME/KEY: X15
<222> LOCATION: (103)..(103)
<223> OTHER INFORMATION: X15 is selected from E, S, and G
<220> FEATURE:
<221> NAME/KEY: X16
<222> LOCATION: (104)..(104)
<223> OTHER INFORMATION: X16 is selected from E, G, H, K, P, R, and T
<220> FEATURE:
<221> NAME/KEY: X17
<222> LOCATION: (105)..(105)
<223> OTHER INFORMATION: X17 is selected from A, S, and G
<220> FEATURE:
<221> NAME/KEY: X18
<222> LOCATION: (106)..(106)
<223> OTHER INFORMATION: X18 is selected from E, S, G, and D
<220> FEATURE:
<221> NAME/KEY: X19
<222> LOCATION: (107)..(107)
<223> OTHER INFORMATION: X19 is selected from D, N, G, and S

<400> SEQUENCE: 133

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
                20                  25                  30
```

```
Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
        50                  55                  60

Glu Gly Arg Phe Thr Ile Ser Arg Asp Asn Ala Lys Asn Ser Leu Xaa
65                  70                  75                  80

Leu Xaa Met Asn Xaa Leu Xaa Xaa Glu Asp Thr Ala Val Tyr Tyr Cys
        85                  90                  95

Ala Lys Xaa Ser Xaa Xaa Xaa Xaa Xaa Xaa Leu Asp Tyr Trp Gly
        100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
        165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
        245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
        325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp
        355                 360
```

```
<210> SEQ ID NO 134
<211> LENGTH: 448
<212> TYPE: PRT
<213> ORGANISM: Artificial
<220> FEATURE:
<223> OTHER INFORMATION: Synthetic
<220> FEATURE:
<221> NAME/KEY: X1
<222> LOCATION: (80)..(80)
<223> OTHER INFORMATION: X1 is selected from D, H, N, S, Y, A, F, and T
<220> FEATURE:
<221> NAME/KEY: X2
<222> LOCATION: (82)..(82)
<223> OTHER INFORMATION: X2 is selected from E, and Q
```

```
<220> FEATURE:
<221> NAME/KEY: X3
<222> LOCATION: (85)..(85)
<223> OTHER INFORMATION: X3 is selected from D, G, and S
<220> FEATURE:
<221> NAME/KEY: X4
<222> LOCATION: (87)..(87)
<223> OTHER INFORMATION: X4 is selected from A, G, R, S, and T
<220> FEATURE:
<221> NAME/KEY: X5
<222> LOCATION: (88)..(88)
<223> OTHER INFORMATION: X5 is selected from A, D, E, N, P, T and K

<400> SEQUENCE: 134

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Xaa
65                  70                  75                  80

Leu Xaa Met Asn Xaa Leu Xaa Xaa Glu Asp Thr Ala Ile Tyr Tyr Cys
            85                  90                  95

Ala Arg Thr Gly Trp Leu Gly Pro Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
```

-continued

```
              340                 345                 350
Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

1

ANTIBODIES WITH REDUCED IMMUNOGENICITY

CROSS REFERENCE TO RELATED APPLICATIONS

This application is a Bypass Continuation of PCT Patent Application No. PCT/IL2020/050772 having International filing date of Jul. 9, 2020, which claims the benefit of priority of U.S. Provisional Patent Application No. 62/871, 856, filed Jul. 9, 2019. The contents of the above applications are all incorporated herein by reference as if fully set forth herein in their entirety.

FIELD OF INVENTION

The present invention is in the field of antibody engineering.

BACKGROUND OF THE INVENTION

The use of therapeutic antibodies for the treatment of a wide variety of conditions has been well established, with hundreds of therapeutic antibodies targeting dozens or targets already approved for human use. Antibodies with cytotoxic effects, blocking effects, activating effects and more are known and well characterized. However, many therapeutic antibodies elicit an immune response in patients to whom they are administered.

Foreign proteins that have an amino acid sequence dissimilar to human sequences are recognized by the immune system as pathogens. This results in the production of anti-drug antibodies (ADAs) which bind to the foreign proteins and target them for degradation. When the foreign protein is a therapeutic, the ADAs can block the functionality of the therapeutic molecule, reduce the circulating half-life and lead to elimination of the therapeutic from the subject before the therapeutic effect can be achieved. Generally, the ADA response severely reduces the therapeutic efficacy of the molecule.

Many well-known and well characterized antibodies are known to induce ADAs. Depending on the study examined, it has been reported that 9-89% of patients treated with Humira develop ADAs. For the anti-CTLA antibody, Ipilimumab, has been reported to produce ADAs in about 25% of patients. One possible method for reducing ADAs would be to reduce the immunogenicity of the therapeutic molecule, however, methods of designing therapeutics, and specifically antibodies, with reduced immunogenicity are greatly needed.

SUMMARY OF THE INVENTION

The present invention provides methods producing a second antibody from a first and methods of reducing the immunogenicity of an antibody. Polypeptides, antibodies and antigen binding fragments comprising non-immunogenic or lowly-immunogenic sequences are also provided.

According to a first aspect, there is provided an antibody or antigen binding fragment thereof comprising three heavy chain CDRs (CDR-H) and three light chain CDRs (CDR-L), wherein:

CDR-H1 comprises the amino acid sequence set forth in SEQ ID NO: 114 (DYAMH), CDR-H2 comprises the amino acid sequence as set forth in SEQ ID NO: 115 (AITW), CDR-H3 comprises the amino acid sequence as set forth in SEQ ID NO: 116 $(X_{12}SX_{13}X_{14}X_{15}X_{16}X_{17}X_{18}X_{19}LDX_{30})$ and does not comprise SEQ ID NO: 6, CDR-L1 comprises the amino acid sequence as set forth in SEQ ID NO: 117 (RASQGIRNYLA), CDR-L2 comprises the amino acid sequence as set forth in SEQ ID NO: 118 (AASTLQS), and CDR-L3 comprises the amino acid sequence as set forth in SEQ ID NO: 119 (QRYNRAPYX$_{31}$), wherein $X_{12}$ is selected from D, E, and V, $X_{13}$ is selected from D, E, G, N, Q, T, V, W, F, L, and Y, $X_{14}$ is selected from A, E, H, L, N, P, Q, S, T, V, and W, $X_{15}$ is selected from E, S, and G, $X_{16}$ is selected from E, G, H, K, P, R, and T, $X_{17}$ is selected from A, S, and G, $X_{18}$ is selected from E, S, G, and D, $X_{19}$ is selected from D, N, G, and S, $X_{30}$ is selected from Y and N, $X_{31}$ is selected from T and A.

According to another aspect, there is provided an antibody or antigen binding fragment comprising a heavy chain comprising SEQ ID NO: 133 and not comprising SEQ ID NO: 1.

According to another aspect, there is provided an antibody or antigen binding fragment comprising a heavy chain comprising SEQ ID NO: 134 and not comprising SEQ ID NO: 1.

According to some embodiments, the CDR-L3 consists of SEQ ID NO: 120 (QRYNRAPYT).

According to some embodiments, the CDR-H3 comprises SEQ ID NO: 121 ($X_{12}SX_{13}X_{14}X_{15}X_{16}X_{17}X_{18}X_{19}LDY$).

According to some embodiments, the wherein SEQ ID NO: 116 comprises $X_{12}SX_{20}X_{21}X_{15}X_{16}X_{22}X_{23}X_{24}LD\ X_{31}$ (SEQ ID NO: 122), wherein $X_{12}$ is selected from D, E, and V, $X_{20}$ is selected from D, E, G, N, Q, T, V, W, and Y, $X_{21}$ is selected from A, E, H, L, N, P, Q, S, T, and W, $X_{15}$ is selected from E, S, and G, $X_{16}$ is selected from E, G, H, K, P, R, and T, $X_{22}$ is selected from A, and G, $X_{23}$ is selected from E, S, and D, $X_{24}$ is selected from D, and S, and $X_{31}$ is selected from T and A.

According to some embodiments, SEQ ID NO: 116 comprises $VSX_{25}X_{26}STX_{27}X_{28}X_{29}LDX_{31}$ (SEQ ID NO: 123), wherein $X_{25}$ is selected from W, Y, G, Q, F, L, and V, $X_{26}$ is selected L, V, H, and P, $X_{27}$ is selected from A, and S, $X_{28}$ is selected from E, S, and G, $X_{29}$ is selected from N, S, D, and G, $X_{31}$ is selected from T and A.

According to some embodiments, SEQ ID NO: 116 comprises an amino acid sequence selected from SEQ ID NO: 97-112.

According to some embodiments, the antibody or antigen binding fragment of the invention further comprises LX1LX2MNX3LX4X5 (SEQ ID NO: 2) between the CDR-H2 and CDR-H3.

According to some embodiments, the SEQ ID NO: 2 does not comprise LYLQMNSLRA (SEQ ID NO: 1).

According to some embodiments, the SEQ ID NO: 2 comprises SEQ ID NO: 3, SEQ ID NO: 4, or SEQ ID NO: 5.

According to some embodiments, the SEQ ID NO: 2 consists of a sequence selected from SEQ ID NO: 10-26, 37-96 and 113.

According to some embodiments, the heavy chain comprises a sequence selected from SEQ ID NO: 132 and 133.

According to some embodiments, the antibody or antigen binding fragment comprises a light chain comprising SEQ ID NO: 128.

According to some embodiments, the heavy chain comprises SEQ ID NO: 131.

According to some embodiments, the SEQ ID NO: 133 comprises SEQ ID NO: 3, SEQ ID NO: 4, or SEQ ID NO: 5 from amino acids 79-88.

According to some embodiments, the SEQ ID NO: 133 comprises a sequence selected from SEQ ID NO: 10-26, 37-96 and 113 at amino acids 79-88.

According to some embodiments, the antibody or antigen binding fragment binds Tumor Necrosis Factor Alpha (TNFa).

According to some embodiments, the antibody or antigen binding fragment comprises a light chain comprising SEQ ID NO: 130.

According to some embodiments, the SEQ ID NO: 134 comprises SEQ ID NO: 3, SEQ ID NO: 4, or SEQ ID NO: 5 from amino acids 79-88.

According to some embodiments, the SEQ ID NO: 134 comprises a sequence selected from SEQ ID NO: 10-26, 37-96 and 113 at amino acids 79-88.

According to some embodiments, the antibody or antigen binding fragment binds Cytotoxic T-Lymphocyte-Associated protein 4 (CTLA4).

According to another aspect, there is provided a polypeptide comprising SEQ ID NO: 2, wherein the SEQ ID NO: 2 does not comprise any of SEQ ID NO: 1, SEQ ID NO: 12, SEQ ID NO: 38, SEQ ID NO: 60, SEQ ID NO: 71 and SEQ ID NO: 94.

According to another aspect, there is provide an antibody or antigen binding domain comprising a polypeptide of the invention.

According to another aspect, there is provide an antibody or antigen binding domain comprising a polypeptide comprising SEQ ID NO: 2, wherein the SEQ ID NO: 2 does not comprise SEQ ID NO: 1 and does not comprise SEQ ID NO: 12.

According to another aspect, there is provided a pharmaceutical composition comprising a polypeptide of the invention or the antibody or antigen binding fragment of the invention and a pharmaceutically acceptable carrier, excipient or adjuvant.

According to some embodiments, the polypeptide is non-immunogenic in humans.

According to some embodiments, the SEQ ID NO: 2 is SEQ ID NO: 3.

According to some embodiments, the SEQ ID NO: 2 is SEQ ID NO: 4.

According to some embodiments, the SEQ ID NO: 2 is SEQ ID NO: 5.

According to some embodiments, the SEQ ID NO: 2 consists of a sequence selected from SEQ ID NO: 10-11, 13-26, 37, 39-59, 61-70, 72-93, 95-96 and 113.

According to some embodiments, the SEQ ID NO: 2 consists of a sequence selected from SEQ ID NO: 10-11, 13-26, 37, 39-59, 61-70, 72-93, 95-96 and 113.

According to some embodiments, a heavy chain of the antibody or antigen binding fragment thereof comprises SEQ ID NO: 2.

According to some embodiments, amino acids 79-88 of the heavy chain are SEQ ID NO: 2.

According to another aspect, there is provided a method for producing a second antibody from a first antibody, the method comprising:

a. providing a first nucleic acid molecule comprising a coding sequence which encodes an amino acid sequence of the first antibody, wherein the amino acid sequence comprises LYLQMNSLRA (SEQ ID NO: 1), b. providing a second nucleic acid molecule encoding an amino acid sequence of a second antibody, wherein the amino acid sequence comprises $LX_1LX_2MNX_3LX_4X_5$ (SEQ ID NO: 2) in place of SEQ ID NO: 1, wherein:
$X_1$ is selected from D, H, N, S, Y, A, F, and T,
$X_2$ is selected from E, and Q,
$X_3$ is selected from D, G, and S,
$X_4$ is selected from A, G, R, S, and T,
$X_5$ is selected from A, D, E, N, P, T and K,
wherein the SEQ ID NO: 1 and SEQ ID NO: 2 comprise a different amino acid sequence;

c. producing a second antibody from the second nucleic acid molecule;

thereby producing a second antibody.

According to some embodiments, the producing the second antibody comprises reducing the immunogenicity of the first antibody.

According to some embodiments, a heavy chain of the first antibody comprises SEQ ID NO: 1.

According to some embodiments, SEQ ID NO: 1 is amino acids 79-88 of the heavy chain of the first antibody.

According to some embodiments, the SEQ ID NO: 2 consists of a sequence selected from SEQ ID NO: 10-26, 37-96 and 113.

According to some embodiments, the method of the invention further comprises confirming binding of the second antibody to a target or an epitope of the first antibody.

According to some embodiments, the confirmed binding comprises measuring a binding value of the second antibody to the target or epitope by a binding assay and confirming the binding value of the second antibody is at least 70% of a binding value of the first antibody to the target or epitope.

According to some embodiments, the first antibody is selected from Table 2.

According to some embodiments, the first antibody is selected from the group consisting of: afasevikumab, adalimumab, sutimlimab, remtolumab, terextumab, elotuzumab, bimekizumab, sofituzumab vedotin, rozanolixizumab, lanadelumab, suvratoxumab, gosuranemab, ipilimumab, dupliumab, efalizumab, frovocimab, emapalumab, alirocumab, inclacumab, crotedumab, avelumab, opicinumab, emicizumab, durvalumab, solanexumab, ramucirumab, tovetumab, pertuzumab, suptavumab, nesvacumab, quilizumab, brazikumab, denosumab, varlilumab, tremelimumab, igatuzumab, robatumumab, prezalumab, prasinezumab, panobacumab, otilimab, otelixizumab, osocimab, lorvotuzumab mertansine, lexatumumab, icrucumab, fremanexumab, elgemtumab, daratumumb, corncizumab, bapineuzumab, and anrukinzumab.

According to some embodiments, the first antibody is adalimumab or ipilimumab.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 7A-7E: (7A) Line graphs of predicted immunogenicity of representative peptides from Library 1 inserted into Ipilimumab. WT Ipilimumab was used as control. (7B) Histograms of CTLA4 binding to antibodies containing peptides from Library 1 as well as WT Ipilimumab as a control. CTLA4 concentration is 20 nM and WT Ipilimumab control is colored light blue. (7C-7D) Heat maps of (7C) binding of selected peptides as part of Ipilimumab to six HLA alleles and (7D) the fold decrease in IC50 of selected peptides for the six HLA alleles. (7E) Shared epitope in selected sequences from Library 1 inserted into Ipilimumab.

DETAILED DESCRIPTION OF THE INVENTION

Figure 1A:
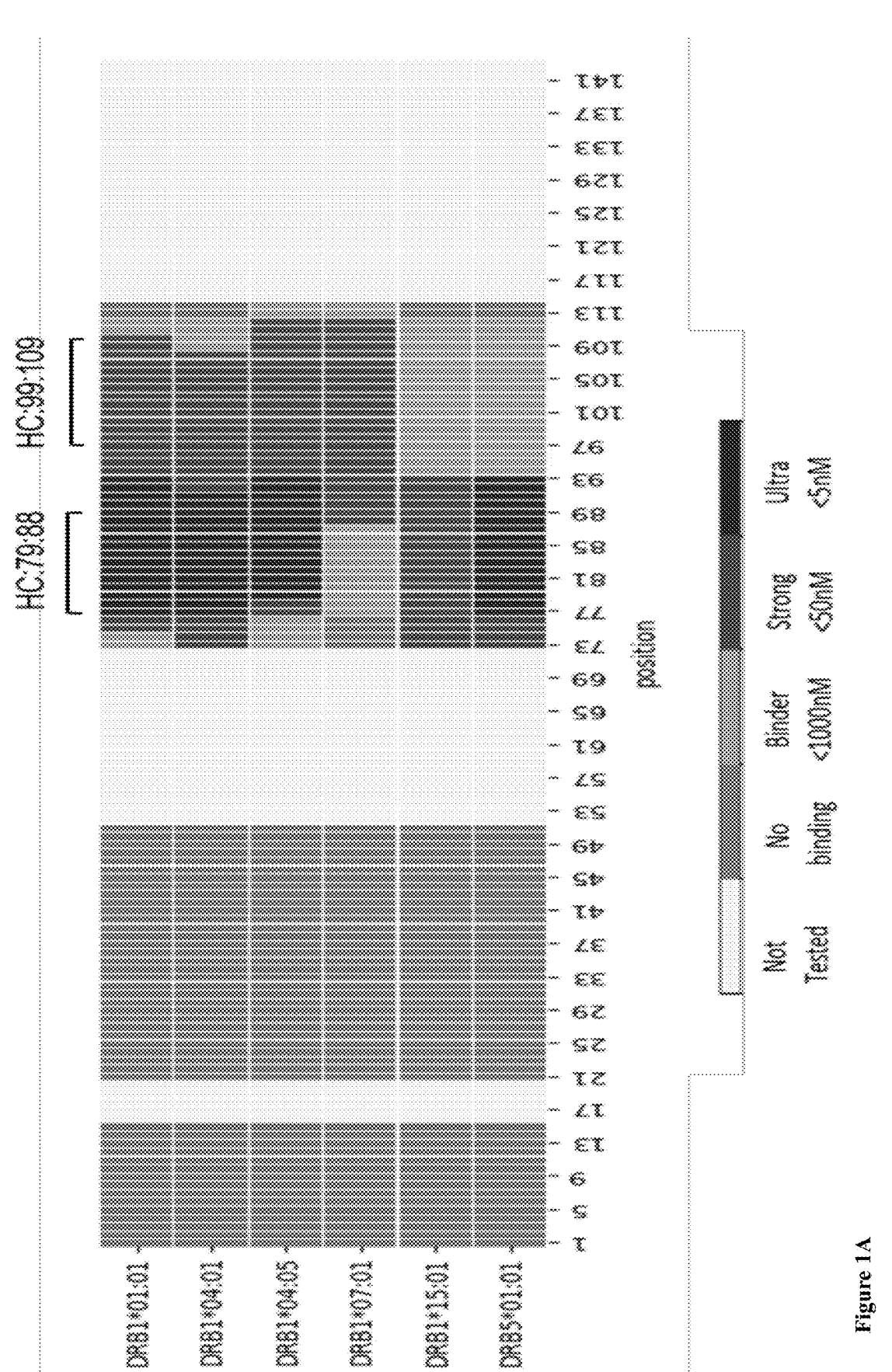
FIGS. 1A-1C: (1A) A heatmap analyzing the binding affinity between HLA alleles and potential hotspot peptides. Each position (x-axis) in the Humira VH sequences was colored according to its occurrence within: Peptides that were not tested for HLA binding (white). Peptides that did not present binding towards the tested HLA allele, IC50>1000 nM (gray). Binder peptides with 1000 nM>IC50>50 nM (pink). Peptides displaying strong binding 50 nM>IC50>5 nM (red) and Ultra peptides that tightly bind the JLA with IC50<5 nM (dark red). Residues that were within peptides from two or more categorized were defined according to the peptide with the lowest IC50. Each tested allele is represented by single raw. (1B-1C) Graphs of immune-score, epitope numbers and 9-mer similarity to self across the (1B) light chain and (1C) heavy chain of Humira.

The present invention, in some embodiments, provides methods of reducing the immunogenicity of an antibody comprising the amino acid sequence LYLQMNSLRA and/or VSYLSTASSLD. Polypeptides, antibodies and antigen binding fragments comprising non-immunogenic and/or lowly immunogenic sequences are also provided.

By a first aspect, there is provided a polypeptide comprising the amino acid sequence $LX_1LX_2MNX_3LX_4X_5$ (SEQ ID NO: 2), wherein $X_1$ is selected from D, H, N, S, Y, A, F, and T; $X_2$ is selected from E, and Q; $X_3$ is selected from D, G, and S; $X_4$ is selected from A, G, R, S, and T; $X_5$ is selected from A, D, E, N, P, T and K.

In some embodiments, SEQ ID NO: 2 does not comprise the amino acid sequence LYLQMNSLRA (SEQ ID NO: 1). As used herein, the terms "does not comprise" and "is devoid of" are synonymous and used interchangeably. In some embodiments, SEQ ID NO: 1 and SEQ ID NO: 2 comprise a different amino acid sequence. In some embodiments, SEQ ID NO: 1 and SEQ ID NO: 2 are not identical. In some embodiments, SEQ ID NO: 2 does not comprise SEQ ID NO: 12. In some embodiments, SEQ ID NO: 2 does not comprise SEQ ID NO: 38. In some embodiments, SEQ ID NO: 2 does not comprise SEQ ID NO: 58. In some embodiments, SEQ ID NO: 2 does not comprise SEQ ID NO: 60. In some embodiments, SEQ ID NO: 2 does not comprise SEQ ID NO: 71. In some embodiments, SEQ ID NO: 2 does not comprise SEQ ID NO: 94. In some embodiments, SEQ ID NO: 2 does not comprise a sequence selected from SEQ ID NO: 1, SEQ ID NO: 12, SEQ ID NO: 38, SEQ ID NO: 60, SEQ ID NO: 71 and SEQ ID NO: 94. In some embodiments, SEQ ID NO: 2 does not comprises SEQ ID NO: 1, SEQ ID NO: 12, SEQ ID NO: 38, SEQ ID NO: 60, SEQ ID NO: 71 and SEQ ID NO: 94. In some embodiments, SEQ ID NO: 2 does not comprises any of SEQ ID NO: 1, SEQ ID NO: 12, SEQ ID NO: 38, SEQ ID NO: 60, SEQ ID NO: 71 and SEQ ID NO: 94. In some embodiments, SEQ ID NO: 2 is devoid of SEQ ID NO: 1, SEQ ID NO: 12, SEQ ID NO: 38, SEQ ID NO: 60, SEQ ID NO: 71 and SEQ ID NO: 94. In some embodiments, SEQ ID NO: 2 is devoid of all of SEQ ID NO: 1, SEQ ID NO: 12, SEQ ID NO: 38, SEQ ID NO: 60, SEQ ID NO: 71 and SEQ ID NO: 94.

In some embodiments, the polypeptide comprises at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490 or 500 amino acids. Each possibility represents a separate embodiment of the invention. In some embodiments, the polypeptide comprises at least 120 amino acids. In some embodiments, the polypeptide comprises at least 220 amino acids. In some embodiments, the polypeptide comprises at least 330 amino acids. In some embodiments, the polypeptide comprises at least 440 amino acids. In some embodiments, the polypeptide comprises at most 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 550, 600, 650, 700, 750, 800, 850, 900, 950, or 1000 amino acids. Each possibility represents a separate embodiment of the invention. In some embodiments, the polypeptide comprises at most 130 amino acids. In some embodiments, the polypeptide comprises at most 230 amino acids. In some embodiments, the polypeptide comprises at most 450 amino acids. In some embodiments, the polypeptide comprises at most 500 amino acids.

In some embodiments, the polypeptide is or is comprises in a therapeutic. In some embodiments, the polypeptide is or is comprises in a drug. In some embodiments, the polypeptide, therapeutic or drug is suitable to be administered to a subject. In some embodiments, the polypeptide therapeutic or drug is formulated for administration to a subject. In some embodiments, the subject is a mammal. In some embodiments, the subject is a human. In some embodiments, the administration is systemic administration. In some embodiments, the polypeptide is a non-immunogenic peptide. In some embodiments, the polypeptide is a low-immunogenic peptide. In some embodiments, the polypeptide does not induce an immune response in a subject. In some embodiments, the polypeptide produces a reduced immune response in a subject as compared to a polypeptide comprising SEQ ID NO: 1. In some embodiments, therapeutic is an antibody. In some embodiments, the therapeutic is an antigen binding domain.

In some embodiments, the antibody or antigen binding domain comprises the polypeptide. In some embodiments, a heavy chain of the antibody or antigen binding fragment comprises SEQ ID NO: 2. In some embodiments, SEQ ID NO: 2 is amino acids 79-88 of the heavy chain of the antibody or antigen binding fragment.

In some embodiments, the antibody is adalimumab (Humira). In some embodiments, the antibody comprises the amino acid sequence of adalimumab wherein amino acids 79-88 of the heavy chain of adalimumab have been replaced by SEQ ID NO: 2. In some embodiments, the antibody is ipilimumab (Yervoy). In some embodiments, the antibody comprises the amino acid sequence of ipilimumab wherein amino acids 79-88 of the heavy chain of adalimumab have been replaced by SEQ ID NO: 2.

In some embodiments, SEQ ID NO: 2 comprises the amino acid sequence $LX_6LX_2MNX_3LX_4X_7$ (SEQ ID NO: 3), wherein $X_6$ is selected from N, S, Y, A, and H, $X_2$ is selected from E, and Q, $X_3$ is selected from D, G, and S, $X_4$ is selected from A, G, R, S, and T, and $X_7$ is selected from E, P, T, and A. In some embodiments, SEQ ID NO: 2 consists of SEQ ID NO: 3. In some embodiments, SEQ ID NO: 2 comprises the amino acid sequence $LX_8LX_2MNX_3LX_4X_9$ (SEQ ID NO: 4), wherein $X_8$ is selected from N, S, Y, D, and H, $X_2$ is selected from E, and Q, $X_3$ is selected from D, G, and S, $X_4$ is selected from A, G, R, S, and T, and $X_9$ is selected from D, E, P, N, and A. In some embodiments, SEQ ID NO: 2 consists of SEQ ID NO: 4. In some embodiments, SEQ ID NO: 2 comprises the amino acid sequence $LX_{10}LX_2MNX_3LX_4X_{11}$ (SEQ ID NO: 5), wherein $X_{10}$ is selected from T, D, and Y, $X_2$ is selected from E, and Q, $X_3$ is selected from D, G, and S, $X_4$ is selected from A, G, R, S, and T, and $X_{11}$ is selected from E, P, and D. In some embodiments, SEQ ID NO: 2 consists of SEQ ID NO: 5.

In some embodiments, the heavy chain of the antibody or antigen binding fragment is selected from Table 1. In some embodiments, the heavy chain of the antibody or antigen binding fragment is selected from SEQ ID NO: 27-36.

TABLE 1

| VH1 | EVQLVESGGGLVQPGRSLRLSCAASGFTFDDYAMHWVRQAPGK GLEWVSAITWNSGHIDYADSVEGRFTISRDNAKNSLNLEMNDL TPEDTAVYYCAKVSYLSTASSLDYWGQGTLVTVSS (SEQ ID NO: 27) |
| VH2 | EVQLVESGGGLVQPGRSLRLSCAASGFTFDDYAMHWVRQAPGK GLEWVSAITWNSGHIDYADSVEGRFTISRDNAKNSLNLQMNDL TPEDTAVYYCAKVSYLSTASSLDYWGQGTLVTVSS (SEQ ID NO: 28) |
| VH3 | EVQLVESGGGLVQPGRSLRLSCAASGFTFDDYAMHWVRQAPGK GLEWVSAITWNSGHIDYADSVEGRFTISRDNAKNSLYLQMNSL RPEDTAVYYCAKVSYLSTASSLDYWGQGTLVTVSS (SEQ ID NO: 29) |
| VH4 | EVQLVESGGGLVQPGRSLRLSCAASGFTFDDYAMHWVRQAPGK GLEWVSAITWNSGHIDYADSVEGRFTISRDNAKNSLYLEMNGL SPEDTAVYYCAKVSYLSTASSLDYWGQGTLVTVSS (SEQ ID NO: 30) |
| VH5 | EVQLVESGGGLVQPGRSLRLSCAASGFTFDDYAMHWVRQAPGK GLEWVSAITWNSGHIDYADSVEGRFTISRDNAKNSLSLQMNDL TTEDTAVYYCAKVSYLSTASSLDYWGQGTLVTVSS (SEQ ID NO: 31) |

TABLE 1-continued

| VH6 | EVQLVESGGGLVQPGRSLRLSCAASGFTFDDYAMHWVRQAPGK GLEWVSAITWNSGHIDYADSVEGRFTISRDNAKNSLHLEMNGL TEEDTAVYYCAKVSYLSTASSLDYWGQGTLVTVSS (SEQ ID NO: 32) |
| VH7 | EVQLVESGGGLVQPGRSLRLSCAASGFTFDDYAMHWVRQAPGK GLEWVSAITWNSGHIDYADSVEGRFTISRDNAKNSLYLEMNDL GTEDTAVYYCAKVSYLSTASSLDYWGQGTLVTVSS (SEQ ID NO: 33) |
| VH8 | EVQLVESGGGLVQPGRSLRLSCAASGFTFDDYAMHWVRQAPGK GLEWVSAITWNSGHIDYADSVEGRFTISRDNAKNSLYLEMNGL APEDTAVYYCAKVSYLSTASSLDYWGQGTLVTVSS (SEQ ID NO: 34) |
| VH9 | EVQLVESGGGLVQPGRSLRLSCAASGFTFDDYAMHWVRQAPGK GLEWVSAITWNSGHIDYADSVEGRFTISRDNAKNSLALEMNSL TPEDTAVYYCAKVSYLSTASSLDYWGQGTLVTVSS (SEQ ID NO: 35) |
| VH10 | EVQLVESGGGLVQPGRSLRLSCAASGFTFDDYAMHWVRQAPGK GLEWVSAITWNSGHIDYADSVEGRFTISRDNAKNSLSLEMNDL GAEDTAVYYCAKVSYLSTASSLDYWGQGTLVTVSS (SEQ ID NO: 36) |

In some embodiments, SEQ ID NO: 2 consists of LNLEMNDLTP (SEQ ID NO: 10). In some embodiments, SEQ ID NO: 2 consists of LNLQMNDLTP (SEQ ID NO: 11). In some embodiments, SEQ ID NO: 2 consists of LYLQMNSLRP (SEQ ID NO: 12). In some embodiments, SEQ ID NO: 2 consists of LYLEMNGLSP (SEQ ID NO: 13). In some embodiments, SEQ ID NO: 2 consists of LSLQMNDLTT (SEQ ID NO: 14). In some embodiments, SEQ ID NO: 2 consists of LHLEMNGLTE (SEQ ID NO: 15). In some embodiments, SEQ ID NO: 2 consists of LYLEMNDLGT (SEQ ID NO: 16). In some embodiments, SEQ ID NO: 2 consists of LYLEMNGLAP (SEQ ID NO: 17). In some embodiments, SEQ ID NO: 2 consists of LALEMNSLTP (SEQ ID NO: 18). In some embodiments, SEQ ID NO: 2 consists of LSLEMNDLGA (SEQ ID NO: 19). In some embodiments, SEQ ID NO: 2 consists of LTLEMNSLTP (SEQ ID NO: 20). In some embodiments, SEQ ID NO: 2 consists of LTLEMNSLTE (SEQ ID NO: 21). In some embodiments, SEQ ID NO: 2 consists of LTLEMNGLGP (SEQ ID NO: 22). In some embodiments, SEQ ID NO: 2 consists of LTLEMNGLAP (SEQ ID NO: 23). In some embodiments, SEQ ID NO: 2 consists of LYLEMNDLSD (SEQ ID NO: 24). In some embodiments, SEQ ID NO: 2 consists of LTLEMNGLSP (SEQ ID NO: 25). In some embodiments, SEQ ID NO: 2 consists of LTLEMNGLRP (SEQ ID NO: 26). In some embodiments, SEQ ID NO: 2 consists of a sequence selected from SEQ ID NO: 10-19. In some embodiments, SEQ ID NO: 2 consists of a sequence selected from SEQ ID NO: 10-26. In some embodiments, SEQ ID NO: 2 consists of a sequence selected from Table 4. In some embodiments, SEQ ID NO: 2 consists of a sequence selected from Table 6. In some embodiments, SEQ ID NO: 2 does not consist of SEQ ID NO: 12.

In some embodiments, the polypeptide further comprises an amino acid sequence $X_{12}SX_{13}X_{14}X_{15}X_{16}X_{17}X_{18}X_{19}LD$ (SEQ ID NO: 7), wherein $X_{12}$ is selected from D, E, and V; $X_{13}$ is selected from D, E, G, N, Q, T, V, W, F, L, and Y; $X_{14}$ is selected from A, E, H, L, N, P, Q, S, T, V, and W; $X_{15}$ is selected from E, S, and G; $X_{16}$ is selected from E, G, H, K, P, R, and T; $X_{17}$ is selected from A, S, and G; $X_{18}$ is selected from E, S, G, and D; and $X_{19}$ is selected from D, N, G, and S. In some embodiments, SEQ ID NO: 7 does not comprise the amino acid sequence VSYLSTASSLD (SEQ ID NO: 6). In some embodiments, SEQ ID NO: 6 and SEQ ID NO: 7 comprise a different amino acid sequence. In some embodiments, SEQ ID NO: 6 and SEQ ID NO: 7 are not identical.

In some embodiments, SEQ ID NO: 7 comprises the amino acid sequence $X_{12}SX_{20}X_{21}X_{15}X_{16}X_{22}X_{23}X_{24}LD$ (SEQ ID NO: 8), wherein $X_{12}$ is selected from D, E, and V, $X_{20}$ is selected from D, E, G, N, Q, T, V, W, and Y, $X_{21}$ is selected from A, E, H, L, N, P, Q, S, T, and W, $X_{15}$ is selected from E, S, and G, $X_{16}$ is selected from E, G, H, K, P, R, and T, $X_{22}$ is selected from A, and G, $X_{23}$ is selected from E, S, and D, and $X_{24}$ is selected from D, and S. In some embodiments, SEQ ID NO: 7 consists of SEQ ID NO: 8. In some embodiments, SEQ ID NO: 7 comprises the amino acid sequence $VSX_{25}X_{26}STX_{27}X_{28}X_{29}LD$ (SEQ ID NO: 9), wherein $X_{25}$ is selected from W, Y, G, Q, F, L, and V, $X_{26}$ is selected L, V, H, and P, $X_{27}$ is selected from A, and S, $X_{28}$ is selected from E, S, and G, and $X_{29}$ is selected from N, S, D, and G. In some embodiments, SEQ ID NO: 7 consists of SEQ ID NO: 9. In some embodiments, SEQ ID NO: 7 consists of a sequence selected from SEQ ID NO: 97-100. In some embodiments, SEQ ID NO: 7 consists of a sequence selected from SEQ ID NO: 97-112. In some embodiments, SEQ ID NO: 7 consists of VSWVSTSSSLD (SEQ ID NO: 97). In some embodiments, SEQ ID NO: 7 consists of VSWLSTSGSLD (SEQ ID NO: 98). In some embodiments, SEQ ID NO: 7 consists of VSGPSTSGNLD (SEQ ID NO: 99). In some embodiments, SEQ ID NO: 7 consists of VSWLSTSGNLD (SEQ ID NO: 100).

In some embodiments, SEQ ID NO: 2 consists of a sequence selected from Table 6. In some embodiments, SEQ ID NO: 2 consists of a sequence selected from SEQ ID NO: 37-96. In some embodiments, an antibody or antigen binding fragment comprises SEQ ID NO: 7 and SEQ ID NO: 2 consists of a sequence selected from Table 6. In some embodiments, an antibody or antigen binding fragment comprises SEQ ID NO: 7 and SEQ ID NO: 2 consists of a sequence selected SEQ ID NO: 37-96.

In some embodiments, the antibody or antigen binding fragment comprises the antigen binding domain of adalimumab wherein amino acids 79-88 of the heavy chain are replaced. In some embodiments, the antibody or antigen binding fragment comprises the antigen binding domain of ipilimumab wherein amino acids 79-88 of the heavy chain are replaced.

In some embodiments, the antibody comprises the amino acid sequence of adalimumab wherein amino acids 79-88 of the heavy chain are replaced by a sequence selected from SEQ ID NO: 3, SEQ ID NO: 4, and SEQ ID NO: 10-19. In some embodiments, the antibody comprises the amino acid sequence of adalimumab wherein amino acids 79-88 of the heavy chain are replaced by a sequence selected from SEQ ID NO: 10-19. In some embodiments, the antibody comprises the amino acid sequence of adalimumab wherein amino acids 79-88 of the heavy chain are replaced by a sequence selected from SEQ ID NO: 10-26. In some embodiments, the antibody comprises the amino acid sequence of adalimumab wherein amino acids 79-88 of the heavy chain are replaced by a sequence selected from SEQ ID NO: 10-26 and 113. In some embodiments, the antibody comprises the amino acid sequence of adalimumab wherein amino acids 79-88 of the heavy chain are replaced by a sequence selected from SEQ ID NO: 10-26 and 37-96. In some embodiments, the antibody comprises the amino acid sequence of adalimumab wherein amino acids 79-88 of the heavy chain are replaced by a sequence selected from SEQ ID NO: 10-19 and 37-96. In some embodiments, the antibody comprises the amino acid sequence of adalimumab wherein amino acids 79-88 of the heavy chain are replaced by a sequence selected from SEQ ID NO: 10-26, 37-96 and 113. In some embodiments, the antibody comprises the amino acid sequence of adalimumab wherein amino acids 79-88 of the heavy chain are replaced by a sequence selected from Table 4. In some embodiments, the antibody comprises the amino acid sequence of adalimumab wherein amino acids 79-88 of the heavy chain are replaced by a sequence selected from Table 6. In some embodiments, the antibody comprises the amino acid sequence of adalimumab wherein amino acids 79-88 of the heavy chain are replaced by a sequence selected from Tables 4 and 6. In some embodiments, amino acids 79-88 of the antibody heavy chain does not comprise SEQ ID NO: 12.

In some embodiments, the antibody comprises the amino acid sequence of ipilimumab wherein amino acids 79-88 of the heavy chain are replaced by a sequence selected from SEQ ID NO: 3 and SEQ ID NO: 4. In some embodiments, the antibody comprises the amino acid sequence of ipilimumab wherein amino acids 79-88 of the heavy chain are replaced by a sequence selected from SEQ ID NO: 3, SEQ ID NO: 4 and SEQ ID NO: 5. In some embodiments, the antibody comprises the amino acid sequence of ipilimumab wherein amino acids 79-88 of the heavy chain are replaced by a sequence selected from SEQ ID NO: 10-26. In some embodiments, the antibody comprises the amino acid sequence of ipilimumab wherein amino acids 79-88 of the heavy chain are replaced by a sequence selected from SEQ ID NO: 10-26 and 113. In some embodiments, the antibody comprises the amino acid sequence of ipilimumab wherein amino acids 79-88 of the heavy chain are replaced by a sequence selected from SEQ ID NO: 20-26. In some embodiments, the antibody comprises the amino acid sequence of ipilimumab wherein amino acids 79-88 of the heavy chain are replaced by a sequence selected from SEQ ID NO: 20-26 and 113. In some embodiments, the antibody comprises the amino acid sequence of ipilimumab wherein amino acids 79-88 of the heavy chain are replaced by a sequence selected from SEQ ID NO: 20-26. In some embodiments, the antibody comprises the amino acid sequence of ipilimumab wherein amino acids 79-88 of the heavy chain are replaced by a sequence selected from SEQ ID NO: 20-26 and 113. In some embodiments, the antibody comprises the amino acid sequence of ipilimumab wherein amino acids 79-88 of the heavy chain are replaced by a sequence selected from SEQ ID NO: 10-26. In some embodiments, the antibody comprises the amino acid sequence of ipilimumab wherein amino acids 79-88 of the heavy chain are replaced by a sequence selected from SEQ ID NO: 10-26 and 113. In some embodiments, the antibody comprises the amino acid sequence of ipilimumab wherein amino acids 79-88 of the heavy chain are replaced by LDLQMNGLGP (SEQ ID NO: 113). In some embodiments, the antibody comprises the amino acid sequence of ipilimumab wherein amino acids 79-88 of the heavy chain are replaced by a sequence selected from SEQ ID NO: 10-26, 37-96 and 113. In some embodiments, the antibody comprises the amino acid sequence of ipilimumab wherein amino acids 79-88 of the heavy chain are replaced by a sequence selected from Table 4. In some embodiments, the antibody comprises the amino acid sequence of ipilimumab wherein amino acids 79-88 of the heavy chain are replaced by a sequence selected from Table 6. In some embodiments, the antibody comprises the amino acid sequence of ipilimumab wherein amino acids 79-88 of the heavy chain are replaced by a sequence selected from Tables 4 and 6.

In some embodiments, the antibody comprises the amino acid sequence of adalimumab wherein amino acids 99-109 are replaced by SEQ ID NO: 7. In some embodiments, the antibody comprises the amino acid sequence of adalimumab wherein amino acids 99-109 are replaced by a sequence selected from SEQ ID NO: 7 and SEQ ID NO: 97-100. In some embodiments, the antibody comprises the amino acid sequence of adalimumab wherein amino acids 99-109 are replaced by a sequence selected from SEQ ID NO: 7 and SEQ ID NO: 97-112. In some embodiments, the antibody comprises the amino acid sequence of adalimumab wherein amino acids 99-109 are replaced by SEQ ID NO: 7 and amino acids 79-88 of the heavy chain are replaced by a sequence selected from Table 6. In some embodiments, the antibody comprises the amino acid sequence of adalimumab wherein amino acids 99-109 are replaced by SEQ ID NO: 7 and amino acids 79-88 of the heavy chain are replaced by a sequence selected from SEQ ID NO: 10-26 and 37-96. In some embodiments, the antibody comprises the amino acid sequence of adalimumab wherein amino acids 99-109 are replaced by SEQ ID NO: 7 and amino acids 79-88 of the heavy chain are replaced by a sequence selected from SEQ ID NO: 10-26, 37-96 and 113. In some embodiments, the antibody comprises the amino acid sequence of adalimumab wherein amino acids 99-109 are replaced by SEQ ID NO: 7 and amino acids 79-88 of the heavy chain are replaced by a sequence selected from SEQ ID NO: 37-96. In some embodiments, the antibody comprises the amino acid sequence of adalimumab wherein amino acids 99-109 are replaced by SEQ ID NO: 7 and amino acids 79-88 of the heavy chain are replaced by a sequence selected from Tables 4 and 6. In some embodiments, the antibody or antigen binding domain does not comprise SEQ ID NO: 12.

In some embodiments, the antibody comprises the amino acid sequence of adalimumab wherein amino acids 99-109 are replaced by SEQ ID NO: 97 and amino acids 79-88 are replaced by a sequence provided in Table 6 from Library 3.1. In some embodiments, the antibody comprises the amino acid sequence of adalimumab wherein amino acids 99-109 are replaced by SEQ ID NO: 98 and amino acids 79-88 are replaced by a sequence provided in Table 6 from Library 3.2. In some embodiments, the antibody comprises the amino acid sequence of adalimumab wherein amino acids 99-109 are replaced by SEQ ID NO: 99 and amino acids 79-88 are replaced by a sequence provided in Table 6 from Library 3.3. In some embodiments, the antibody comprises the amino acid sequence of adalimumab wherein amino acids 99-109 are replaced by SEQ ID NO: 100 and amino acids 79-88 are replaced by a sequence provided in Table 6 from Library 3.4. In some embodiments, the antibody comprises the amino acid sequence of adalimumab wherein amino acids 99-109 are replaced by SEQ ID NO: 97 and amino acids 79-88 are replaced by a sequence selected from SEQ ID NO: 37-54. In some embodiments, the antibody comprises the amino acid sequence of adalimumab wherein amino acids 99-109 are replaced by SEQ ID NO: 98 and amino acids 79-88 are replaced by a sequence selected from SEQ ID NO: 38, 47, 49, and 55-74. In some embodiments, the antibody comprises the amino acid sequence of adalimumab wherein amino acids 99-109 are replaced by SEQ ID NO: 99 and amino acids 79-88 are replaced by a sequence selected from SEQ ID NO: 37, 40, 43, 46, and 74-93. In some embodiments, the antibody comprises the amino acid sequence of adalimumab wherein amino acids 99-109 are replaced by SEQ ID NO: 100 and amino acids 79-88 are replaced by a sequence selected from SEQ ID NO: 37-38, 42-43, 46-47, 49, 70-71, and 94-96.

In some embodiments, the amino acid sequence of the heavy chain of adalimumab is EVQLVESGG- GLVQPGRSLRLSCAASGFTFDDYAMHWVRQAPGK-GLEWVSAITWNSGHIDYADSVEGRFTISRDNAKNS-LYLQMNSLRAEDTAVYYCAKVSYLSTASSLDYWGQ-GTLVTVSSASTKGPSVFPLAPSSKSTSGGTAALGCL-VKDYFPEPVTVSWNS GALTSGVHTFPAVLQSSGLYS-LSSVVTVPSSSLGTQTYICNVNHKPSNTKVDKKVEP-KSCDKTHTCPPCPAPELLGGPSVFLFPPKPKDTLMIS-RTPEVTCVVVDVSHEDPEVKFNWYVDGVEVHNA-KTKPREEQYNSTYRVVSVLTVLHQDWLNGKEYKCK-VSNK ALPAPIEKTISKAKGQPREPQVYTLPPSRD (SEQ ID NO: 127). In some embodiments, the amino acid sequence of the light chain of adalimumab is DIQMT-QSPSSLSASVGDRVTITCRASQGIRNYLAWYQQKPG-KAPKLLIYAASTLQSGVPSRFSGSGSGTDFTLTISSL-QPEDVATYYCQRYNRAPYTFGQGTKVEIKRTVAAPS-VFIFPPSDEQLKSGTASVVCLLNNFYPREAKVQWK-VDNALQSGNSQESVTEQDS KDSTYSLSSTLTLSKAD-YEKHKVYACEVTHQGLSSPVTKSFNRGECELTKNQ-VSLTCLVKGFYPSDIAVEWESNGQPENNYKTTPPVL-DSDGSFFLYSKLTVDKSRWQQGN VFSCSVMHEALH-NHYTQKSLSLSPGK (SEQ ID NO: 128). In some embodiments, a heavy chain of adalimumab with decreased immunogenicity comprises or consists of SEQ ID NO: 131. In some embodiments, a heavy chain of adalimumab with decreased immunogenicity comprises or consists of SEQ ID NO: 132. In some embodiments, a heavy chain of adalimumab with decreased immunogenicity comprises or consists of SEQ ID NO: 133.

In some embodiments, the amino acid sequence of the heavy chain of ipilimumab is QVQLVESGGGVVQP-GRSLRLSCAASGFTFSSYTMHWVRQAPGKGLEWVT-FISYD GNNKYYADSVKGRFTISRDNSKNTLYLQMNS-LRAEDTAIYYCARTGWLGPFDYW GQGTLVTVSSAS-TKGPSVFPLAPSSKSTSGGTAALGCLVKDYFPEPVT-VSWNSGAL TSGVHTFPAVLQSSGLYSLSSVVTVPSSS-LGTQTYICNVNHKPSNTKVDKRVEPKS CDKTHTCP-PCPAPELLGGPSVFLFPPKPKDTLMISRTPEVTCVVV-DVSHEDPEVKFN WYVDGVEVHNAKTKPREEQYN-STYRVVSVLTVLHQDWLNGKEYKCKVSNKALPAP-IEKTISKAKGQPREPQVYTLPPSRDELTKNQVSLTCL-VKGFYPSDIAVEWESNGQ PENNYKTTPPVLDSDGS-FFLYSKLTVDKSRWQQGNVFSCSVMHEALHNHYT-QKSL SLSPGK (SEQ ID NO: 129). In some embodiments, the amino acid sequence of the light chain of ipilimumab is EIVLTQSPGTLSLSPGERATLSCRASQSVGSSYLAWY-QQKPGQAPRLLIYGAFSRATGIPDRFSGSGSGTDFT-LTISRLEPEDFAVYYCQQYGSSPWTFGQGTKVEIKRT-VAAP SVFIFPPSDEQLKSGTASVVCLLNNFYPREAK-VQWKVDNALQSGNSQESVTEQDS KDSTYSLSSTLT-LSKADYEKHKVYACEVTHQGLSSPVTKSFNRGEC (SEQ ID NO: 130). In some embodiments, a heavy chain of ipilimumab with decreased immunogenicity comprises or consists of QVQLVESGGGVVQPGRSLRLSCAASGFTF-SSYTMHWVRQAPGKGLEWVTFISYD GNNKYYADS-VKGRFTISRDNSKNTLX$_1$LX$_2$MNX$_3$LX$_4$X$_5$EDTAIYY-CARTGWLGPFD YWGQGTLVTVSSASTKGPSVFPLA-PSSKSTSGGTAALGCLVKDYFPEPVTVSWNSGALTS-GVHTFPAVLQSSGLYSLSSVVTVPSSSLGTQTYICNV-NHKPSNTKVDKRVE PKSCDKTHTCPPCPAPELLGG-PSVFLFPPKPKDTLMISRTPEVTCVVVDVSHEDPEV-KFNWYVDGVEVHNAKTKPREEQYNSTYRVVSVL-TVLHQDWLNGKEYKCKVSNKALPAPIEKTISK AKG-Q PREPQVYTLPPSRDELTKNQVSLTCLVKGFYPSDIA-VEWES NGQPENNYKTTPPVLDSDGSFFLYSKLTVD-KSRWQQGNVFSCSVMHEALHNHYT QKSLSLSPGK (SEQ ID NO: 134). In some embodiments, SEQ ID NO: 134 does not comprise SEQ ID NO: 1.

In some embodiments, the antibody or antigen binding fragment comprising the replacement of SEQ ID NO: 1 with SEQ ID NO: 2 is selected from Table 2. All of the antibodies in Table 2 contain SEQ ID NO: 1, and thus all antibodies in Table 2 would benefit from conversion of SEQ ID NO: 1 to SEQ ID NO: 2 due to the reduction in immunogenicity. Indeed, any antibody containing SEQ ID NO:1 (so long as it is not in a CDR) would benefit from the conversion of SEQ ID NO: 1 to SEQ ID NO: 2.

TABLE 2 list of clinical therapeutic Abs containing the immunogenic core HC: 79:88 in FW3.

| Ab number | Name |
| --- | --- |
| 1 | abelacimab; NVS250519 |
| 2 | actoxumab; HuMAb EGFR, MDX-066, MBL-CDA1, CDA-1, CDA 1, MK-3415A (combination of actoxumab and bezlotoxumab) |
| 3 | adalimumab beta; ABP 501, ABP-501 |
| 4 | adalimumab; D2E7, LU200134; HUMIRA ® |
| 5 | afasevikumab; MCAF5352A |
| 6 | alacizumab pegol; CDP791, g165 DFM-PEG |
| 7 | alirocumab; REGN727, SAR236553, SAR-236553, anti-Homo sapiens PCSK9 |
| 8 | anrukinzumab; IMA-638 |
| 9 | aprutumab ixadotin; BAY 1187982 |
| 10 | aprutumab; BAY 1179470 |
| 11 | avelumab; MSB0010718C, MSB-0010718C, MSB0010682 |
| 12 | azintuxizumab vedotin; ABBV-838 |
| 13 | azintuxizumab; ABBV-838, PR-1471272 |
| 14 | bapineuzumab; AAB-001 |
| 15 | bersanlimab; BI-505 |
| 16 | bifikafusp alfa; L19-IL-2, L19-IL2, L19 IL2 |
| 17 | bimekizumab; CDP4940 |
| 18 | bintrafusp alfa; M7824 |
| 19 | brazikumab; MEDI2070 |
| 20 | briakinumab; ABT-874 |
| 21 | brolucizumab; ESBA-1008 |
| 22 | camrelizumab; SHR-1210 |
| 23 | cibisatamab; RG7802, RO6958688, CEA-TCB, CEA TCB, RG-7802, RO-6958688 |
| 24 | clazakizumab; ALD-518 |
| 25 | concizumab; NNC 01272-0000-2021 |
| 26 | crenezumab; MABT5102A |
| 27 | crotedumab; REGN1193 |
| 28 | cusatuzumab; ARGX-110 |
| 29 | daratumumab; HuMax-CD38 |
| 30 | dectrekumab; QAX-576 |
| 31 | denosumab; AMG162 |
| 32 | dilpacimab; ABT-165, PR-1283233 |
| 33 | domagrozumab; PF06252616 |
| 34 | dostarlimab; TSR-042, ABT1, ANB-011 |
| 35 | drozitumab; PRO95780, anti-DR5, rhuMAb DR5 |
| 36 | dupilumab; REGN668, REGN-668, SAR231893, SAR-231893 |
| 37 | durvalumab; MEDI4736 |
| 38 | efalizumab; hu1124 |
| 39 | elgemtumab; LJM716 |
| 40 | elotuzumab; HuLuc63, PDL-063, PDL063 |
| 41 | emapalumab; NI-0501 |
| 42 | emicizumab; ACE910 |
| 43 | enapotamab vedotin; HuMax-AXL |
| 44 | enapotamab; HuMax-AXL |
| 45 | enavatuzumab; PDL 192 |
| 46 | etaracizumab; hLM60, MEDI-522 |
| 47 | evinacumab; REGN 1500 |
| 48 | figitumumab; CP-751871 |
| 49 | foralumab; NI-0401 |
| 50 | foravirumab; CR4098, anti-Rabies virus glycoprotein |
| 51 | fremanezumab; TEV-48125 |
| 52 | frovocimab; LY-3015014, LY3015014 |
| 53 | gancotamab; MM-001 |
| 54 | gantenerumab; R1450 |
| 55 | gosuranemab; BMS-986168, IPN-007, huIPN-002 |
| 56 | icrucumab; 18F1, IMC-18F1, LY3012212 |
| 57 | imalumab; BAX69, BAX069 |
| 58 | inclacumab; RO4905417, LC1004-002 |
| 59 | ipilimumab; MDX-010 |
| 60 | istiratumab; MM-141 |
| 61 | istiratumab; MM-141 |

TABLE 2-continued list of clinical therapeutic Abs containing the immunogenic core HC: 79:88 in FW3.

Ab number Name

| 62 | lanadelumab; DX-2930 |
| 63 | landogrozumab; LY-2495655 |
| 64 | letolizumab; BMS-986004 |
| 65 | lexatumumab; HGS-ETR2 |
| 66 | lifastuzumab vedotin; DNIB0600A (conjugate) |
| 67 | lokivetmab; CAN34D3-65 |
| 68 | lorvotuzumab mertansine; huN901-DM1, BB-10901, IMGN901 |
| 69 | lupartumab amadotin; BAY 1129980 |
| 70 | lupartumab; BAY 1112623 |
| 71 | marstacimab; PF-06741086 |
| 72 | mosunetuzumab; BTCT4465A, RO7030816 |
| 73 | nesvacumab; REGN910, REGN-910, SAR-308846 |
| 74 | oleclumab; MEDI9447 |
| 75 | onfekafusp alfa; L19TNF |
| 76 | opicinumab; BIIB033 |
| 77 | orticumab; MLDL-1278A, BI-204, R-7418, RG-7418, anti-Homo sapiens oxLDL |
| 78 | osocimab; SYNT-001, SYNT001 |
| 79 | otelixizumab; ChAglyCD TRX4 |
| 80 | otilimab; MOR-04357, 3196165, GSK3196165, MOR103 |
| 81 | oxelumab; huMAb OX40L, RO4989991, R4930 |
| 82 | pamrevlumab; FG-3019 |
| 83 | panobacumab; Aerumab 11KBPA101, KBPA-101 |
| 84 | perakizumab; RO5310074, RG4934, anti-Homo sapiens IL17A |
| 85 | pertuzumab; rhuMAB 2C4 OMNITARGâ,,¢; PERJETA ™ |
| 86 | prasinezumab; RG7935 |
| 87 | prezalumab; AMG 557 |
| 88 | quilizumab; RG-7449, MEMP1972A, Anti-M1' |
| 89 | radretumab; L19-SIP |
| 90 | ramucirumab; 1121B IMC-1121B, LY3009806; CYRAMZA ™ |
| 91 | ravagalimab; ABBV-323 |
| 92 | remtolumab; ABT-122 |
| 93 | robatumumab; 19D12, SCH, 717454, SCH717454 |
| 94 | rozanolixizumab; UCB7665 |
| 95 | satralizumab; SA237 |
| 96 | seribantumab; SAR256212; MM121 |
| 97 | setrusumab; BPS804 |
| 98 | sirukumab; CNTO 136 |
| 99 | sofituzumab vedotin; DMUC5754A (conjugate), MMUC1206A (nonconjugate), Homosapiens MUC16 |
| 100 | solanezumab; LY2062430, anti-APP (amyloid beta A4 precursor protein) Abeta |
| 101 | suptavumab; REGN2222 |
| 102 | sutimlimab; TNT009, IPN-009, BIVV009 |
| 103 | suvratoxumab; MEDI4893 |
| 104 | tarextumab; OMP-59R5 |
| 105 | tepoditamab; MCLA-117 |
| 106 | teprotumumab; |
| 107 | tigatuzumab; CS-1008, TRA-8 |
| 108 | tisotumab vedotin; HuMax-TF-ADC |
| 109 | tisotumab; HuMax-TF |
| 110 | tovetumab; MEDI-575 |
| 111 | tremelimumab; CP-675, CP-675, 206, CP-675206 clone 11.2.1 |
| 112 | vanalimab; JNJ-64457107 |
| 113 | vandortuzumab vedotin; |
| 114 | vantictumab; OMP-18R5 |
| 115 | varlilumab; CDX-1127, 1F5 |
| 116 | vopratelimab; JTX-2011 |
| 117 | xentuzumab; BI 836845 |
| 118 | zampilimab; UCB7858 |

In some embodiments, the antibody comprises a sequence of a known antibody in which SEQ ID NO: 1 is replaced with SEQ ID NO: 2. In some embodiments, the antibody comprises a replacement of SEQ ID NO: 1 with SEQ ID NO: 2. In some embodiments, the antibody comprising the replacement of SEQ ID NO: 1 with SEQ ID NO: 2 is selected from the group consisting of: afasevikumab, adalimumab, sutimlimab, remtolumab, terextumab, elotuzumab, bimekizumab, sofituzumab vedotin, rozanolixizumab, lanadelumab, suvratoxumab, gosuranemab, ipilimumab, dupliumab, efalizumab, frovocimab, emapalumab, alirocumab, inclacumab, crotedumab, avelumab, opicinumab, emicizumab, durvalumab, solanexumab, ramucirumab, tovetumab, pertuzumab, suptavumab, nesvacumab, quilizumab, brazikumab, denosumab, varlilumab, tremelimumab, igatuzumab, robatumumab, prezalumab, prasinezumab, panobacumab, otilimab, otelixizumab, osocimab, lorvotuzumab mertansine, lexatumumab, icrucumab, fremanexumab, elgemtumab, daratumumb, corncizumab, bapineuzumab, and anrukinzumab. In some embodiments, the antibody comprising the replacement of SEQ ID NO: 1 with SEQ ID NO: 2 is selected from adalimumab or ipilimumab.

By another aspect, there is provided an antibody or an antigen binding fragment comprising SEQ ID NO: 7.

In some embodiments, a heavy chain of the antibody or antigen binding fragment comprises SEQ ID NO: 7. In some embodiments, SEQ ID NO: 7 is amino acids 99-109 of the heavy chain of the antibody or antigen binding fragment. In some embodiments, SEQ ID NO: 7 is not SEQ ID NO: 6.

In some embodiments, the antibody is adalimumab (Humira). In some embodiments, the antibody comprises the amino acid sequence of adalimumab wherein amino acids 99-109 of the heavy chain of adalimumab have been replaced by SEQ ID NO: 7. In some embodiments, the antibody or antigen binding fragment comprises the antigen binding domain of adalimumab wherein amino acids 99-109 of the heavy chain have been replaced by SEQ ID NO: 7.

In some embodiments, the antibody or antigen binding fragment further comprises SEQ ID NO: 2. In some embodiments, amino acids 79-88 of the antibody or antigen binding fragment is SEQ ID NO: 2.

By another aspect, there is provided an antibody or antigen binding fragment thereof comprising three heavy chain CDRs (CDR-H) and three light chain CDRs (CDR-L), wherein:

CDR-H1 comprises the amino acid sequence set forth in SEQ ID NO: 114 (DYAMH), CDR-H2 comprises the amino acid sequence as set forth in SEQ ID NO: 115 (AITW), CDR-H3 comprises the amino acid sequence as set forth in SEQ ID NO: 116 ($X_{12}SX_{13}X_{14}X_{15}X_{16}$ $X_{17}X_{18}X_{19}LDX_{30}$) and does not comprise SEQ ID NO: 6, CDR-L1 comprises the amino acid sequence as set forth in SEQ ID NO: 117 (RASQGIRNYLA), CDR-L2 comprises the amino acid sequence as set forth in SEQ ID NO: 118 (AASTLQS), and CDR-L3 comprises the amino acid sequence as set forth in SEQ ID NO: 119 (QRYNRAPYX$_{31}$), wherein $X_{12}$ is selected from D, E, and V, $X_{13}$ is selected from D, E, G, N, Q, T, V, W, F, L, and Y, $X_{14}$ is selected from A, E, H, L, N, P, Q, S, T, V, and W, $X_{15}$ is selected from E, S, and G, $X_{16}$ is selected from E, G, H, K, P, R, and T, $X_{17}$ is selected from A, S, and G, $X_{18}$ is selected from E, S, G, and D, $X_{19}$ is selected from D, N, G, and S, $X_{30}$ is selected from Y and N, $X_{31}$ is selected from T and A.

In some embodiments, the antibody or antigen binding fragment binds TNFa. In some embodiments, the antibody binds TNFa comparably to adalimumab. In some embodiments, the antibody or antigen binding fragment is a modified adalimumab with decreased immunogenicity. In some embodiments, the antibody or antigen binding fragment is adalimumab with a modified CDR-H3.

In some embodiments, CDR-L3 consists of SEQ ID NO: 120 (QRYNRAPYT). In some embodiments, CDR-L3 consists of SEQ ID NO: 124 (QRYNRAPYA).

In some embodiments, CDR-H3 comprises SEQ ID NO: 121 ($X_{12}SX_{13}X_{14}X_{15}X_{16}X_{17}X_{18}X_{19}LDY$). In some embodiments, CDR-H3 comprises SEQ ID NO: 125 ($X_{12}SX_{13}X_{14}X_{15}X_{16}X_{17}X_{18}X_{19}LDN$). In some embodiments, SEQ ID NO: 116 comprises $X_{12}SX_{20}X_{21}X_{15}X_{16}$ $X_{22}X_{23}X_{24}LDX_{31}$ (SEQ ID NO: 122), wherein $X_{12}$ is selected from D, E, and V, $X_{20}$ is selected from D, E, G, N, Q, T, V, W, and Y, $X_{21}$ is selected from A, E, H, L, N, P, Q, S, T, and W, $X_{15}$ is selected from E, S, and G, $X_{16}$ is selected from E, G, H, K, P, R, and T, $X_{22}$ is selected from A, and G, $X_{23}$ is selected from E, S, and D, $X_{24}$ is selected from D, and S, and $X_{31}$ is selected from T and A.

In some embodiments, SEQ ID NO: 116 comprises $VSX_{25}X_{26}STX_{27}X_{28}X_{29}LD$ $X_{31}$ (SEQ ID NO: 123), wherein $X_{25}$ is selected from W, Y, G, Q, F, L, and V, $X_{26}$ is selected L, V, H, and P, $X_{27}$ is selected from A, and S, $X_{28}$ is selected from E, S, and G, $X_{29}$ is selected from N, S, D, and G, $X_{31}$ is selected from T and A.

In some embodiments, SEQ ID NO: 116 consists of an amino acid sequence selected from SEQ ID NO: 97-112.

In some embodiments, the heavy chain of the antibody or antigen binding fragment is selected from Table 1. In some embodiments, the heavy chain of the antibody or antigen binding fragment is selected from SEQ ID NO: 27-36. In some embodiments, the heavy chain of the antibody or antigen binding fragment comprises a sequence selected from Table 1. In some embodiments, the heavy chain of the antibody or antigen binding fragment comprises a sequence selected from SEQ ID NO: 27-36.

In some embodiments, the antibody or antigen binding fragment further comprises SEQ ID NO: 2. In some embodiments, the antibody or antigen binding fragment comprises a replacement of SEQ ID NO: 1 with SEQ ID NO: 2.

In some embodiments, the light chain of the antibody or antigen binding fragment comprises or consists of SEQ ID NO: 128. In some embodiments, the heavy chain of the antibody or antigen binding fragment comprises SEQ ID NO: 127 in which SEQ ID NO: 1 has been replaced with SEQ ID NO: 2. In some embodiments, the heavy chain of the antibody or antigen binding fragment comprises SEQ ID NO: 127 in which SEQ ID NO: 6 has been replaced with SEQ ID NO: 7. In some embodiments, the heavy chain of the antibody or antigen binding fragment comprises SEQ ID NO: 127 in which SEQ ID NO:1 has been replaced with SEQ ID NO: 2 and SEQ ID NO: 6 has been replaced with SEQ ID NO: 7.

In some embodiments, the heavy chain of the antibody or antigen binding fragment comprises or consists of EVQLVESGGGLVQPGRSLRLSCAASGFTFDDYAM-HWVRQAPGKGLEWVSAITWN SGHIDYADSVEGRF-TISRDNAKNSLX$_1$LX$_2$MNX$_3$LX$_4$X$_5$EDTAVYYCAKV-SYLSTAS SLDYWGQGTLVTVSSASTKGPSVFPLAPS-SKSTSGGTAALGCLVKDYFPEPVTVSWNSGALTSG-VHTFPAVLQSSGLYSLSSVVTVPSSSLGTQTYICNV-NHKPSNTKVDK KVEPKSCDKTHTCPPCPAPELLGG-PSVFLFPPKPKDTLMISRTPEVTCVVVDVSHEDPEV-KFNWYVDGVEVHNAKTKPREEQYNSTYRVVSVL-TVLHQDWLNGKEYKCKV SNKALPAPIEKTISKA-KGQPREPQVYTLPPSRD (SEQ ID NO: 131). In some embodiments, the heavy chain of the antibody or antigen binding fragment comprises or consists of EVQLVESGG-GLVQPGRSLRLSCAASGFTFDDYAMHWVRQAPGK-GLEWVSAITWN SGHIDYADSVEGRFTISRD- NAKNS-LYLQMNSLRAEDTAVYYCAKX$_{12}$SX$_{13}$X$_{14}$X$_{15}$X$_{16}$X$_{17}$X$_{18}$X$_{19}$LDYWGQGTLVTVSSASTKGPSVFPLAPSSKST-SGGTAALGCLVKDYFPE PVTVSWNSGALTSGVHTF-PAVLQSSGLYSLSSVVTVPSSSLGTQTYICNVNHKPSN TKVDKKVEPKSCDKTHTCPPCPAPELLGGPSVFLFP-PKPKDTLMISRTPEVTCVVV DVSHEDPEVKFNWYV-DGVEVHNAKTKPREEQYNSTYRVVSVLTVLHQD- WLNGKEYKCKVSNKALPAPIEKTISKAKGQPREPQ-VYTLPPSRD (SEQ ID NO: 132). In some embodiments, the heavy chain of the antibody or antigen binding fragment comprises or consists of EVQLVESGGGLVQPGRSLRLS-CAASGFTFDDYAMHWVRQAPGKGLEWVSAITWN SGHIDYADSVEGRFTISRDNAKNSLX$_1$LX$_2$MNX$_3$LX$_4$ X$_5$EDTAVYYCAKX$_{12}$SX$_{13}$X$_{14}$X$_{15}$X$_{16}$X$_{17}$X$_{18}$X$_{19}$LDY-WGQGTLVTVSSASTKGPSVFPLAPSSKSTSGGTAAL-GCLVKDY FPEPVTVSWNSGALTSGVHTFPAVLQSSG-LYSLSSVVTVPSSSLGTQTYICNVNHKPSNTKVDK-KVEPKSCDKTHTCPPCPAPELLGGPSVFLFPPKPKD-TLMISRTPEVTCVVVDVSHEDPEVKFNWYVDGV-EVHNAKTKPREEQYNSTYRVVSVLTVLHQDWLNG KEYKCKVSNKALPAPIEKTISKAKGQPREPQV-YTLPPSRD (SEQ ID NO: 133).

In some embodiments, the antibody or antigen binding fragment binds Tumor Necrosis Factor Alpha (TNFa).

By another aspect, there is provided an antibody or antigen binding fragment comprising a heavy chain comprising SEQ ID NO: 133 and not comprising SEQ ID NO: 1.

In some embodiments, the antibody or antigen binding fragment comprising a light chain comprising SEQ ID NO: 128. In some embodiments, the heavy chain comprises SEQ ID NO: 131. In some embodiments, SEQ ID NO: 133 comprises SEQ ID NO: 2. In some embodiments, SEQ ID NO: 133 comprises SEQ ID NO: 3. In some embodiments, SEQ ID NO: 133 comprises SEQ ID NO: 4. In some embodiments, SEQ ID NO: 133 comprises SEQ ID NO: 5. In some embodiments, SEQ ID NO: 131 comprises SEQ ID NO: 2, 3, 4 or 5. Each possibility represents a separate embodiment of the invention. In some embodiments, SEQ ID NO: 2, 3, 4, or 5 is amino acids 79-88 of SEQ ID NO: 133. In some embodiments, SEQ ID NO: 2, 3, 4, or 5 is amino acids 79-88 of SEQ ID NO: 131. In some embodiments, SEQ ID NO: 133 comprises a sequence selected from SEQ ID NO: 10-26, 37-96 and 113. In some embodiments, SEQ ID NO: 131 comprises a sequence selected from SEQ ID NO: 10-26, 37-96 and 113. In some embodiments, a sequence selected from SEQ ID NO: 10-26, 37-96 and 113 is amino acids 79-88 of SEQ ID NO: 133. In some embodiments, a sequence selected from SEQ ID NO: 10-26, 37-96 and 113 is amino acids 79-88 of SEQ ID NO: 131.

In some embodiments, the antibody or antigen binding fragment binds Tumor Necrosis Factor Alpha (TNFa).

By another aspect, there is provided an antibody or antigen binding fragment comprising a heavy chain comprising SEQ ID NO: 134 and not comprising SEQ ID NO: 1.

In some embodiments, the ipilimumab with decreased immunogenicity comprises a light chain comprising or consisting of SEQ ID NO: 130. In some embodiments, the antibody or antigen binding fragment comprises a light chain comprising or consisting of SEQ ID NO: 130.

In some embodiments, SEQ ID NO: 134 comprises SEQ ID NO: 2. In some embodiments, SEQ ID NO: 134 comprises SEQ ID NO: 3. In some embodiments, SEQ ID NO: 134 comprises SEQ ID NO: 4. In some embodiments, SEQ ID NO: 134 comprises SEQ ID NO: 5. In some embodiments, SEQ ID NO: 2, 3, 4, or 5 is amino acids 79-88 of SEQ ID NO: 134. In some embodiments, SEQ ID NO: 134 comprises a sequence selected from SEQ ID NO: 10-26, 37-96 and 113. In some embodiments, a sequence selected from SEQ ID NO: 10-26, 37-96 and 113 is amino acids 79-88 of SEQ ID NO: 134.

In some embodiments, the antibody or antigen binding fragment binds Cytotoxic T-Lymphocyte-Associated protein 4 (CTLA4).

By another aspect, there is provided a pharmaceutical composition comprising a polypeptide of the invention.

By another aspect, there is provided a pharmaceutical composition comprising an antibody or antigen binding fragment of the invention.

In some embodiments, the pharmaceutical composition further comprises a pharmaceutically acceptable carrier, excipient or adjuvant. As used herein, the term "carrier," "excipient," or "adjuvant" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990);

and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

In some embodiments, the pharmaceutical composition is formulated for administration to a subject. In some embodiments, the pharmaceutical composition is formulated for systemic administration. In some embodiments, the subject is a mammal. In some embodiments, the subject is a human.

As used herein, the terms "administering," "administration," and like terms refer to any method which, in sound medical practice, delivers a composition containing an active agent to a subject in such a manner as to provide a therapeutic effect. In some embodiments, administration is administration of a therapeutically effective amount of a composition of the present subject matter to a patient in need thereof. Suitable routes of administration can include oral, parenteral, subcutaneous, intravenous, intramuscular, or intraperitoneal.

The dosage administered will be dependent upon the age, health, and weight of the recipient, kind of concurrent treatment, if any, frequency of treatment, and the nature of the effect desired.

By another aspect, there is provided a method of producing a second antibody from a first antibody, the method comprising:

a. providing a first nucleic acid molecule comprising a coding sequence which encodes an amino acid sequence of said first antibody, wherein said amino acid sequence comprises SEQ ID NO: 1;

b. providing a second nucleic acid molecule encoding an amino acid sequence of a second antibody wherein said amino acid sequence comprises SEQ ID NO: 2 in place of SEQ ID NO: 1; and c. producing a second antibody from the second nucleic acid molecule;

thereby producing a second antibody from a first antibody.

In some embodiments, the method is a method for producing a second antibody with decreased immunogenicity as compared to the first antibody. In some embodiments, the method if for reducing the immunogenicity of an antibody. In some embodiments, the producing a second antibody comprises reducing the immunogenicity of the first antibody.

In some embodiments, reduced immunogenicity comprises a reduction of at least 5, 10, 20, 25, 30, 40, 50, 60, 70, 75, 80, 85, 90, 95, 97, 99 or 100%. Each possibility represents a separate embodiment of the invention. In some embodiments, the method further comprises confirming reduced immunogenicity of the second antibody. In some embodiments, immunogenicity is measured by calculating immunogenicity score. Calculating immunogenicity is well known in the art and many programs are available for this calculation. Methods of calculating immunogenicity can be found in the Methods section hereinbelow.

In some embodiments, providing a second nucleic acid molecule comprises selecting the first nucleic acid molecule and replacing the sequence encoding SEQ ID NO: 1 with a sequence encoding SEQ ID NO: 2. In some embodiments, the second nucleic acid molecule is identical to said first nucleic acid molecule except in the region encoding SEQ ID NO:1 and SEQ ID NO: 2. In some embodiments, the second nucleic acid molecule encodes an amino acid sequence identical to an amino acid sequence encoded by the first nucleic acid molecule except for the region of SEQ ID NO: 1 and SEQ ID NO: 2. In some embodiments, replacing is mutating. In some embodiments, replacing is generating a new sequence. In some embodiments, the sequence is in an electronic file. In some embodiments, the method is a computerized method.

In some embodiments, a heavy chain of the second antibody comprises SEQ ID NO: 2. In some embodiments, SEQ ID NO: 2 is amino acids 79-88 of the heavy chain of the second antibody. In some embodiments, a heavy chain of the first antibody comprises SEQ ID NO: 1. In some embodiments, SEQ ID NO: 1 is amino acids 79-88 of the heavy chain of the first antibody. In some embodiments, SEQ ID NO: 1 is not in a CDR of the first antibody. In some embodiments, SEQ ID NO: 1 does not overlap with a CDR of the first antibody. In some embodiments, SEQ ID NO: 1 is not in a region that determines binding of the first antibody. In some embodiments, SEQ ID NO: 1 does not overlap with a region that determines binding of the first antibody.

In some embodiments, the nucleic acid molecule is a vector. In some embodiments, the nucleic acid molecule is an expression vector. In some embodiments, the expression vector is configured for expression of the antibody in a target cell. In some embodiments, the region encoding the antibody is operatively linked to at least one regulatory element. In some embodiments, the regulatory element is configured for expression of the antibody in a target cell. In some embodiments, the element is a promoter. In some embodiments, the producing comprises culturing a host cell comprising the vector. In some embodiments, the producing comprises expression the antibody in a host cell.

Expressing of a nucleic acid molecule that encodes an antibody within a cell is well known to one skilled in the art. It can be carried out by, among many methods, transfection, viral infection, or direct alteration of the cell's genome. In some embodiments, the gene is in an expression vector such as plasmid or viral vector. One such example of an expression vector containing p16-Ink4a is the mammalian expression vector pCMV p16 INK4A available from Addgene.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, the method of the invention further comprises measuring binding of the second antibody to a target or epitope of the first antibody. In some embodiments, the method of the invention further comprises confirming binding of the second antibody to a target or epitope of the first antibody. In some embodiments, the method of the invention further comprises selected an antibody with comparable binding as the first antibody to a target or epitope. In some embodiments, binding to a target or epitope is measured by a binding assay. In some embodiments, the binding assay is a FACS assay. In some embodiments, measuring by a binding assay produces a binding value. In some embodiments, the binding value is a percentage of the epitope or target that is bound, i.e. number of cells expressing the target protein that are bound. In some embodiments, the affinity of binding is the binding value. In some embodiments, the EC50 is the binding value.

In some embodiments, the binding value of the second antibody is at least 50, 55, 60, 65, 70, 75, 80, 85, 90, 95, 97, 99 or 100% of the binding value of the first antibody. Each possibility represents a separate embodiment of the invention. In some embodiments, the second antibody has a reduced binding as compared to the first antibody of less than 20, 15, 10, 9, 8, 7, 6, 5, 4, 3, 2, or 1%. Each possibility represents a separate embodiment of the invention. In some embodiments, the FACS histogram of binding of the first and second antibodies are comparable.

In some embodiments, the first antibody is selected from Table 2. In some embodiments, the first antibody is selected from the group consisting of: afasevikumab, adalimumab, sutimlimab, remtolumab, terextumab, elotuzumab, bimekizumab, sofituzumab vedotin, rozanolixizumab, lanadelumab, suvratoxumab, gosuranemab, ipilimumab, dupliumab, efalizumab, frovocimab, emapalumab, alirocumab, inclacumab, crotedumab, avelumab, opicinumab, emicizumab, durvalumab, solanexumab, ramucirumab, tovetumab, pertuzumab, suptavumab, nesvacumab, quilizumab, brazikumab, denosumab, varlilumab, tremelimumab, igatuzumab, robatumumab, prezalumab, prasinezumab, panobacumab, otilimab, otelixizumab, osocimab, lorvotuzumab mertansine, lexatumumab, icrucumab, fremanexumab, elgemtumab, daratumumb, corncizumab, bapineuzumab, and anrukinzumab. In some embodiments, the first antibody is selected from adalimumab or ipilimumab.

As used herein, the term "antibody" refers to a polypeptide or group of polypeptides that include at least one binding domain that is formed from the folding of polypeptide chains having three-dimensional binding spaces with internal surface shapes and charge distributions complementary to the features of an antigenic determinant of an antigen. An antibody typically has a tetrameric form, comprising two identical pairs of polypeptide chains, each pair having one "light" and one "heavy" chain. The variable regions of each light/heavy chain pair form an antibody binding site. An antibody may be oligoclonal, polyclonal, monoclonal, chimeric, camelised, CDR-grafted, multi-specific, bi-specific, catalytic, humanized, fully human, anti-idiotypic and antibodies that can be labeled in soluble or bound form as well as fragments, including epitope-binding fragments, variants or derivatives thereof, either alone or in combination with other amino acid sequences. An antibody may be from any species. The term antibody also includes binding fragments, including, but not limited to Fv, Fab, Fab', F(ab')2 single stranded antibody (svFC), dimeric variable region (Diabody) and disulphide-linked variable region (dsFv). In particular, antibodies include immunoglobulin molecules and immunologically active fragments of immunoglobulin molecules, i.e., molecules that contain an antigen binding site. Antibody fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)~Fc fusions and scFv-scFv-Fc fusions.

Immunoglobulin molecules can be of any type (e.g., IgG, IgE, IgM, IgD, IgA and IgY), class (e.g., IgG1, IgG2, IgG3, IgG4, IgA1 and IgA2) or subclass. In some embodiments, the antibody comprises IgG2 or IgG4. In some embodiments, the antibody comprises IgG2. In some embodiments, the antibody comprises IgG4.

The basic unit of the naturally occurring antibody structure is a heterotetrameric glycoprotein complex of about 150,000 Daltons, composed of two identical light (L) chains and two identical heavy (H) chains, linked together by both noncovalent associations and by disulfide bonds. Each heavy and light chain also has regularly spaced intra-chain disulfide bridges. Five human antibody classes (IgG, IgA, IgM, IgD and IgE) exist, and within these classes, various subclasses, are recognized based on structural differences, such as the number of immunoglobulin units in a single antibody molecule, the disulfide bridge structure of the individual units, and differences in chain length and sequence. The class and subclass of an antibody is its isotype.

The amino terminal regions of the heavy and light chains are more diverse in sequence than the carboxy terminal regions, and hence are termed the variable domains. This part of the antibody structure confers the antigen-binding specificity of the antibody. A heavy variable (VH) domain and a light variable (VL) domain together form a single antigen-binding site, thus, the basic immunoglobulin unit has two antigen-binding sites. Particular amino acid residues are believed to form an interface between the light and heavy chain variable domains (Chothia et al., J. Mol. Biol. 186, 651-63 (1985); Novotny and Haber, (1985) Proc. Natl. Acad. Sci. USA 82 4592-4596).

The carboxy terminal portion of the heavy and light chains form the constant domains i.e. CH1, CH2, CH3, CL. While there is much less diversity in these domains, there are differences from one animal species to another, and further, within the same individual there are several different isotypes of antibody, each having a different function.

The term "framework region" or "FR" refers to the amino acid residues in the variable domain of an antibody, which are other than the hypervariable region amino acid residues as herein defined. The term "hypervariable region" as used herein refers to the amino acid residues in the variable domain of an antibody, which are responsible for antigen binding. The hypervariable region comprises amino acid residues from a "complementarity determining region" or "CDR". The CDRs are primarily responsible for binding to an epitope of an antigen. The extent of FRs and CDRs has been precisely defined (see, Kabat et al.).

Immunoglobulin variable domains can also be analyzed using the IMGT information system (www://imgt. cines.fr/) (IMGT®/V-Quest) to identify variable region segments, including CDRs. See, e.g., Brochet, X. et al, Nucl. Acids Res. J6:W503-508 (2008).

Chothia et al. also defined a numbering system for variable domain sequences that is applicable to any antibody. One of ordinary skill in the art can unambiguously assign this system of "Chothia numbering" to any variable domain sequence, without reliance on any experimental data beyond the sequence itself. As used herein, "Chothia numbering" refers to the numbering system set forth by Chothia et al., Journal of Molecular Biology, "Canonical Structures for the Hypervariable regions of immunoglobulins" (1987) and Chothia et al., Nature, "Conformations of Immunoglobulin Hypervariable Regions" (1989).

As used herein, the term "humanized antibody" refers to an antibody from a non-human species whose protein sequences have been modified to increase similarity to human antibodies. A humanized antibody may be produced by production of recombinant DNA coding for the CDRs of the non-human antibody surrounded by sequences that resemble a human antibody. In some embodiments, the humanized antibody is a chimeric antibody. In some embodiments, humanizing comprises insertion of the CDRs of the invention into a human antibody scaffold or backbone. Humanized antibodies are well known in the art and any method of producing them that retains the CDRs of the invention may be employed.

The term "monoclonal antibody" or "mAb" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies and is not to be construed as produced by any specific preparation method. Monoclonal antibodies to be used in accordance with the methods provided herein, may be made by the hybridoma method first described by Kohler et al, Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624-628 (1991) and Marks et al, J. Mol. Biol. 222:581-597 (1991), for example.

The mAb of the present invention may be of any immunoglobulin class including IgG, IgM, IgD, IgE or IgA. A hybridoma producing a mAb may be cultivated in vitro or in vivo. High titers of mAbs can be obtained in vivo production where cells from the individual hybridomas are injected intraperitoneally into pristine-primed Balb/c mice to produce ascites fluid containing high concentrations of the desired mAbs. mAbs of isotype IgM or IgG may be purified from such ascites fluids, or from culture supernatants, using column chromatography methods well known to those of skill in the art.

"Antibody fragments" comprise a portion of an intact antibody, preferably comprising the antigen binding region thereof. Examples of antibody fragments include Fab, Fab', F(ab')2, and Fv fragments; diabodies; tandem diabodies (taDb), linear antibodies (e.g., U.S. Pat. No. 5,641,870, Example 2; Zapata et al, Protein Eng. 8(10): 1057-1062 (1995)); one-armed antibodies, single variable domain antibodies, minibodies, single-chain antibody molecules; multispecific antibodies formed from antibody fragments (e.g., including but not limited to, db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three surfaces of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called a, delta, e, gamma, and micro, respectively. The subunit structures and three-dimensional configurations of different classes of immunoglobulins are well known.

"Single-chain Fv" or "scFv" antibody fragments comprise the VH and VL domains of antibody, wherein these domains are present in a single polypeptide chain. In some embodiments, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies production is known in the art and is described in Natl. Acad. Sci. USA, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain (VH) and a light chain variable domain (VL), where the VHVL unit has polyepitopic specificity, antibodies having two or more VL and VH domains with each VHVL unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s).

The monoclonal antibodies of the invention may be prepared using methods well known in the art. Examples include various techniques, such as those in Kohler, G. and Milstein, C, Nature 256: 495-497 (1975); Kozbor et al, Immunology Today 4: 72 (1983); Cole et al, pg. 77-96 in MONOCLONAL ANTIBODIES AND CANCER THERAPY, Alan R. Liss, Inc. (1985).

Besides the conventional method of raising antibodies in vivo, antibodies can be generated in vitro using phage display technology. Such a production of recombinant antibodies is much faster compared to conventional antibody production and they can be generated against an enormous number of antigens. Furthermore, when using the conventional method, many antigens prove to be non-immunogenic or extremely toxic, and therefore cannot be used to generate antibodies in animals. Moreover, affinity maturation (i.e., increasing the affinity and specificity) of recombinant antibodies is very simple and relatively fast. Finally, large numbers of different antibodies against a specific antigen can be generated in one selection procedure. To generate recombinant monoclonal antibodies, one can use various methods all based on display libraries to generate a large pool of antibodies with different antigen recognition sites. Such a library can be made in several ways: One can generate a synthetic repertoire by cloning synthetic CDR3 regions in a pool of heavy chain germline genes and thus generating a large antibody repertoire, from which recombinant antibody fragments with various specificities can be selected. One can use the lymphocyte pool of humans as starting material for the construction of an antibody library. It is possible to construct naive repertoires of human IgM antibodies and thus create a human library of large diversity. This method has been widely used successfully to select a large number of antibodies against different antigens. Protocols for bacteriophage library construction and selection of recombinant antibodies are provided in the well-known reference text Current Protocols in Immunology, Colligan et al (Eds.), John Wiley & Sons, Inc. (1992-2000), Chapter 17, Section 17.1.

Non-human antibodies may be humanized by any methods known in the art. In one method, the non-human complementarity determining regions (CDRs) are inserted into a human antibody or consensus antibody framework sequence. Further changes can then be introduced into the antibody framework to modulate affinity or immunogenicity.

In some embodiments, antibodies and portions thereof include: antibodies, fragments of antibodies, Fab and F(ab') 2, single-domain antigen-binding recombinant fragments and natural nanobodies. In some embodiments, the antigen binding fragment is selected from the group consisting of a Fv, Fab, F(ab')₂, scFV or a scFV₂ fragment.

In some embodiments, the present invention provides nucleic acid sequences encoding the antibodies or antigen binding portions of the present invention.

For example, the polynucleotide may encode an entire immunoglobulin molecule chain, such as a light chain or a heavy chain. A complete heavy chain includes not only a heavy chain variable region (VH) but also a heavy chain constant region (CH), which typically will comprise three constant domains: CH1, CH2 and CH3; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and CHI and CK or CL domain has been excised. As minibodies are smaller than conventional antibodies they should achieve better tissue penetration in clinical/diagnostic use but being bivalent they should retain higher binding affinity than monovalent antibody fragments, such as dAbs. Accordingly, unless the context dictates otherwise, the term "antibody" as used herein encompasses not only whole antibody molecules, but also antigen-binding antibody fragments of the type discussed above. Each framework region present in the encoded polypeptide may comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions. Given the properties of the individual amino acids comprising the disclosed protein products, some rational substitutions will be recognized by the skilled worker. Amino acid substitutions, i.e. "conservative substitutions," may be made, for instance, on the basis of similarity in polarity, charge, solubility, hydrophobicity, hydrophilicity, and/or the amphipathic nature of the residues involved.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Methods:

'Immuno-score' calculation: The protein sequence was first analyzed using the NetMHCIIpan algorithm, which identifies 15 mer peptides with 9 mer core epitopes that may be bound my MHC class II molecule. Predictions were made for each 15 mers in a protein sequence and for each of the 27 alleles in our dataset. 15mers epitope was labeled as CD4+ epitope if it ranked in the top 2% out of IEDB peptides. The raw predictions were then weighted according to two parameters: (1) the allele frequency in the population. (2) The dependency of the identified core epitopes in the location within 15 mers peptide. These two parameters are combined to an 'immunogenicity score' for each residue by:

$$\text{Immunogenicity score} = \sum_{i=1}^{27 alleles} w_i * b_i * f_j,$$

where:

$w_i$—is the HLA frequency of allele i
$b_i$—is the HLA binding IC50 value of allele i, and
$f_j$—is the frequency of epitopes of length 9 within the 15-mer that position j belongs to (ranging 1-7)
While core location dependency is calculated as: core location dependency=occurrence of 9 mers core within identified 15 mers epitope/7

'Similarity-to-self' calculation: The human proteome with approximately 20,000 human protein sequences was downloaded from UniprotKB. We used the query: proteome: up000005640 AND reviewed: yes. Each protein sequence was divided into 9 mers peptides indentation by one residue. This dataset contained about 10 million 9-mers sequences presented in the human proteome. Then each of the 9-mer peptides in Humira sequence was analyzed by EMBOSS needle against the dataset of human 9mers peptides, using the parameters: -gapopen 100 -gapextend 10 -endweight Y -endopen 100 -endextend 10. The similarity to self was calculated as the number of identical 9mers peptides in the human proteome.

Example 1: Computational Mapping of Immunological Hotspots in the Variable Region of Adalimumab The development of anti-drug antibodies (ADAs) is a common problem with modern biologics as many therapeutic proteins elicit an immune response in patients which reduces the efficacy of the biologic. ADA development depends on the induction of CD4+ T-cells, which activate plasma B-cells to produce Abs. CD4+ T-cells are activated upon the formation of the immunological complex between a T cell receptor (TCR) on the T cells and a HLA class II molecule bound to foreign peptide on an antigen presenting cell (APC). Thus, for the identification of immunologic hotspots, two parameters are calculated: (i) the 'immuno-score'—the probability of each 9-mer peptide in a protein sequence to be presented by HLA class II molecule and (ii) the 'similarity-to-self' of each 9-mer peptide in the protein sequence, i.e. the number of identical peptides in the human proteome. For further details, see Methods. The degree of similarity-to-self negatively correlates with the probability of finding a TCR in the human T cell repertoire that can recognize a specific MHC-peptide complex, as T cells that express a TCR, that binds a WIC-self peptide complex are eliminated by negative selection during T cell development in the thymus.

The human antibody Adalimumab (Humira, an anti-TNFa antibody), is a widely used therapeutic monoclonal antibody. Depending on the study examined 9-89% of patients treated with Humira develop ADAs. Similarly, about 25% of patients treated with Ipilimumab (an anti-CTLA4 antibody) were reported to develop ADAs. Enzyme replacement therapies such as those for treating lysosomal storage disease (50-97% ADAs) and hemophilia (5-88% ADAs) were also found to produce ADAs, demonstrating the scope of this problem. Due to Adalimumab's wide distribution and high incidence of ADAs (especially in the Israeli population, ~40%) it was selected for study.

Figure 1B:
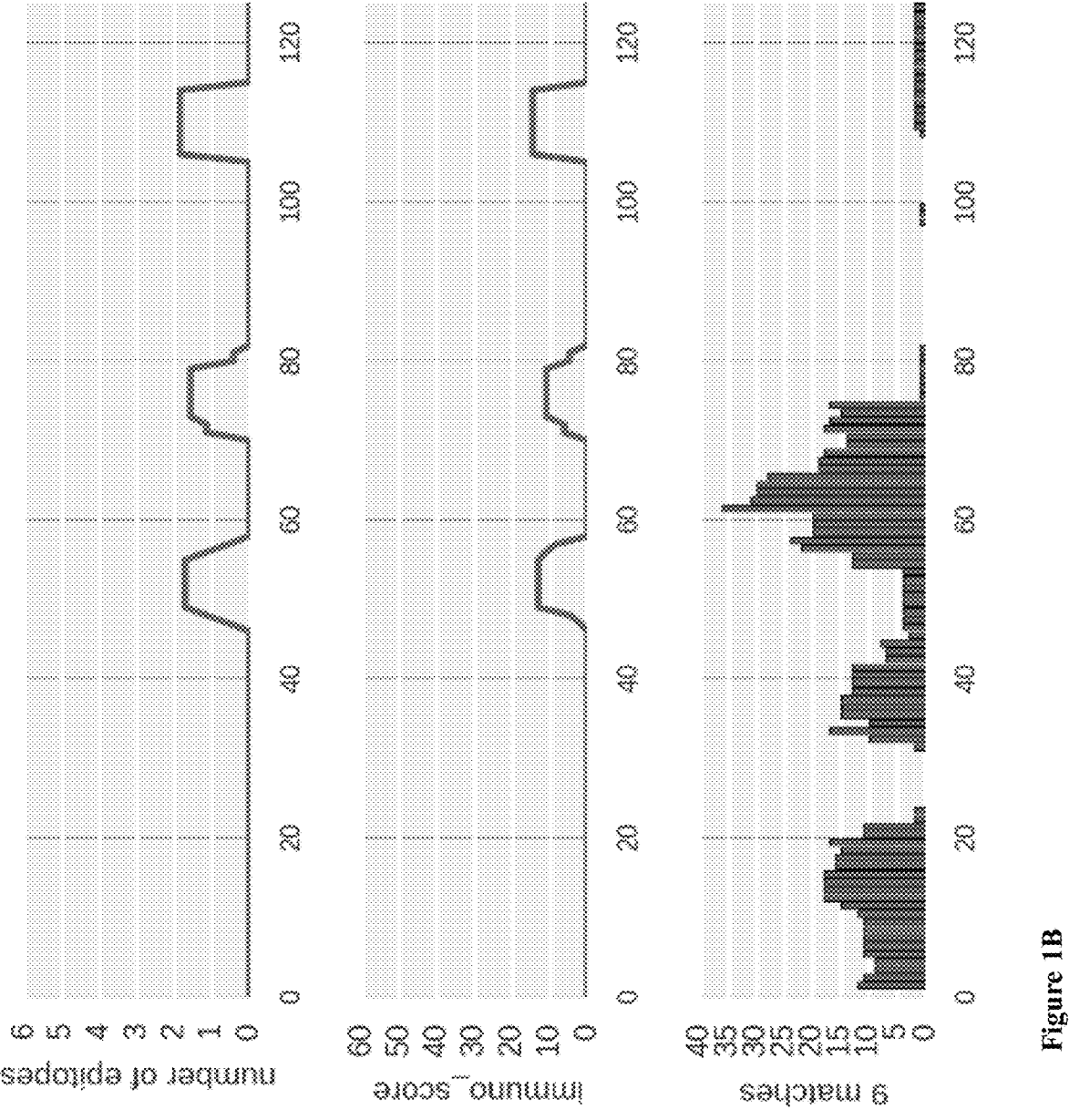

The mapping of potential immunogenic hotspot in Humira variable regions is summarized in FIG. 1A. The VL domain display two regions located in position 47-57 and 71-81 with medium immune score, thus medium probability to bind MHC class II molecules. However, these regions have high similarity to self-values (FIG. 1B). Thus, those regions were not defined as predicted hotspot.

Figure 1C:
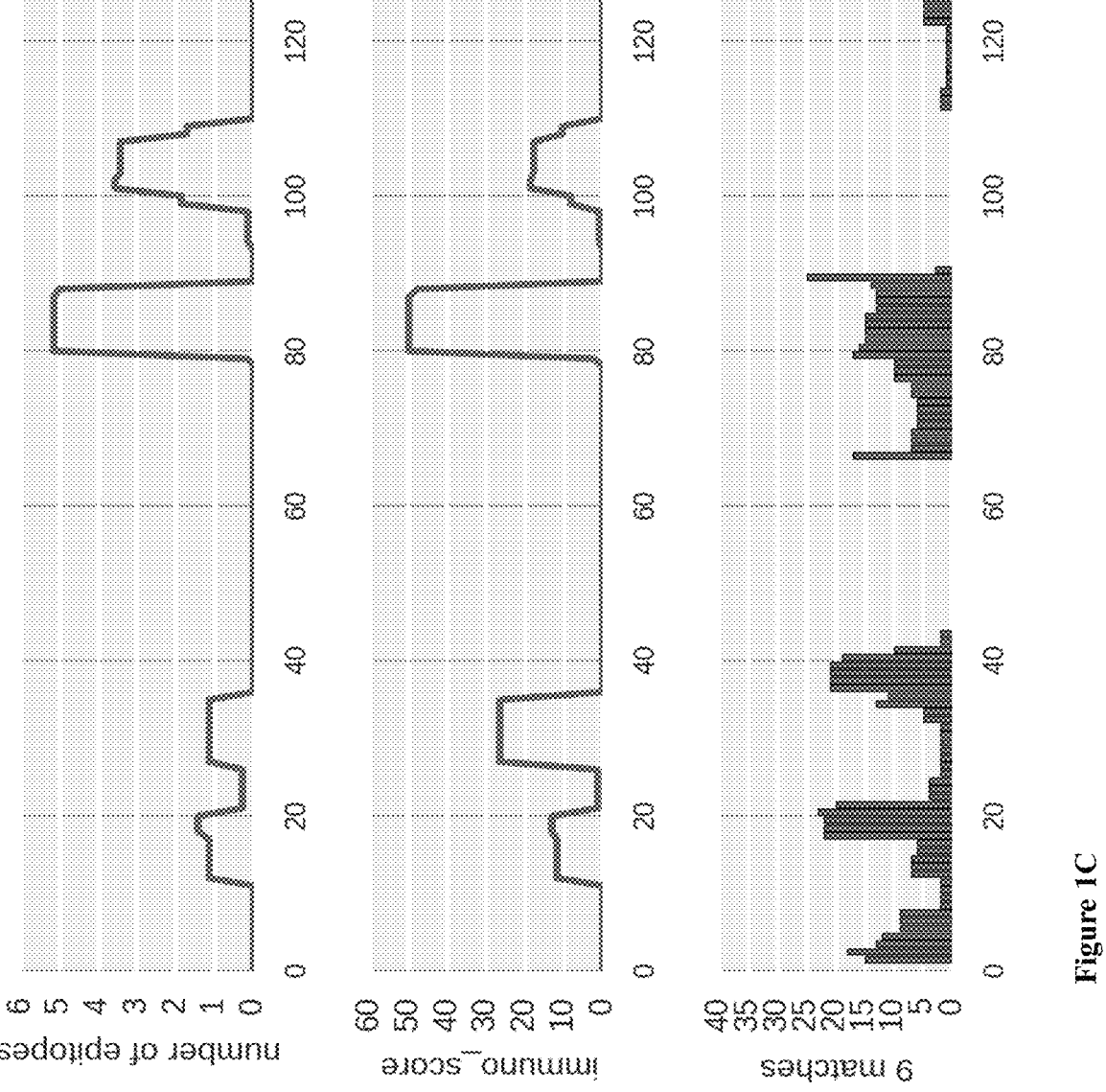

The VH domain (heavy chain) displays four epitopes. The highest immuno-score is for the residues LYLQMNSLRA located in position 79 to 88, this epitope is referred to as HC:79:88. Due to its high immune score, this epitope was categorized as a potential immunogenic hotspot although it had high similarity to self-values (FIG. 1C). An additional epitope located in position 99 to 109 presented moderate immune-score and 9-mer peptides in the human genome identical to the peptides in this region or even peptides with one amino acid substitutions were not identified (FIG. 1C). Thus this epitope was also predicted to be an immunological hotspot and this epitope was referred to as HC:99:109. There are two more potential epitopes in the start of the VH domain, however, these hotspots present low to medium immuno-score and medium similarity to self (FIG. 1C). These regions were not classified as potential immunogenic hotspots.

Specifically, the residues in the VH sequence were divided into 5 categories according to their occurrence within: (1) Peptides that were not tested for HLA binding. (2) Peptides that did not present binding towards the tested HLA allele, IC50>1000 nM. (3) Binder peptides with 1000 nM>IC50>50 nM. (4) Peptides displaying strong binding 50 nM>IC50>5 nM and (5) Ultra peptides that tightly bind the JLA with IC50<5 nM. Residues that were within peptides from two or more categorized were defined according to the peptide with the lowest IC50. As seen in FIG. 1A, residues within or near the epitope HC:79:88 are part of peptides that display ultra-binding to four out of the six tested HLA alleles and strong to medium binding towards the two additional HLA molecules. Residues located in or near epitope HC:99: 109 are part of strong binding peptides regarding four alleles and binder peptides regarding the two additional alleles. For residue in position 1-15 and 21-51 binder peptides to any of the tested alleles were not identified. Other positions in the VH domain were not tested. Overall the two epitopes HC:79:88 and HC:88:109 are presented by diverse HLA alleles molecule indicating the immunogenicity potential of these epitope across the world-wide population.

Figure 2:
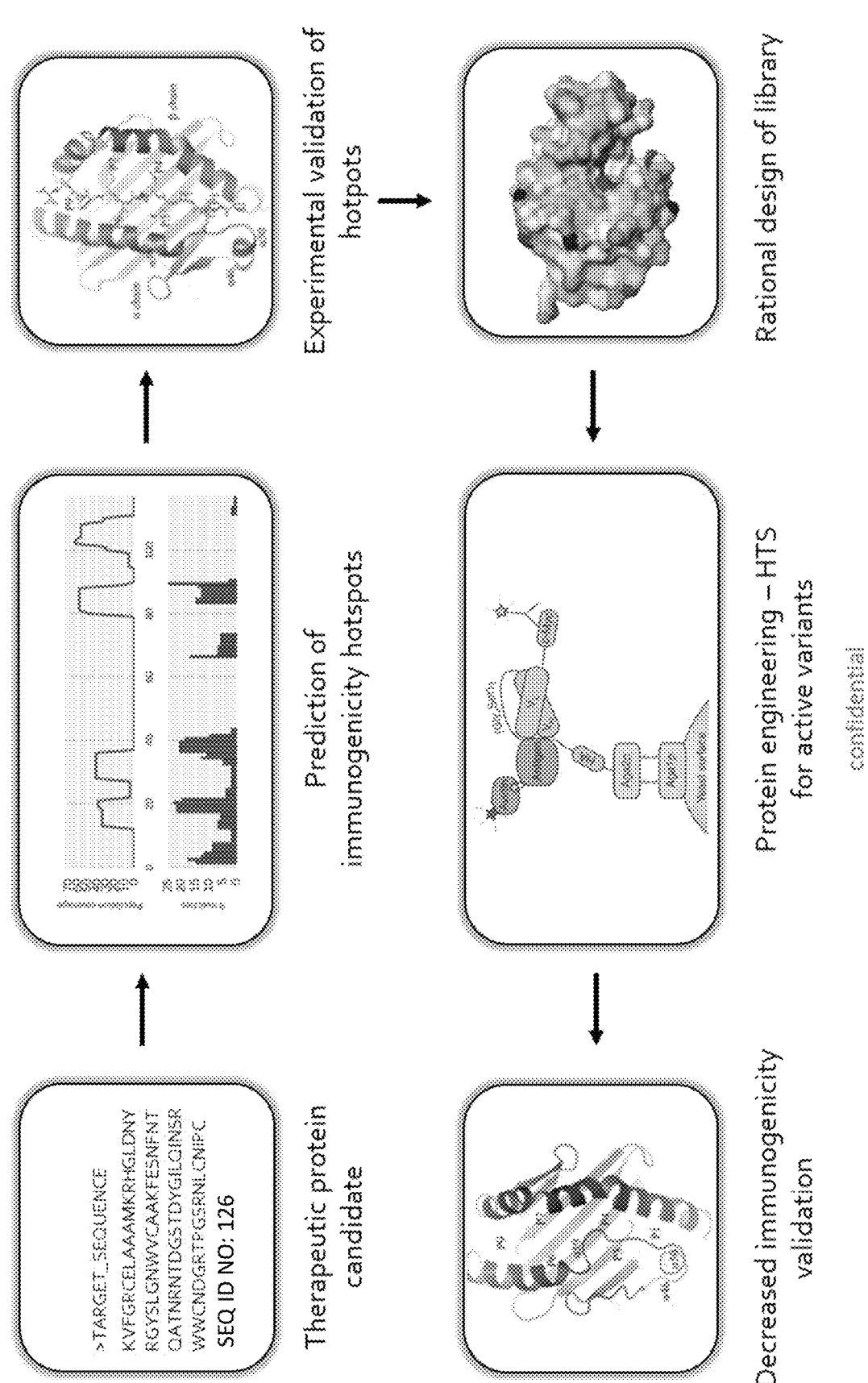
FIG. 2: Flowchart of an embodiment of a method of the invention.

Example 2: Generation of Epitopes with Reduced Antigenicity and Conserved Binding to Target The method of generation of epitopes with reduced antigenicity, but conserved binding to the target is as follows. Briefly, epitopes HC79:88 and 99:109 were altered for reduced immunogenicity. This was done by alignment of homologous sequences, followed by calculation of position frequencies matrices. An immunogenicity analysis of the resultant mutations was performed and a structural analysis, which yielded 750 possible sequences for HC79:88 replacement and $1.4 \times 10^5$ sequences for HC99:109 replacement. Yeast surface display libraries were used to express these mutant sequences and retained binding to their target was tested by FACS analysis. Targets with comparable binding to that of wild-type antibodies were retained as mutant sequences with reduced immunogenicity but conserved function. This process is summarized in FIG. 2.

Figure 3A:
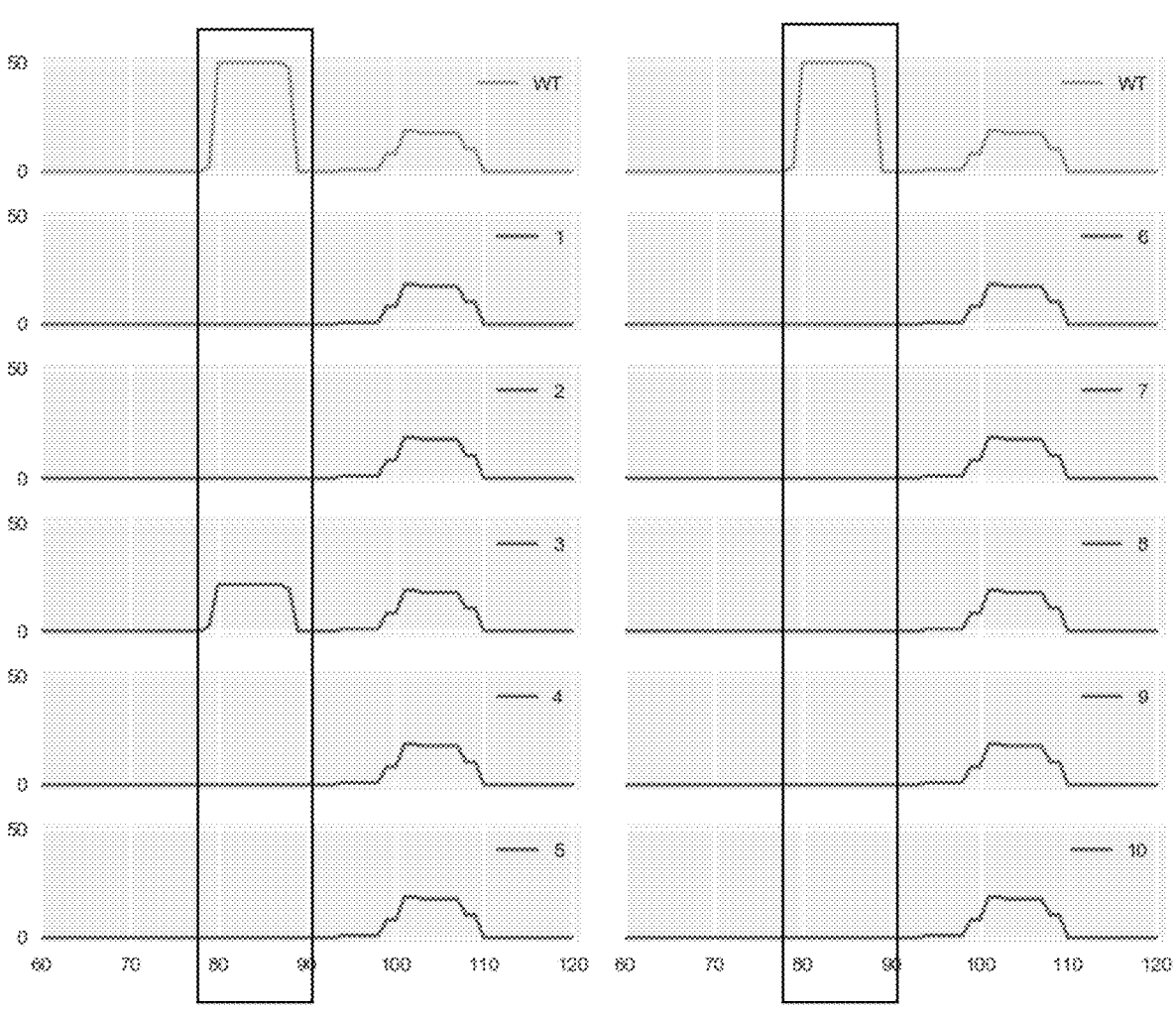
FIGS. 3A-3F: Peptides with reduced immunogenicity. (3A-3B) Line graphs of predicted immunogenicity of representative peptides from (3A) Library 1 and (3B) Library 2. WT Humira was used a control. (3C-3D) Shared motifs for (3C) Library 1 and (3D) Library 2. (3E-3F) Shared motifs for (3E) Library 1 selected peptides and (3F) Library 2 selected peptides.
Figure 3B:
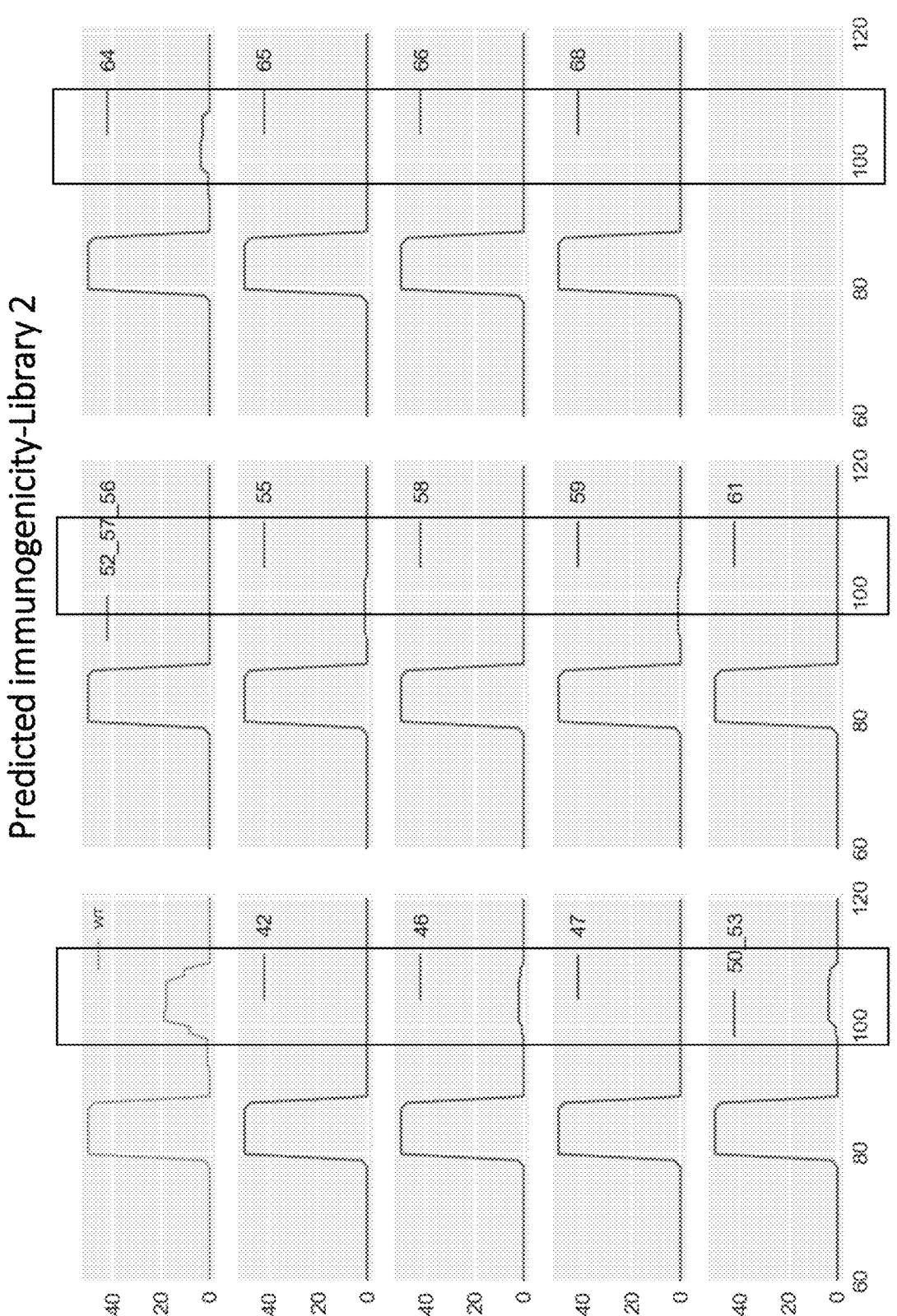
Figure 3C:
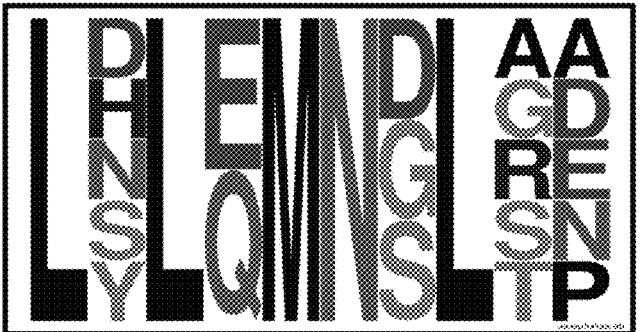
Figure 3D:

Having already determined two immunogenic hotspots in the heavy chain of Humira, two libraries (one for each hotspot) were created with alternative sequences for replacement of the hotspots. The library covering HC:79-88 was designated Library 1 and the library covering HC 99:109 was designated Library 2. Library 1 covered 10-mers and thus had a total diversity of $1 \times 10^{13}$ possible sequences. Library 2 covered 11-mers and thus had a total diversity of $1 \times 10^{14}$ possible sequences. However, many of these possible sequences shared the immunogenic problems of the parent sequences, thus the first step was to remove sequences with high immuno-scores and low similarity to self. Representative clones from Library 1 with little to no immunogenicity in the HC:79-88 region are shown in FIG. 3A, and clones from Library 2 with little to no immunogenicity in the HC: 99-109 region are shown in FIG. 3B. The conserved epitopes for Library 1 and Library 2 are presented in FIGS. 3C and 3D, respectively.

Vectors encoding recombinant ScFvs of Humira with mutations to include the sequences from Library 1 and Library 2 were generated and expressed in a yeast high-throughput display system. Three successive enrichments by FACS were performed to produce an enriched population highly expressing the recombinant mutant Humira.

Figure 4B:
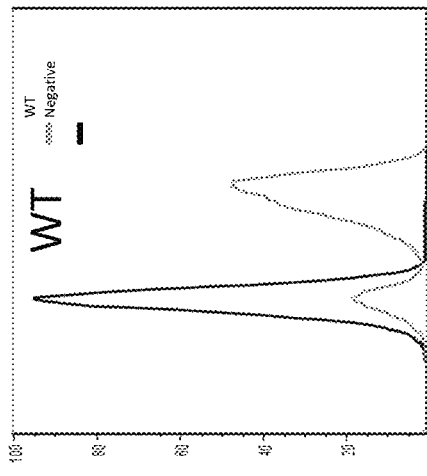
FIGS. 4A-4B: (4A-4B) Histograms of TNFa binding of antibodies containing the peptides of (4A) Library 1 and (4B) Library 2. Binding of WT Humira is provided as a control.
Figure 4B:
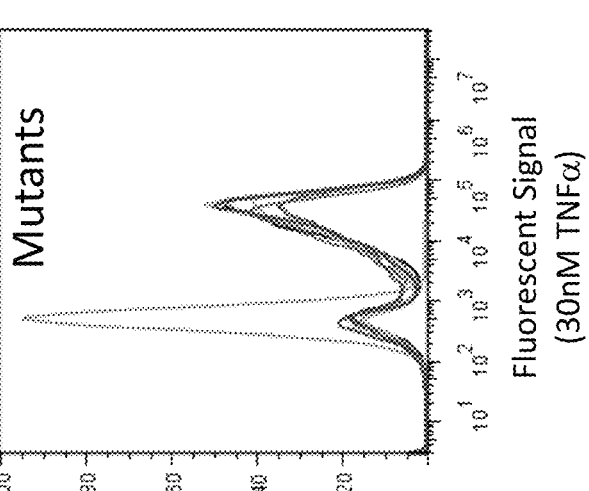
Figure 4A:
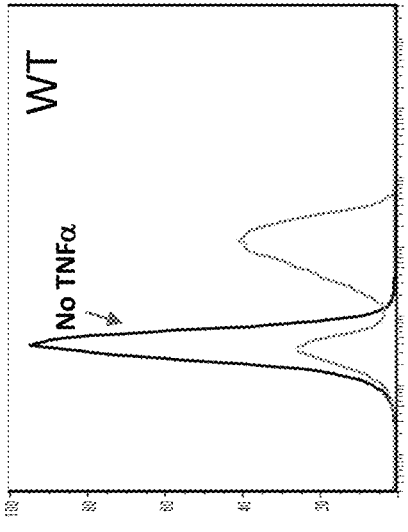
Figure 4A:
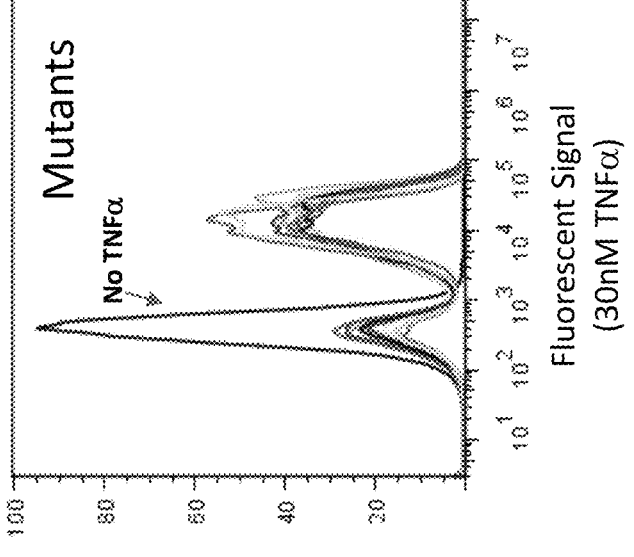

The mutant antibodies were now tested for binding to TNFa expressed on the cell surface. Yeast cells expressing TNFa were incubated with the mutant antibodies and surface binding was examined by FACS (FIG. 4A-4B). Mutants that were capable of binding TNFa at least as well as the WT Humira were selected. Each enriched clone was then sequenced for the specific mutant region present. After this functionality test, Library 1 contained only 750 sequences and Library 2 only $1.4 \times 10^5$ sequences.

Figures 5A, 5B:
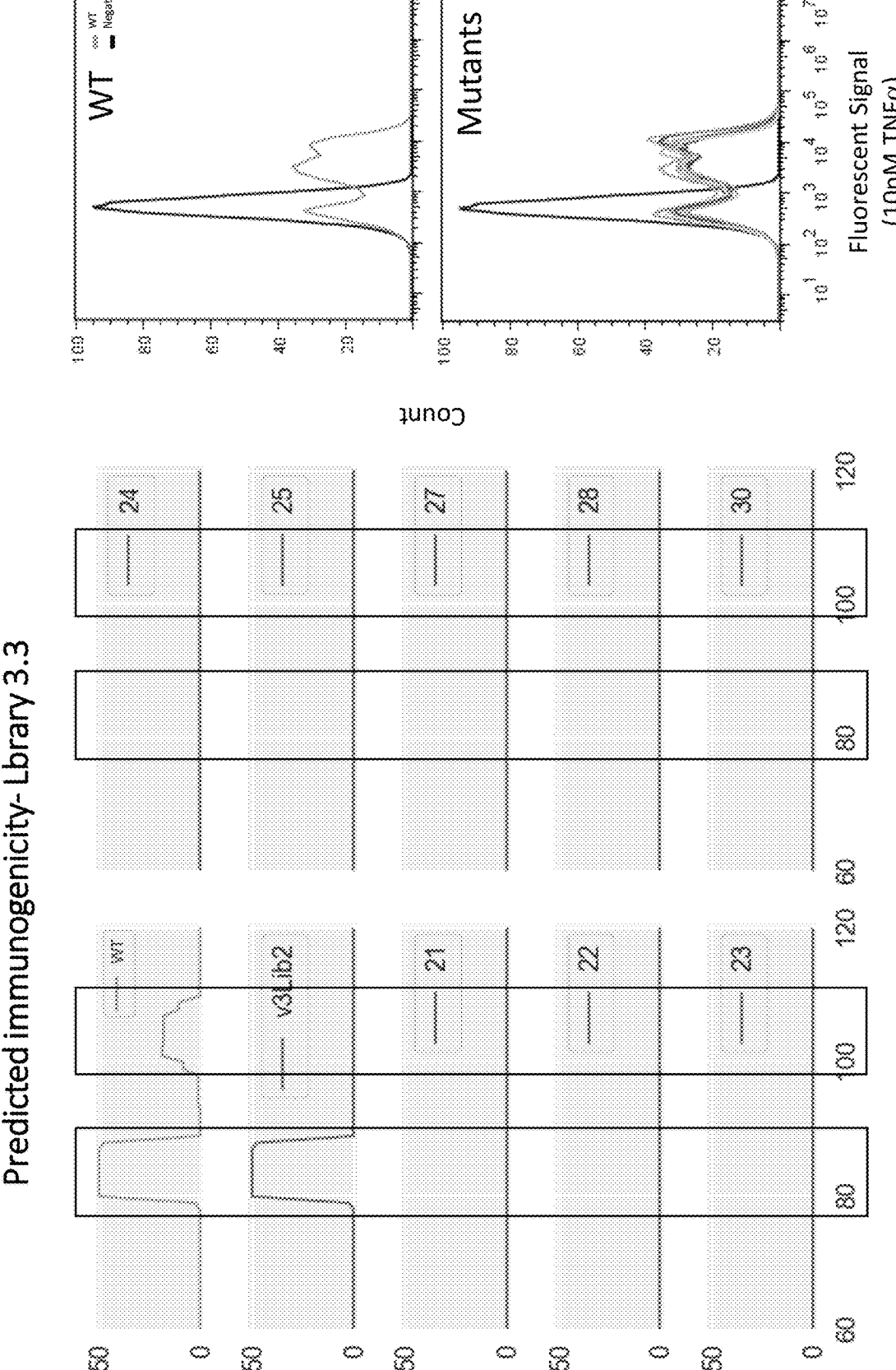
FIGS. 5A-5B: (5A) Line graphs of predicted immunogenicity of representative peptides from Library 3.3. WT Humira and the Variant 3 from Library 2 (used to make library 3.3) were used as controls. (5B) Histograms of TNFa binding to antibodies containing peptides from Library 3.3 as well as WT Humira as a control.

The four best epitopes from Library 2 based on binding to TNFa, low number of mutations and an immunogenicity score of zero, were selected for further study (VSWVST-SSSLD, VSWLSTSGSLD, VSGPSTSGNLD and VSWLSTSGNLD; SEQ ID NO: 97-100). These four epitopes were inserted into Library 1, to produce 4 libraries named Library 3.1, 3.2, 3.3 and 3.4 (Library 3.1 contains SEQ ID NO: 97, 3.2 contains SEQ ID NO: 98, 3.3 contains SEQ ID NO: 99 and 3.4 contains SEQ ID NO: 100). These libraries showed decreased immunogenicity at both hotspots (FIG. 5A). Once again mutants that were capable of binding TNFa at least as well as the WT Humira were selected (FIG. 5B, Table 6).

Next the binding of various mutant epitopes to various HLAs was tested. Five HLA alleles had been used in identifying the hotspots. Of these 4 were very strong binder and one was a binder, though it was less strong (HLA-DRB3*02:02) (Table 3). A sixth HLA allele that has not been in the initial analysis was also tested and found to strongly bind both WT hotspot sequences (see Table 3). This underlines the fact that the predicted immunogenicity is a universal aspect of this region.

TABLE 3

| Allele | Supertype | Frequency | WT Region 1 (corresponding to Lib 1) | WT Region 2 (corresponding to Lib 2) |
|---|---|---|---|---|
| HLA-DRB1*04:05 | DR4 | 6.2 | Ultra | Strong |
| HLA-DRB3*02:02 | DRB3 | 34.3 | Binder | Binder |
| HLA-DRB5*01:01 | Main_DR | 16 | Ultra | Binder |
| HLA-DRB1*0101 | Main_DR | 5.4 | Ultra | Strong |
| HLA-DRB1*04:04 | Unclassified | 2.4 | Ultra | Ultra |
| HLA-DRB1*10:01 | Unclassified | 1.1 | Strong | Ultra |

Figure 6A:
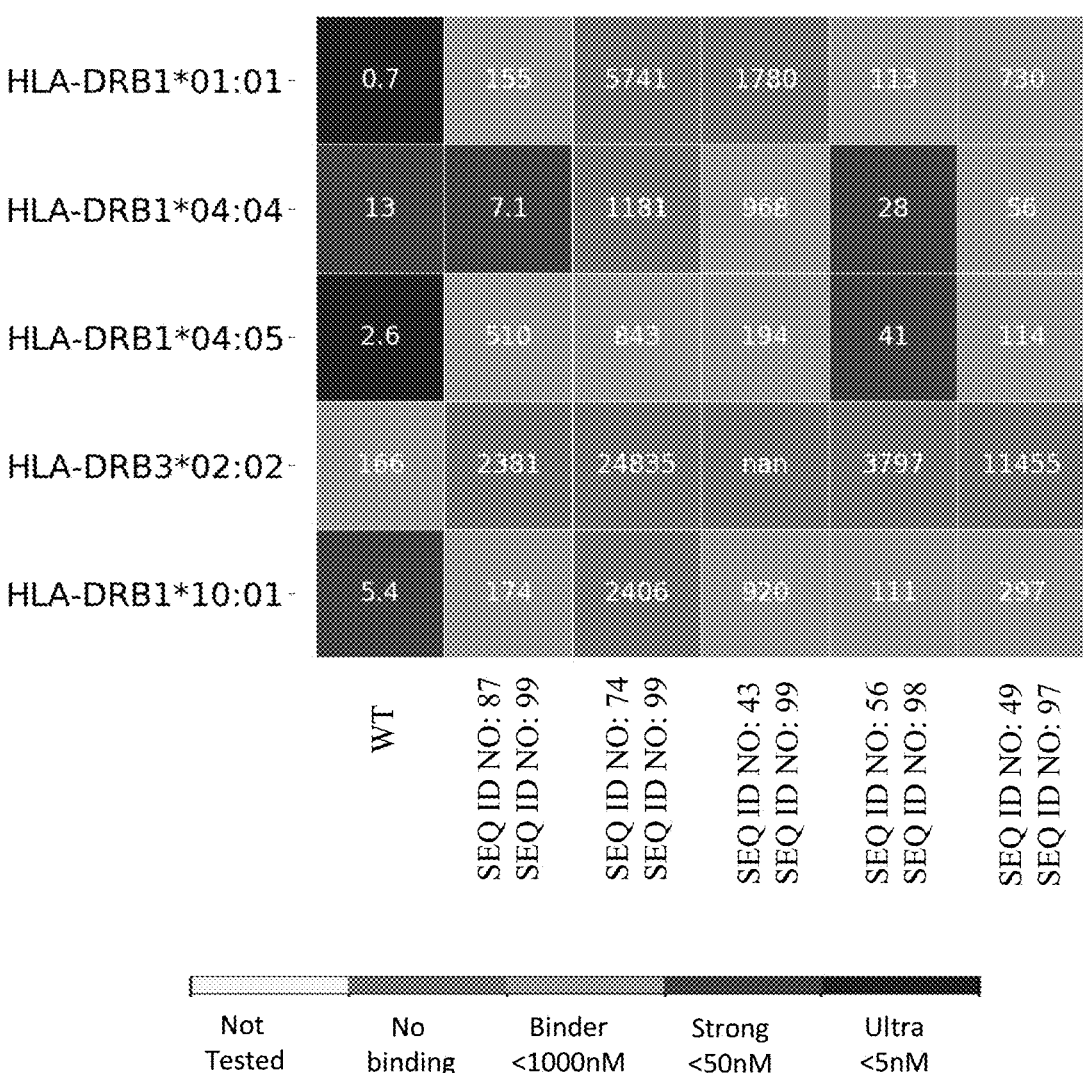
FIGS. 6A-6B: (6A-6B) Heat maps of (6A) binding of selected peptides as part of Adalimumab to six HLA alleles and (6B) the fold decrease in IC50 of selected peptides for the six HLA alleles.
Figure 6B:
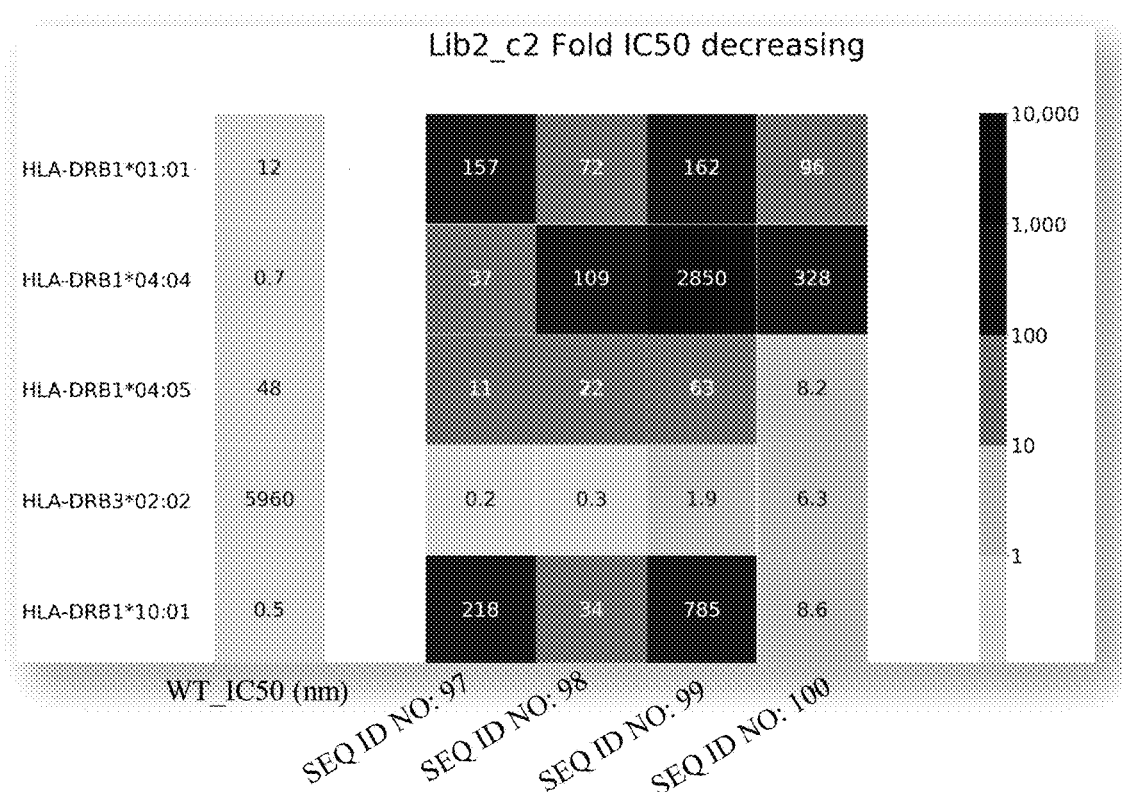
Figure 6B:
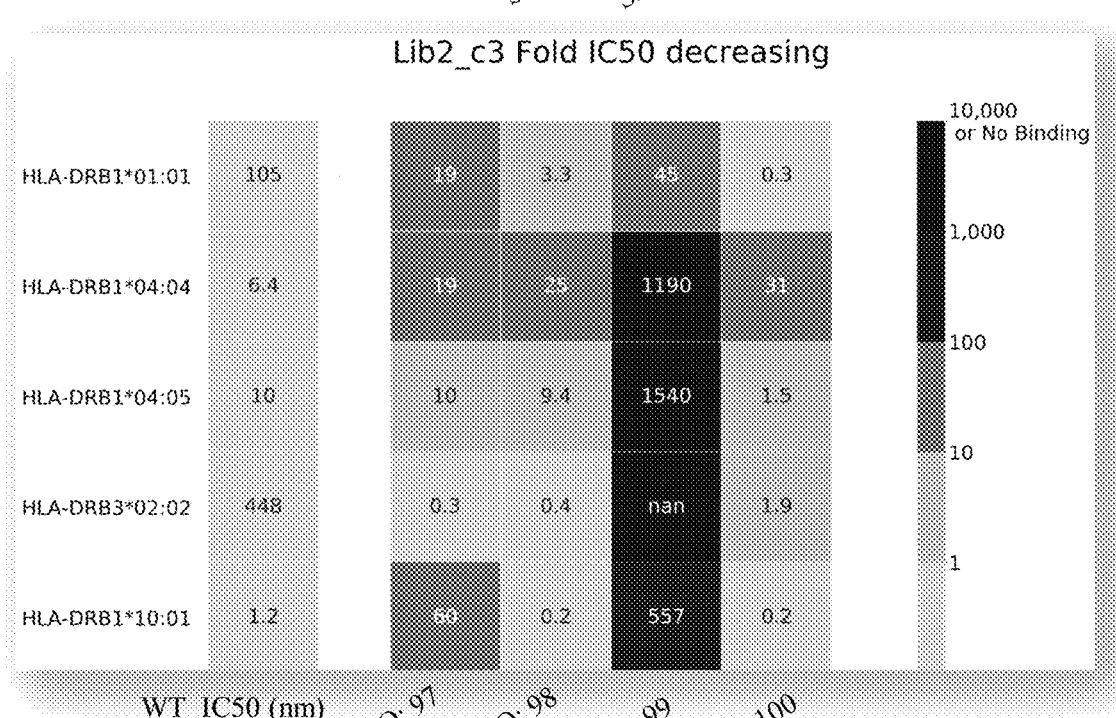
Figure 6B:
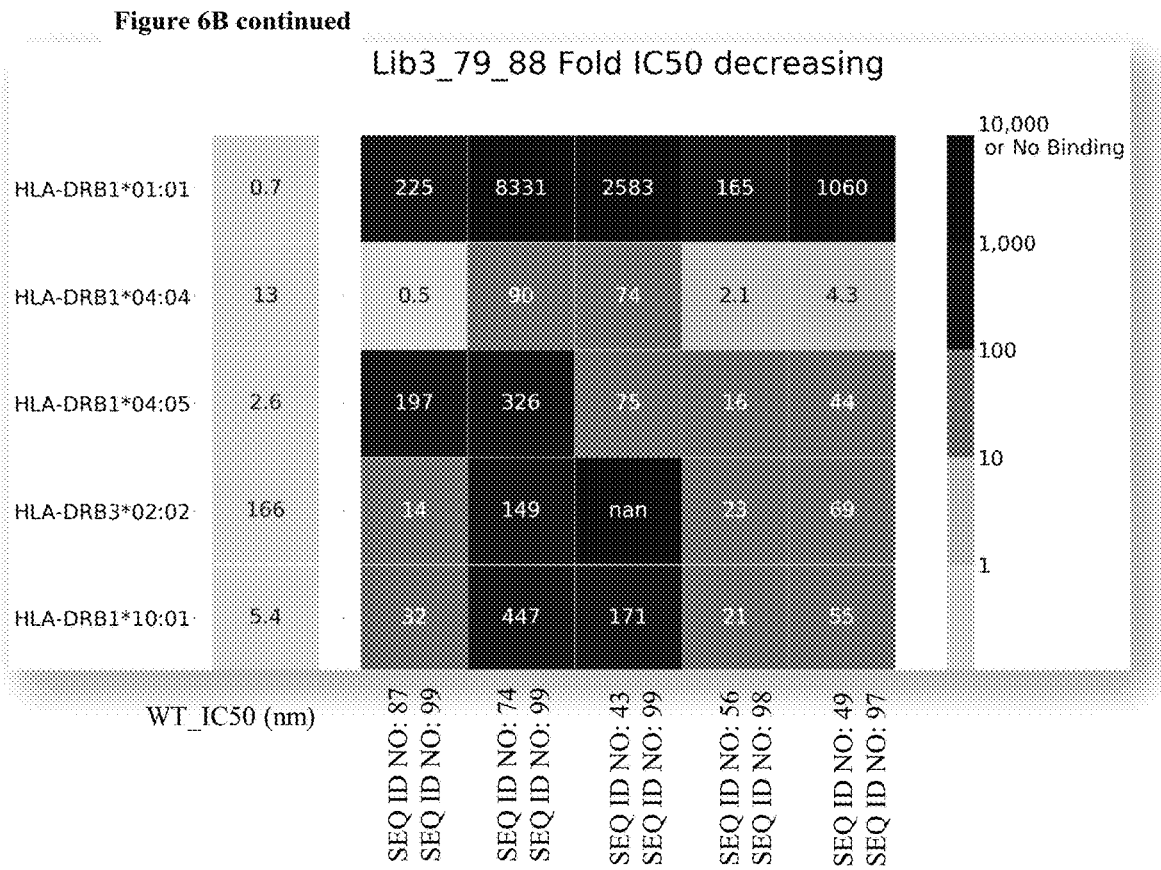

Even though these alleles bound many individual epitopes in the libraries, specific peptides had greatly reduced binding to the various HLAs. FIG. 6A shows the binding of selected peptides to the six HLAs. The effect of the amino acids flanking the epitopes was also tested. FIG. 6A shows both the c2 and c3 libraries which contain the same mutant peptides, but with different flanking sequences. Library c2. The effects of these flanking sequences were minimal. FIG. 6B shows the extent of the decrease in binding as compared to the WT Humira as measured by the fold decrease in IC50. Several of the peptides showed extremely reduced HLA binding and therefore extremely reduced immunogenicity.

Figure 3E:
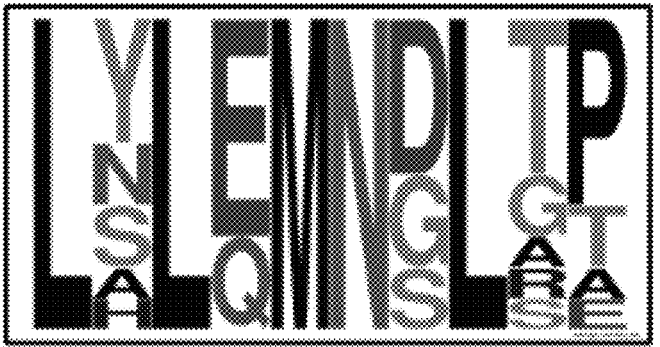
Figure 3F:
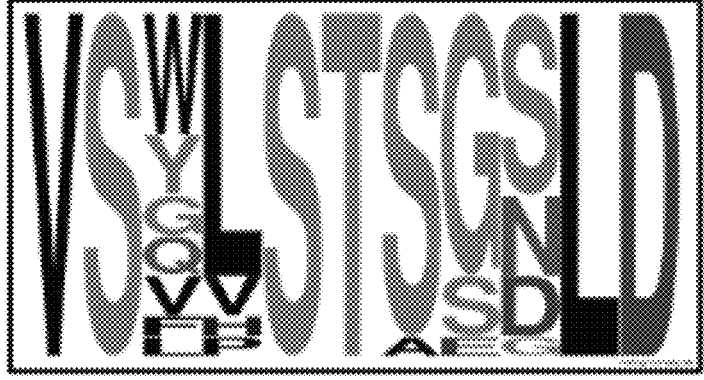

The top peptides from Library 1 that were found to have reduced immunogenicity and were found to still allow for WT levels of binding to TNFa are provided in Table 4. Table 4 also includes the top hits when binding to CTLA4 was assayed for the reduction of immunogenicity of Ipilimumab (see below). The top hits from Library 2 are provided in Table 5. The common epitope of selected sequences from Library 1 and Library 2 are presented in FIGS. 3E and 3F, respectively. The top epitopes within the HC:79-88 from the 3.1-3.4 combined libraries are provide in Table 6. Some epitopes were found in more than one library. The sequences found in Table 4 were also found in the combined libraries. Although the top hits are provided in the tables herein, they are merely exemplary. The common epitopes more accurately represent the breadth of functional peptides that were found. Indeed, the top hits for Humira were also found to reduce immunogenicity and to be functional when inserted into Ipilimumab and vice-versa.

TABLE 4

Top hits from Library 1 for Humira and Ipilimumab

| Sequences | SEQ ID NO: | Humira/Ipilimumab |
|---|---|---|
| LNLEMNDLTP | 10 | Humira |
| LNLQMNDLTP | 11 | Humira |
| LYLQMNSLRP | 12 | Humira |
| LYLEMNGLSP | 13 | Humira |
| LSLQMNDLTT | 14 | Humira |
| LHLEMNGLTE | 15 | Humira |
| LYLEMNDLGT | 16 | Humira |
| LYLEMNGLAP | 17 | Humira |
| LALEMNSLTP | 18 | Humira |
| LSLEMNDLGA | 19 | Humira |
| LTLEMNSLTP | 20 | Ipilimumab |
| LTLEMNSLTE | 21 | Ipilimumab |
| LTLEMNGLGP | 22 | Ipilimumab |
| LTLEMNGLAP | 23 | Ipilimumab |
| LYLEMNDLSD | 24 | Ipilimumab |
| LTLEMNGLSP | 25 | Ipilimumab |
| LTLEMNGLRP | 26 | Ipilimumab |
| LDLQMNGLGP | 113 | Ipilimumab |

TABLE 5

Top hits from Library 2

| Sequences | SEQ ID NO: | Used For |
|---|---|---|
| VSWVSTSSSLD | 97 | Generation of Lib 3.1 |
| VSWLSTSGSLD | 98 | Generation of Lib 3.2 |
| VSGPSTSGNLD | 99 | Generation of Lib 3.3 |
| VSWLSTSGNLD | 100 | Generation of Lib 3.4 |
| VSFHSTSEGLD | 101 | |
| VSWLSTSSSLD | 102 | |
| VSYLSTSGNLD | 103 | |
| VSYLSTSGSLD | 104 | |
| VSQLSTSGDLD | 105 | |
| VSQLSTSGSLD | 106 | |
| VSWLSTSGSLD | 107 | |
| VSQLSTSGDLD | 108 | |
| VSVLSTSGSLD | 109 | |
| VSLLSTSGSLD | 110 | |

TABLE 5-continued

Top hits from Library 2

| Sequences | SEQ ID NO: | Used For |
|---|---|---|
| VSVLSTSGDLD | 111 | |
| VSGVSTSGSLD | 112 | |

TABLE 6

Top hits from Libraries 3.1-3.4

| Sequences | SEQ ID NO: | Libraries found in |
|---|---|---|
| LYLEMNDLGP | 37 | 3.1, 3.3, 3.4 |
| LYLQMNSLTP | 38 | 3.1, 3.2, 3.4 |
| LYLEMNGLRE | 39 | 3.1 |
| LYLEMNSLGP | 40 | 3.1, 3.3 |
| LYLQMNDLAA | 41 | 3.1 |
| LYLEMNSLTP | 42 | 3.1, 3.4 |
| LYLEMNDLRP | 43 | 3.1, 3.3, 3.4 |
| LHLEMNDLAP | 44 | 3.1 |
| LHLEMNDLSP | 45 | 3.1 |
| LYLEMNDLSP | 46 | 3.1, 3.3, 3.4 |
| LYLEMNSLAP | 47 | 3.1, 3.2, 3.4 |
| LALQMNDLRP | 48 | 3.1 |
| LYLQMNDLTP | 49 | 3.1, 3.2, 3.4 |
| LYLQMNDLGP | 50 | 3.1 |
| LHLQMNDLRP | 51 | 3.1 |
| LYLEMNDLAP | 52 | 3.1 |
| LDLEMNDLRT | 53 | 3.1 |
| LYLEMNSLTK | 54 | 3.1 |
| LDLQMNDLTP | 55 | 3.2 |
| LYLEMNDLGA | 56 | 3.2 |
| LSLEMNDLRP | 57 | 3.2 |
| LYLEMNSLTA | 58 | 3.2 |
| LHLQMNDLTP | 59 | 3.2 |
| LYLEMNSLSP | 60 | 3.2 |
| LSLEMNDLAP | 61 | 3.2 |
| LSLEMNDLTT | 62 | 3.2 |
| LYLEMNDLAD | 63 | 3.2 |
| LHLEMNSLTP | 64 | 3.2 |
| LFLEMNDLGP | 65 | 3.2 |
| LALEMNDLRP | 66 | 3.2 |
| LYLEMNDLSK | 67 | 3.2 |
| LYLEMNDLGE | 68 | 3.2 |

TABLE 6-continued

Top hits from Libraries 3.1-3.4

| Sequences | SEQ ID NO: | Libraries found in |
|---|---|---|
| LYLEMNDLTA | 69 | 3.2 |
| LYLEMNDLTP | 70 | 3.2, 3.3, 3.4 |
| LYLQMNDLRA | 71 | 3.2, 3.4 |
| LSLEMNGLTP | 72 | 3.2 |
| LYLEMNDLAT | 73 | 3.2 |
| LNLQMNDLRA | 74 | 3.2, 3.3 |
| LALEMNDLAE | 75 | 3.3 |
| LHLQMNSLTP | 76 | 3.3 |
| LSLEMNDLSD | 77 | 3.3 |
| LYLEMNGLGA | 78 | 3.3 |
| LDLEMNDLSP | 79 | 3.3 |
| LALEMNSLTD | 80 | 3.3 |
| LTLEMNGLAP | 81 | 3.3 |
| LTLQMNDLAP | 82 | 3.3 |
| LDLQMNSLAA | 83 | 3.3 |
| LALEMNGLTP | 84 | 3.3 |
| LNLEMNSLGP | 85 | 3.3 |
| LDLQMNSLAE | 86 | 3.3 |
| LDLQMNSLSA | 87 | 3.3 |
| LYLQMNDLAT | 88 | 3.3 |
| LYLQMNGLTA | 89 | 3.3 |
| LDLQMNDLSP | 90 | 3.3 |
| LSLEMNGLTD | 91 | 3.3 |
| LDLQMNDLGP | 92 | 3.3 |
| LDLEMNDLGP | 93 | 3.3 |
| LYLEMNSLTT | 94 | 3.4 |
| LYLEMNDLTT | 95 | 3.4 |
| LHLEMNDLRP | 96 | 3.4 |

Finally, the epitopes are validated via T cells functionality assays using PBMCs collected from Humira treated patients that have developed ADA. The collected PBMCs are mixed with the mutant Humira antibodies generated and T cell activation is measured by secretion of a pro-inflammatory cytokine. It is confirmed that the variant antibodies do not activate T cells from the patients that developed ADA.

Example 3: Commercially Available Antibodies Comprising the HC:79:88 Hotspot 462 different therapeutic antibodies were examined for the HC:79:88 hotspot. The HC99:109 hotspot is in the CDR3 region of adalimumab and thus would not be expected to be found in other antibodies. Of these, 118 were found to have the exact sequence of the HC:79:88 hotspot. The 118 antibodies are provided in Table 3 hereinabove. This epitope (LYLQMNSLRA, SEQ ID NO: 1) was one of the most common shared epitopes found in the 462 antibodies.

Example 4: Engineering of Immunogenicity Reduced Ipilimumab

Figure 7B:
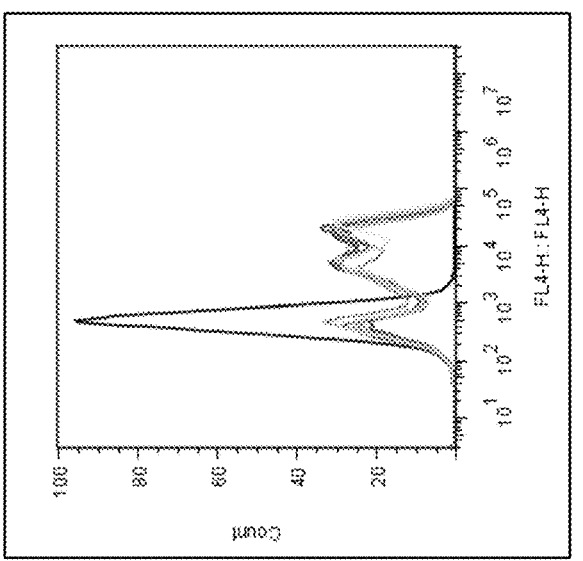
Figure 7A:
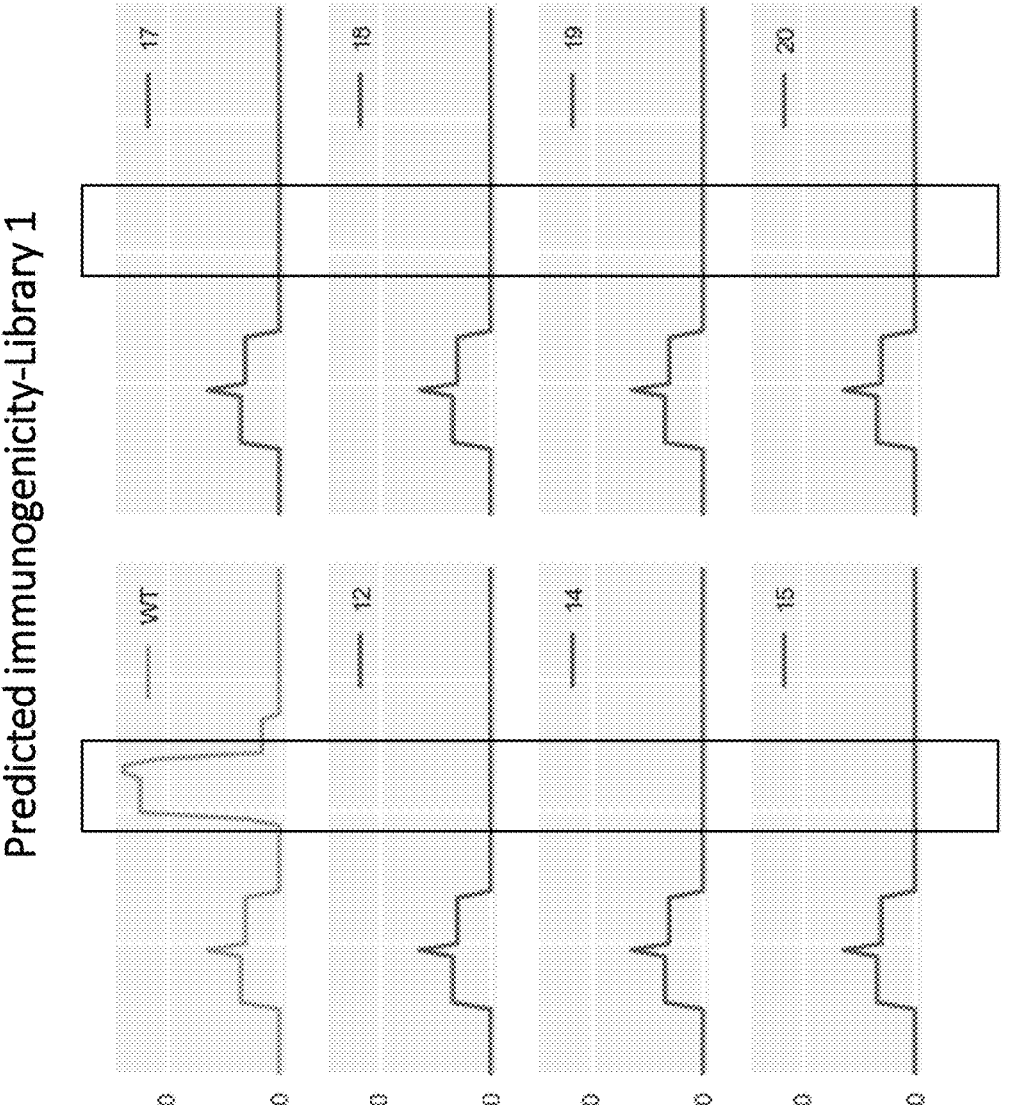
Figure 7C:
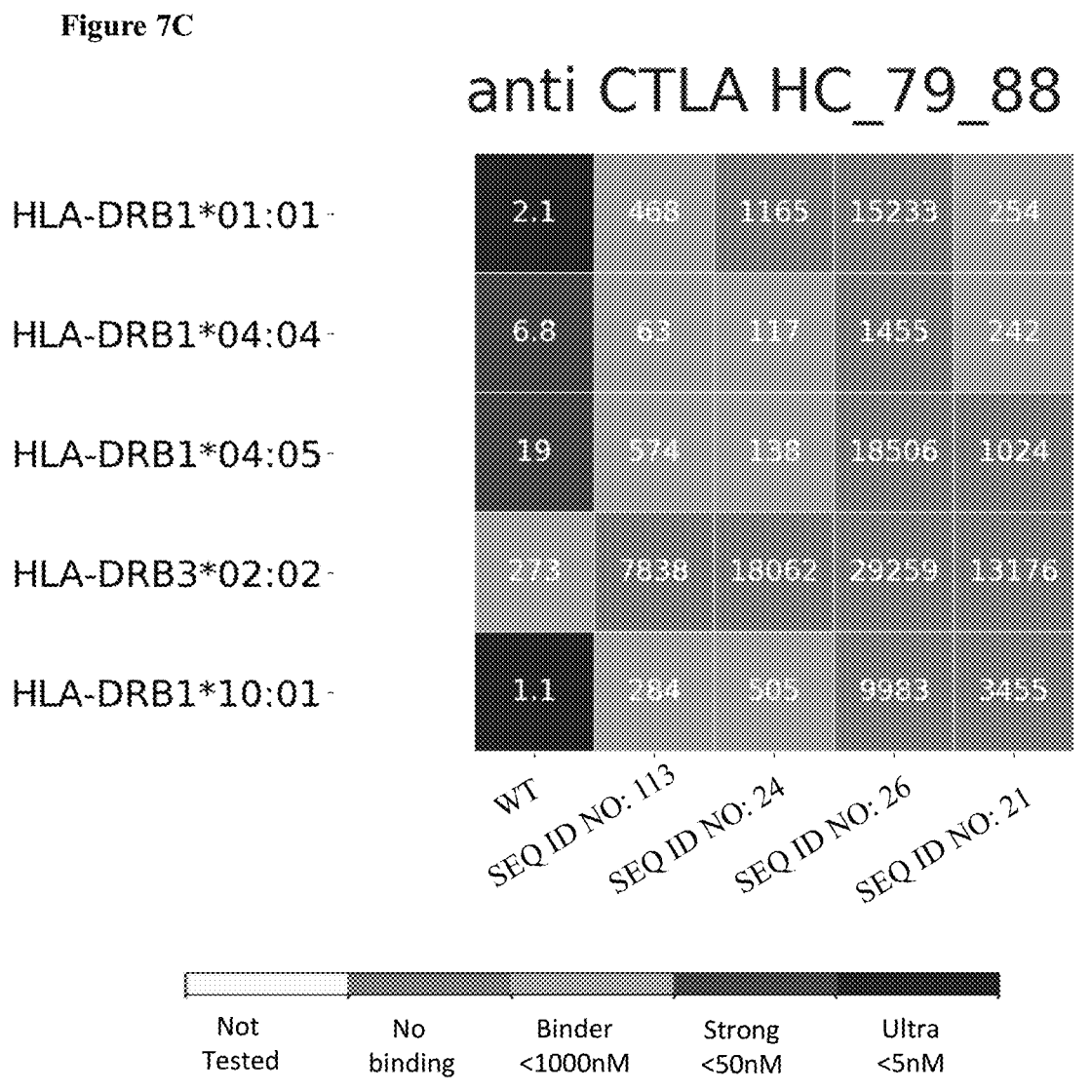
Figure 7D:
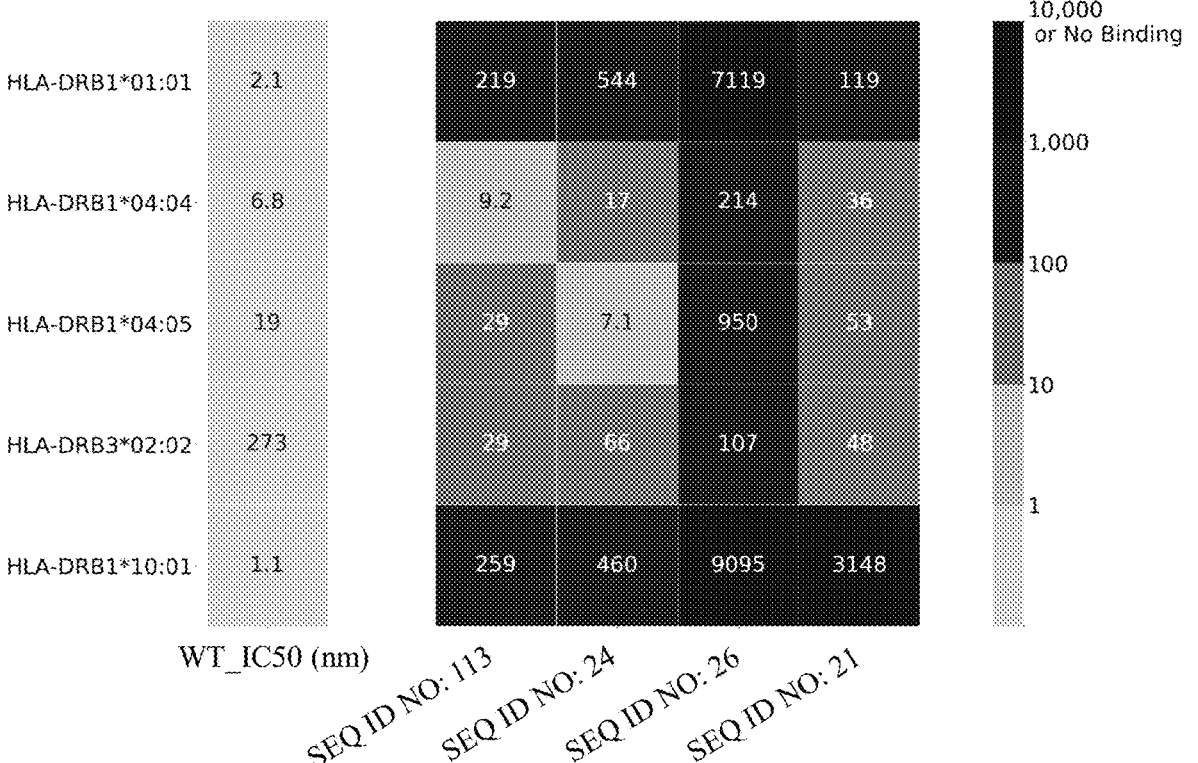
Figure 7E:
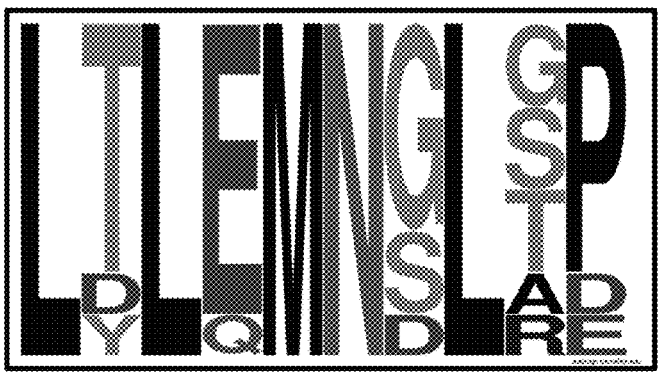

One of the 118 antibodies was Ipilimumab. Ipilimumab is a therapeutic anti-CTLA4 monoclonal antibody. Administration of this antibody has also been reported to induce ADAs. Therefore, using the scheme described hereinabove, variants of Ipilimumab with reduced immunogenicity were designed. A scan of the sequence of Ipilimumab showed that it also shared the core HC:79:88 hotspot. Therefore, Library 1 was transferred into the sequence of Ipilimumab as this would also be predicted to reduce immunogenicity (FIG. 7A). As before, binding to CTLA4 on the surface of yeast cells was confirmed for the antibody variants (FIG. 7B). As before, decreased immunogenicity was confirmed by testing binding to the six HLA alleles (FIG. 7C). As expected, several of the variants showed a significant decreased of IC50 for the tested HLAs (FIG. 7D). Thus, this replacement strategy was effective for making both Adalimumab and Ipilimumab less immunogenic and indeed is effective on any antibody that share these common hotspots. The epitope of selected variants of the hotspot region for Ipilimumab is provided in FIG. 7E.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for reducing the immunogenicity of an antibody, the method comprising:
   a. providing a first nucleic acid molecule comprising a coding sequence which encodes an amino acid sequence of said antibody, wherein said amino acid sequence comprises LYLQMNSLRA (SEQ ID NO: 1),
   b. replacing the nucleic acid sequence encoding SEQ ID NO: 1 in said first nucleic acid molecule with a nucleic acid sequence encoding $LX_1LX_2MNX_3LX_4X_5$ (SEQ ID NO: 2) to produce a second nucleic acid molecule encoding an amino acid sequence of a modified version of said antibody, wherein:
   $X_1$ is selected from D, H, N, S, Y, A, F, and T,
   $X_2$ is selected from E, and Q,
   $X_3$ is selected from D, G, and S,
   $X_4$ is selected from A, G, R, S, and T,
   $X_5$ is selected from A, D, E, N, P, T and K,
      wherein said SEQ ID NO: 1 and SEQ ID NO: 2 comprise a different amino acid sequence;
   c. producing a modified version of said antibody from said second nucleic acid molecule;
   thereby reducing the immunogenicity of an antibody.

2. The method of claim 1, wherein a heavy chain of said first antibody comprises SEQ ID NO: 1 or wherein amino acids 79-88 of said heavy chain of said antibody is SEQ ID NO: 1.

3. The method of claim 1, wherein said SEQ ID NO: 2 consists of a sequence selected from SEQ ID NO: 10-26, 37-96 and 113.

4. The method of claim 1, further comprising confirming binding of said modified version of said antibody to a target or an epitope of said antibody.

5. The method of claim 4, wherein said confirmed binding comprises measuring a binding value of said modified version of said antibody to said target or epitope by a binding assay and confirming said binding value of said modified version of said antibody is at least 70% of a binding value of said first antibody to said target or epitope.

6. The method of claim 1, wherein said first antibody is selected from the antibodies provided in Table 2.

7. The method of claim 1, wherein said antibody is selected from the group consisting of: afasevikumab, adalimumab, sutimlimab, remtolumab, terextumab, elotuzumab, bimekizumab, sofituzumab vedotin, rozanolixizumab, lanadelumab, suvratoxumab, gosuranemab, ipilimumab, dupliumab, efalizumab, frovocimab, emapalumab, alirocumab, inclacumab, crotedumab, avelumab, opicinumab, emicizumab, durvalumab, solanexumab, ramucirumab, tovetumab, pertuzumab, suptavumab, nesvacumab, quilizumab, brazikumab, denosumab, varlilumab, tremelimumab, igatuzumab, robatumumab, prezalumab, prasinezumab, panobacumab, otilimab, otelixizumab, osocimab, lorvotuzumab mertansine, lexatumumab, icrucumab, fremanexumab, elgemtumab, daratumumb, corncizumab, bapineuzumab, and anrukinzumab.

8. The method of claim 4, wherein said antibody is adalimumab or ipilimumab.

* * * * *